(12) United States Patent
Turk et al.

(10) Patent No.: US 11,293,022 B2
(45) Date of Patent: Apr. 5, 2022

(54) GENOME EDITING ENHANCEMENT

(71) Applicant: INTEGRATED DNA TECHOLOGIES, INC., Coralville, IA (US)

(72) Inventors: Rolf Turk, Iowa City, IA (US); Mark A. Behlke, Coralville, IA (US); Chris Vinci, Evanston, IL (US)

(73) Assignee: Integrated DNA Technologies, Inc., Coralville, IA (US)

(*) Notice: Subject to any disclaimer, the term of this patent is extended or adjusted under 35 U.S.C. 154(b) by 213 days.

(21) Appl. No.: 15/839,820

(22) Filed: Dec. 12, 2017

(65) Prior Publication Data
US 2018/0273938 A1 Sep. 27, 2018

Related U.S. Application Data

(60) Provisional application No. 62/432,950, filed on Dec. 12, 2016.

(51) Int. Cl.
| | |
|---|---|
| *C12N 15/11* | (2006.01) |
| *C12N 15/90* | (2006.01) |
| *C12N 9/96* | (2006.01) |
| *C12N 9/22* | (2006.01) |
| *C12N 15/113* | (2010.01) |

(52) U.S. Cl.
CPC ............ *C12N 15/11* (2013.01); *C12N 9/22* (2013.01); *C12N 9/96* (2013.01); *C12N 15/907* (2013.01); *C12N 15/113* (2013.01); *C12N 2310/20* (2017.05); *C12N 2320/32* (2013.01); *C12N 2800/80* (2013.01)

(58) Field of Classification Search
CPC ......................... C12N 9/96; C12N 2310/20
See application file for complete search history.

(56) References Cited

U.S. PATENT DOCUMENTS

| | | |
|---|---|---|
| 5,672,695 A | 9/1997 | Eckstein et al. |
| 6,248,878 B1 | 6/2001 | Matulic-Adamic et al. |
| 8,697,359 B1 | 4/2014 | Zhang |
| 9,840,702 B2 | 12/2017 | Collingwood et al. |
| 2014/0273226 A1 | 9/2014 | Wu |
| 2014/0273232 A1 | 9/2014 | Zhang et al. |
| 2014/0295557 A1 | 10/2014 | Joung et al. |
| 2015/0059010 A1 | 2/2015 | Cigan et al. |
| 2015/0073041 A1 | 3/2015 | Saltzman |
| 2016/0024524 A1 | 1/2016 | Joung et al. |
| 2016/0208241 A1 | 7/2016 | Tsai et al. |
| 2016/0208243 A1 | 7/2016 | Zhang et al. |
| 2016/0215300 A1 | 7/2016 | May et al. |
| 2016/0289675 A1 | 10/2016 | Ryan et al. |
| 2016/0362667 A1 | 12/2016 | Donohoue et al. |
| 2019/0010519 A1* | 1/2019 | Corn .................. A01K 67/0271 |

FOREIGN PATENT DOCUMENTS

| | | | |
|---|---|---|---|
| CN | 106244591 A | 8/2016 | |
| WO | WO-2006080946 A2 * | 8/2006 | ............ C07H 21/00 |
| WO | 2014065596 A1 | 5/2014 | |
| WO | 2014124226 A1 | 8/2014 | |
| WO | 2014144592 A2 | 9/2014 | |
| WO | 2016080097 A1 | 5/2016 | |
| WO | 2016089433 A1 | 6/2016 | |
| WO | 2016115179 A1 | 7/2016 | |
| WO | 2016161207 A1 | 10/2016 | |
| WO | 2016164356 A1 | 10/2016 | |
| WO | 2017147432 A1 | 8/2017 | |
| WO | 2017184799 A1 | 10/2017 | |

OTHER PUBLICATIONS

Zhu et al. (1999) A novel method for increasing the transformation efficiency of *Escherichia coli*—application for bacterial artificial chromosome library construction. Nucleic Acids Research, 27(3):910-911 (Year: 1999).*
Shiestl et al. (1989) High efficiency transformation of intact yeast cells using single stranded nucleic acids as a carrier. Current Genetics, 16:339-346 (Year: 1989).*
Sun et al. (2015) Self-Assembled DNA Nanoclews for the Efficient Delivery of CRISPR-Cas9 for Genome Editing. Angewandte Chemie, 54:12029-12033 (Year: 2015).*
Holmes et al. (1996) Fe·bleomycin as a probe of RNA conformation. Nucleic Acids Research, 24(17):3399-3406 (Year: 1996).*
Behlke, M.A., "Chemical Modification of siRNAs for In Vivo Use" Oligonucleotides (2008) 18:305-320.
Briner, A.E. et al., "Guide RNA Functional Modules Direct Cas9 Activity and Orthogonality." Molecular Cell (2014) 56:333-339.
Eder, P.S. et al., "Substrate Specificity and Kinetics of Degradation of Antisense Oligonucleotides by a 3' Exonuclease in Plasma." Antisense Research and Development (1991) 1:141-151.
Gasiunas, G. et al., "Cas9-crRNA ribonucleoprotein complex mediates specific DNA cleavage for adaptive immunity in bacteria." Proc Natl Acad Sci USA (2012) 109(39):E2579-86.
Jinek, M. et al., "A Programmable Dual-RNA-Guided DNA Endonuclease in Adaptive Bacterial Immunity." Science (2012) 337(6096):816-21.
Jinek, M. et al., "Structures of Cas9 Endonucleases Reveal RNA-Mediated Conformational Activation." Science (2014) 343:1215-26.
Kurreck, J., "Antisense technologies Improvement through novel chemical modifications." Eur. J. Biochem. (2003) 270:1628-1644.
Lennox, K.A. et al., "Chemical modification and design of anti-miRNA oligonucleotides." Gene Therapy (2011) 18:1111-1120.

(Continued)

*Primary Examiner* — Neil P Hammell
(74) *Attorney, Agent, or Firm* — Klintworth & Rozenblat IP LLP

(57) ABSTRACT

This invention pertains to single-stranded carrier nucleic acids and their methods of use for enhancing genome editing ribonucleoprotein complex transfection into cells and the resulting enhancement of CRISPR editing on the target DNA within those cells, as well as introduction of chemical modifications which reduce the integration of the single-stranded carrier nucleic acids at double-stranded breaks.

13 Claims, 22 Drawing Sheets

Specification includes a Sequence Listing.

(56) References Cited

OTHER PUBLICATIONS

Nishimasu, H. et al., "Crystal Structure of Cas9 in Complex with Guide RNA and Target DNA." Cell (2014) 156 (5):935-949.
O'Connell, M.R. et al., "Programmable RNA recognition and cleavage by CRISPR/Cas9." Nature (2014) 516:263-278.
Sahin, U. et al., "mRNA-based therapeutics—developing a new class of drugs." Nat Rev Drug Discov (2014) 13:759-780.
Xu, T. et al., "Cas9-Based Tools for Targeted Genome Editing and Transcriptional Control." Applied Environmental Microbiology (2014) 80(6):1544-1552.
Fu et al., "IMproving CRISPR-Cas nuclease specificity using truncated guide RNAs," Nature Biotechnol. 32(3):279-284 (2014).
Lennox et al., "Improved Performance of Anti-miRNA Oligonucleotides Using a Novel Non-Nucleotide Modifier," Molecular Therapy-Nucleic Acids 2:e117 (2013).
Cencic et al., "Protospacer Adjacent Motif (PAM)-Distal Sequences Engage CRISPR Cas9 DNA Target Cleavage", PLOS One 9(10):e109213 (2014).
Hendel et al., "Chemically modified guide RNAs enhance CRISPR-Cas genome editing in human primary cells", Nat. Biotech. 33(9):985 (2015).
Jinek et al., Supplementary Materials for "A Programmable Dual-RNA-Guided DNA Endonuclease in Adaptive Bacterial Immunity", Science 337 (2012).
Rahdar et al., "Synthetic CRISPR RNA-Cas9-guided genome editing in human cells," Proc. Natl. Acad. Sci. (pub. Nov. 16, 2015).
International Search Report and Written Opinion for PCT/US2015/066942 dated Aug. 25, 2016, 25 pages.
Notification of Transmittal of the International Search Report and the Written Opinion of the International Searching Authority, or the Declaration, for PCT/US2017/065923, dated Apr. 12, 2018, 15 pages.
Nelles, David A., et al., "Programmable RNA Tracking in Live Cells with CRISPR/Cas9" Cell, Cell Press, vol. 165, No. 2, Mar. 17, 2016 (Mar. 17, 2016), pp. 488-496, XP029496630, ISSN: 0092-8674, DOI: 10.1016/J. CELL.2016.02.054 figure 1.
Xiaoxiao, Zhu et al., "An Efficient Genotyping Method for Genome-modified Animals and Human Cells Generated with CRISPR/Cas9 System", Scientific Reports, vol. 4, No. 1, Sep. 19, 2014 (Sep. 19, 2014), XP055461892, doi: 10.1038/SREP06420 (p. 2, col. 1, Last Para); Figure 1.

Notification of Transmittal of the International Search Report and the Written Opinion of the International Searching Authority, or the Declaration, for PCT/US2017/63161, dated Apr. 24, 2018, 16 pages.
Zeutsche, B., et al., Cpf1 is a Single RNA-Guided Endonuclease of a Class 2 CRISPR-Cas System, Cell. Oct. 22, 2015, Epub Sep. 25, 2015, vol. 163, No. 3; pp. 789-771; p. 760, 2nd column, 1st paragraph; p. 765, 2nd column, 1st paragraph; p. 769, 1st column, 6th paragraph—2nd Column, 1st paragraph; Figure 7, p. S2-S8; Table S1; DOI 10.1016/j.cell.2015.09.038.
Kleinstiver, B., et al.. Genome-wide specificities of CRISPR-Cas Cpf1 nucleases in human cells. Nature Biotechnology. Aug. 2015, Epub Jun. 27, 2016, vol. 34, No. 8; pp. 869-874; abstract; p. 870, 1st column, 1st-2nd paragraphs; Figure 2; DOI: 10.1038/nbt.3620.
Notification of Transmittal of the International Search Report and The Written Opinion of the International Searching Authority, or the Declaration, for PCT/US17/55952, dated Apr. 6, 2018, 17 pages.
Makarova, K.S., et al., A putative RNA-interference-based immune system in prokaryotes: computational analysis of the predicted enzymatic machinery, functional analogies with eukaryotic RNAi, and hypothetical mechanisms of action. Biol Direct, 2006. 1: p. 7.
Tsai, S.Q., et al., GUIDE-seq enables genome-wide profiling of off-target cleavage by CRISPR-Cas nucleases. Nat Biotechnol, 2015. 33(2): p. 187-97.
Slaymaker, I.M., et al., Rationally engineered Cas9 nucleases with improved specificity. Science, 2016. 351(6268): p. 84-8.
Kleinstiver, B.P., et al., High-fidelity CRISPR-Cas9 nucleases with No. detectable genome-wide off-target effects. Nature, 2016. 529(7587): p. 490-495.
Anders et al., Nature 2014, 513(7519) p. 569-73.
Chen, et al., Nature 2017, http://dx.doi.org/10.1038/nature24268 (2017).
Dong, et al., Science 2013, 339 p. 819-823.
Mali et al., Science, 2013, 339 p. 823-826.
Cho et al., Genome Research, 2014, 24 p. 132-141.
Aida et al., Genome Biology, 2015, 16 p. 87-98.
Non-Final Office Action for U.S. Appl. No. 14/975,709, dated Feb. 21, 2017, 13 pages.
Final Office Action for U.S. Appl. No. 14/975,709, dated Jul. 25, 2016, 9 pages.
Non-Final Office Action for U.S. Appl. No. 14/975,709 dated Mar. 25, 2016, 14 pages.

* cited by examiner

GENOME EDITING ENHANCEMENT

CROSS-REFERENCE TO RELATED APPLICATIONS

This application claims benefit of priority under 35 U.S.C. 119 to U.S. Provisional Patent Application Ser. No. 62/432,950, filed Dec. 12, 2016 and entitled "GENOME EDITING ENHANCEMENT," the contents of which are herein incorporated by reference in their entirety.

SEQUENCE LISTING

The instant application contains a Sequence Listing that has been submitted in ASCII format via EFS-Web and is hereby incorporated by reference in its entirety. The ASCII copy, created on Feb. 27, 2018, is named IDT01-011-US_ST25.txt, and is 46,706 bytes in size.

FIELD OF THE INVENTION

This invention pertains to single-stranded carrier nucleic acids and their methods of use for enhancing genome editing ribonucleoprotein (RNP) complex transfection into cells and the resulting enhancement of CRISPR editing on the target DNA within those cells.

BACKGROUND OF THE INVENTION

The recently discovered bacterial CRISPR/Cas9 system is used to generate editing events in double-stranded DNA. The system relies on the nuclease activity of Cas9, which activity leads to double-stranded breaks (DSBs), as well as a guide RNA that directs the Cas9 protein to a specific sequence-dependent location (see Jinek et al., Science (2012) 337:816-821). The CRISPR/Cas9 system has been successfully used to alter genomic DNA in different model systems as well as in various organisms (see Harms et al., Curr Protoc Hum Genet (2015) 83:15.7.1-15.7.27).

Double-stranded breaks (DSBs) in genomic DNA can be repaired through different mechanisms, which are cell cycle-dependent (see Salsman et al., Biochem Cell Biol (2017) 95:187-201). Three major pathways exist; canonical non-homologous end-joining (c-NHEJ), alternative non-homologous end-joining (alt-NHEJ), and homologous repair (HR). c-NHEJ occurs throughout the cell cycle, whereas alt-NHEJ and HR occur only during G2/S phase. As a result, the majority of DSBs are repaired through c-NHEJ, a process which is error-prone and has a high frequency of insertions and deletions.

CRISPR/Cpf1 is a DNA-editing technology analogous to the CRISPR/Cas9 system in that it is also an RNA-guided endonuclease of a class II CRISPR/Cas system (see Zetsche et al., Cell. (2015) 163(3):759-71). Since Cpf1 is a smaller and simpler endonuclease than Cas9, its use can potentially overcome some of the limitations of the CRISPR/Cas9 system. While Cpf1 was originally characterized from *Prevotella* and *Francisella*, many homologues of Cpf1 exist from other bacterial species that have different properties. Codon optimized versions of the Cpf1 enzymes from *Acidaminococcus* and *Lachnospiraceae* were shown to efficiently target DNMT1 in human cells, whereas the *Prevotella* and *Francisella* variants were inactive for genome editing in mammalian cells.

There are several notable differences between the Cpf1 and Cas9 systems. For Cas9, a Cas9 endonuclease and a CRISPR guide RNA (gRNA) comprised of a crRNA and a tracrRNA must be present in a cell for DNA cleavage to occur. Cpf1 does not need a tracrRNA to be functional, requiring only a single short crRNA. This greatly simplifies the system since less RNA must be optimized and synthesized for sequence-specific targeting. Cpf1 recognizes a T-rich protospacer-adjacent motif (PAM) as opposed to the G-rich PAM of Cas9, which enables new targeting possibilities in the genome. When editing its target DNA, Cpf1 creates double stranded breaks with sticky ends containing 4-5 nucleotide overhangs, rather than the blunt ends created by Cas9. The advantage of this is that it may ensure proper orientation as well as providing microhomology during non-homologous end joining (NHEJ). This could also be advantageous in non-dividing cell types that tend to be resistant to homology-directed repair (HDR). Furthermore, when Cpf1 cleaves, it does so further away from PAM than Cas9, which is also further away from the target site. As a result, the protospacer, and especially the seed sequence of the protospacer, are less likely to be edited, thereby leaving open the potential for a second round of cleavage if the correct repair pathway doesn't happen the first time.

The CRISPR/Cas9 components or CRISPR/Cpf1 components can be introduced into the cell using various approaches. Examples include plasmid or viral expression vectors (which lead to endogenous expression of either Cas9/Cpf1, the gRNAs (crRNA for Cpf1), or both), Cas9 or Cpf1 mRNA with separate gRNA/crRNA transfection, or delivery of the Cas9 or Cpf1 protein with the gRNA or crRNAs as a ribonucleoprotein (RNP) complex (see Kouranova et al., Hum Gen Ther (2016) 27(6):464-475). Each approach leads to different time-frames of availability of the active CRISPR system in the transfected cell.

The specificity of the CRISPR/Cas9 system is directed by a subdomain of the guide RNA, the "protospacer" sequence. The protospacer sequence is designed to have perfect homology to the target site. Although the protospacer will direct Cas9 to the target site, other sites with high homology can be targeted and cleaved by the CRISPR/Cas9 system as well. These are referred to as off-target effects. The amount of off-target effects correlates with the amount and time of Cas9 protein expression (see Liang et al., J Biotech (2015) 208:44-53). Delivery of Cas9 protein complexed with guide RNA into cells leads to high levels of on-target genome editing, and relatively low off-target editing events. This result is due to high turn-over of Cas9 protein, leading to a short activity time-frame. As such, RNP-mediated genome editing is safer for therapeutic applications than other delivery methodologies (see Schumann et al., PNAS (2015) 112(33):10437-10442). Thus, delivery of Cas9 protein complexed with guide RNA, known as the ribonucleoprotein complex, is a preferred method to achieve genome editing. The gRNA can be a hairpin single guide design (sgRNA) or can be a complex of a target-specific crRNA paired with a Cas9-binding tracrRNA (crRNA:tracrRNA pair).

For CRISPR/Cpf1, Cpf1 endonuclease and crRNA must be present in a cell for DNA cleavage to occur. While there are various approaches that can be used to introduce these components into the cell, a preferable method is to deliver the Cpf1 protein along with the crRNA as a ribonucleoprotein (RNP) complex (see Ramakrishna et al., Gen Res (2014) 24:1020-1027). The rationale is that, since the level of off target effects (OTE) has been shown to be directly correlated with the amount of Cas9 and the time of its exposure to the target DNA, the same would be possibly true for Cpf1. In short, the amount of OTE is high with plasmid delivery and low with protein delivery due to the higher turnover of enzyme after protein delivery (see Liang). As noted above, the CRISPR RNP delivery system was used with Cas9, and has recently been shown to work with Cpf1 as well (see Hur et al., Nat Biotechnol. (2016) 34(8):807-8).

The level of genome editing via electroporation of RNP complexes can be increased by increasing the efficiency of RNP delivery to the cells by addition of single-stranded DNA oligonucleotides (ssODN), also known as 'carrier DNA' or 'donor DNA'. Generally, the term 'carrier DNA' is used when the ssODN only functions to increase editing efficiency, whereas the term 'donor DNA' is used when the ssODN functions as a template for homology derived repair (HDR) and simultaneously increases editing efficiency.

Integration of single-stranded DNA can occur when microhomology is present in the flanking sequences of the DSB. This form of integration is achieved through the alt-NHEJ pathway, also known as microhomology-mediated end-joining (MMEJ). During this process, limited end resection occurs which forms the template for microhomology. If a single-stranded DNA molecule is present that has microhomology to the double-strand break flanking sequence, it can lead to integration.

The ribonucleoprotein complex (RNP) can be delivered to cells using different transfection methods. Cell-penetrating peptide delivery of Cas9 protein and guide RNA results in relatively efficient genome editing with low off-target effects (see Ramakrishna). Lipofection of the RNP relies on complexation of the RNP with cationic lipids, and has the potential to reach high levels of editing efficiency (see Yu et al., Biotechnol Lett (2016) 38:919-929). The methodology is straight-forward, but has a number of disadvantages. First, cationic lipids can be toxic to cells when administered at high concentrations. Second, many cell types, including primary human cells which have the greatest interest for medical application, cannot be transfected using traditional cationic lipids. Third, the size and polarity of both Cas9 and Cpf1 lead to complexation issues as the cationic lipids do not bind well to the cationic regions of the proteins. An alternative to lipofection is electroporation. The RNP is delivered into the cell by diffusion after pores in the cell membrane are created by applying a cell-specific current. High levels of genome editing can be achieved, but require relative high concentrations of RNP. The electroporation methodology is recommended for hard-to-transfect cell lines and primary cells.

Since the amount of RNP that gets into cells is dependent on the RNP concentrations outside of the cells, sometimes requiring a large amount of this expensive compound, methods of enhancing the efficiency of the transfection are highly desirable. The present invention provides such a composition and methods of use. These and other advantages of the invention, as well as additional inventive features, will be apparent from the description of the invention provided herein.

BRIEF SUMMARY OF THE INVENTION

The invention provides compositions and use of single-stranded carrier DNA to improve the efficiency of genome editing that results when RNP is delivered into cells through electroporation. CRISPR/Cas9-related carrier DNA has been designed to optimize genome editing efficiency. Different DNA sequences are optimal to improve CRISPR/Cas9 editing than are optimal to improve CRISPR/Cpf1 editing. CRISPR/Cpf1-related carrier DNA has been designed, the Cpf1-related carrier DNA comprising a hairpin containing a double-stranded 5'TTN or 5'TTTN PAM-site. The synthetic single-stranded DNA can be integrated into the double-stranded break site that results from Cas9 or Cpf1 cleavage of genomic DNA. Chemical modifications of the carrier DNA results in lower levels of integration at double-stranded breaks.

In a first aspect, a carrier oligonucleotide to improve transfection of ribonucleoprotein (RNP) into one or more cells in a sample is provided. The carrier oligonucleotide includes a single-stranded sequence not homologous to a cell sequence in a genome of the cell, wherein the carrier oligonucleotide is a length greater than 20 nucleotides.

In a second aspect, a carrier oligonucleotide to improve transfection of Cpf1 ribonucleoprotein (RNP) into one or more cells in a sample is provided. The carrier oligonucleotide includes a single-stranded oligonucleotide optionally containing a hairpin. The carrier oligonucleotide is not homologous to a cell sequence in a genome of the cell, wherein the carrier oligonucleotide is a length is greater than 20 nucleotides.

In a third aspect, a method of improving transfection of a ribonucleoprotein into a cell of a sample is provided. The method includes a step of contacting the cell of the sample with composition having a carrier oligonucleotide comprising a single-stranded sequence not homologous to a cell sequence in a genome of the cell, wherein the carrier oligonucleotide is a length greater than 20 nucleotides.

BRIEF DESCRIPTION OF THE DRAWINGS

FIG. 6A illustrates an analysis of cell toxicity as a function of carrier DNA concentration for Cpf1 CAR 2-16. Cell culture images were taken at 40 hours post-Nucleofection.

FIG. 6B illustrates an analysis of cell toxicity as a function of carrier DNA concentration for Cpf1 CAR 2-16 Middle. Cell culture images were taken at 40 hours post-Nucleofection.

FIG. 6C depicts editing efficiency of Cpf1 as a function of the concentrations of Cpf1 CAR 2-16 (triangles, dashed line) and Cpf1 CAR 2-16 Middle (circles, solid line) carrier concentrations.

DETAILED DESCRIPTION OF THE INVENTION

Figure 1:
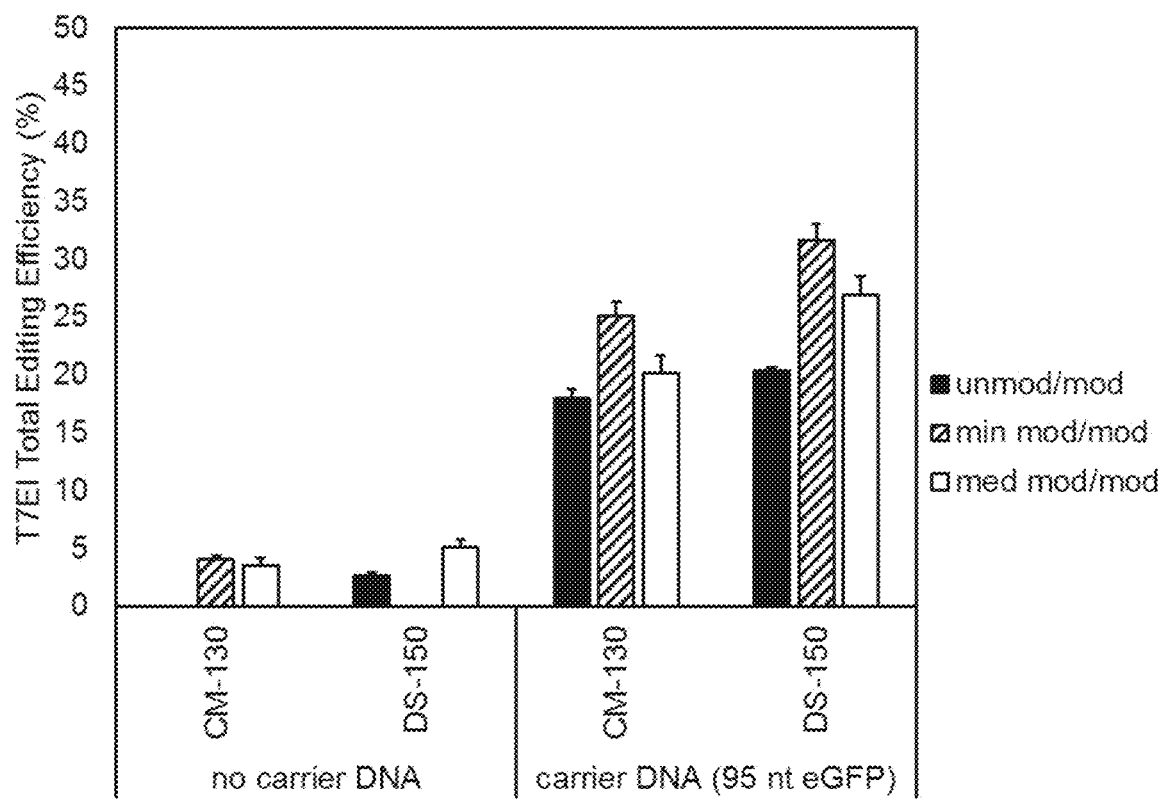
FIG. 1 illustrates the effect of Nucleofection Program or electroporation parameters and carrier DNA on editing efficiency. HEK293 cells were electroporated with a Cas9-based RNP complex with and without carrier DNA, while testing two different electroporation programs (CM130 and DS150) as well as different chemical modifications of the guide RNA ('unmod/mod', 'min mod/mod', and 'med mod/mod'). After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.

The present invention pertains to increasing the level of genome editing via electroporation of RNP complexes by the addition of single-stranded DNA oligonucleotides, also known as carrier DNA or donor DNA. The efficiency of genome editing following electroporation of the RNP complex varies with dose, with a low dose of RNP resulting in a smaller fraction of cells having genomic DNA alterations than is achieved using a high dose of RNP. The present invention relates to use of non-specific single-stranded carrier DNA to improve entry of the RNP into cells during electroporation, thereby achieving higher levels of genome editing using relatively lower doses of RNP. Given that the RNP complex is costly, methods to enable editing using lower doses of RNP to achieve high levels of editing have obvious and immediate utility. Furthermore, lowering the amount of RNP is likely to have a beneficial effect on the health of the transfected cell population.

The carrier DNA can enhance the electroporation of Cas9/RNP resulting in improved editing efficiency and this effect is dependent on the sequence and length of the carrier, with some sequences and lengths working better than others. The carrier DNA can be optimized for efficient Cpf1/RNP delivery as well, and different sequences show optimal benefit for Cas9 vs. Cpf1. The current understanding in the art is that carrier DNA is not necessary or helpful when performing Cpf1 genome editing.

One factor in the design of the carrier DNAs to optimize the ability of carrier DNA to enhance transfection of Cpf1/RNP is the presence of a Cpf1 PAM domain in the carrier nucleic acid. The PAM domain is most efficacious if present in double-stranded form, which can be achieved though annealing of complementary DNA strands or via hairpin formation of a single nucleic acid species. Cpf1 is known to bind to PAM sequences, 5'-TTN, 5'-TTTN, or 5'-TTTV, depending on the species of origin. It has also been shown, both by function and by structure (see Gao et al., Cell Res. (2016) 26(8):901-13 and Yamano et al., Cell. (2016) 165 (4):949-62), that the PAM sequences need to be double stranded in order for the Cpf1 PAM-binding domain to recognize and bind to a PAM site. Hairpin structures, rather than fully double stranded sequences, avoid potential toxicity seen with transfection of long double stranded DNA (see Nakamura et al., Int J Inflam. (2012) ID 504128) and also reduces risk of insertion of the carrier DNA strand into the double-stranded DNA cut site that results from Cpf1 action. Single-stranded DNA is less likely to be inserted into double-stranded breaks compared to double-stranded DNA. However, single-stranded carrier DNA can contribute to the final altered genomic DNA that results from genome editing. Introducing chemical modifications to the 'carrier DNA reduces the incidence of altering the genomic DNA through integration of carrier DNA-derived sequences.

Applications

In a first aspect, a carrier oligonucleotide to improve transfection of ribonucleoprotein (RNP) into one or more cells in a sample is provided. The carrier oligonucleotide includes a single-stranded sequence not homologous to a cell sequence in a genome of the cell. The carrier oligonucleotide preferably is a length greater than 20 nucleotides.

In a first respect, the concentration of the carrier oligonucleotide introduced to the sample is at least 1 µM. In a second respect, the carrier oligonucleotide comprises SEQ ID No. 4.

In a second aspect, a carrier oligonucleotide to improve transfection of Cpf1 ribonucleoprotein (RNP) into one or more cells in a sample is provided. The carrier oligonucleotide includes a single-stranded oligonucleotide optionally containing a hairpin. The carrier oligonucleotide is not homologous to a cell sequence in a genome of the cell. The carrier oligonucleotide preferably is a length is greater than 20 nucleotides.

In a first respect, the carrier oligonucleotide is a length of 60 to 150 nucleotides. In a second respect, the carrier oligonucleotide preferably is a length of 100 to 125 nucleotides. In a third respect, the carrier oligonucleotide preferably is a length of at least 112 nucleotides. In additional preferred embodiments of the foregoing respects, the carrier oligonucleotide further comprises at least three abasic spacers. Exemplary abasic spacers include those selected from the group consisting of C3, S9, or dSpacer. In a fourth respect, the carrier oligonucleotide preferably includes SEQ ID No. 9 or SEQ ID No. 25. In a fifth respect, the carrier oligonucleotide preferably includes SEQ ID No. 9. In a sixth respect, the carrier oligonucleotide preferably includes SEQ ID No. 25.

In a third aspect, a method of improving transfection of a ribonucleoprotein into a cell of a sample is provided. The method includes a step of contacting the cell of the sample with composition having a carrier oligonucleotide that includes a single-stranded sequence not homologous to a cell sequence in a genome of the cell. The carrier oligonucleotide preferably is a length greater than 20 nucleotides.

In a first respect, the carrier oligonucleotide preferably has a concentration in the composition is at least 1 µM. In a second respect, the carrier oligonucleotide preferably includes SEQ ID No. 4.

In a third respect the ribonucleoprotein includes a Cpf1 ribonucleoprotein. In a first embodiment of this respect, the carrier oligonucleotide preferably is a length of 60 to 150 nucleotides. In a second embodiment of this respect, the carrier oligonucleotide preferably is a length of 100 to 125 nucleotides. In a third embodiment of this respect, the carrier oligonucleotide preferably is a length of at least 112 nucleotides. In additional preferred embodiments, the carrier oligonucleotide further comprises at least three abasic spacers. Exemplary abasic spacers include those selected from the group consisting of C3, S9, or dSpacer. In a fifth embodiment of this respect, the carrier oligonucleotide includes SEQ ID No. 9 or SEQ ID No. 25. In a sixth embodiment of this respect, the carrier oligonucleotide preferably includes SEQ ID No. 9. In a seventh embodiment of this respect, the carrier oligonucleotide preferably includes SEQ ID No. 25.

The following examples further illustrate the invention but, of course, should not be construed as in any way limiting its scope.

EXAMPLE 1

This example demonstrates the increased efficiency of genome editing when using Cas9 as a RNP with carrier DNA.

A listing of sequences used for this Example is presented in Table 1. The level of genome editing, or editing efficiency, can be measured by a T7 endonuclease I assay (see Mean et al., BioTechniques (2004) 36:758-760), which determines the amount of edited alleles over non-edited alleles. HEK293 cells were transfected with RNP complexes in the presence or absence of carrier DNA (FIG. 1). Different chemical modifications of the guide RNA complex were tested at the same time, named 'unmod/mod', 'min mod/mod', and 'med mod/mod', as well as different electroporation parameters, named CM130 and DS150. These initial results show that the presence of carrier DNA increases the editing efficiency by 4-6-fold.

Figure 2:
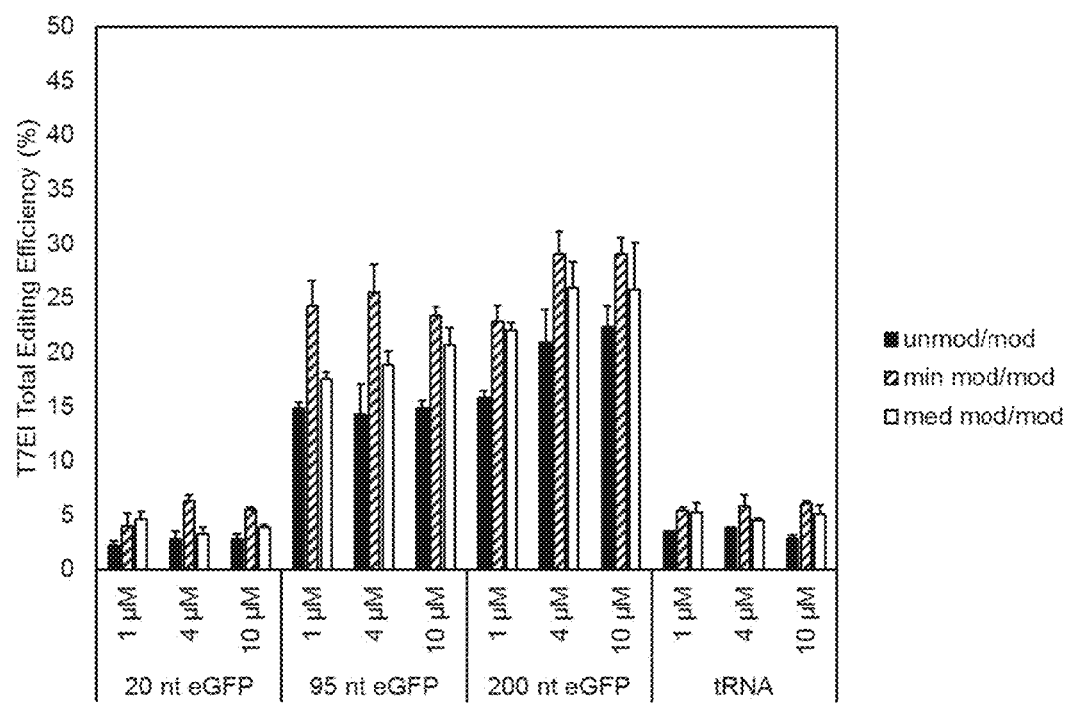
FIG. 2 illustrates the effect of carrier DNA characteristics on editing efficiency. Editing efficiency was determined in HEK293 cells electroporated with a Cas9-based RNP as well as carrier DNA of different length (20, 95, 200 nucleotides), concentration (1, 4, 10 μM), and chemistry (deoxyribonucleotide vs the ribonucleotide tRNA). After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.
Figure 3:
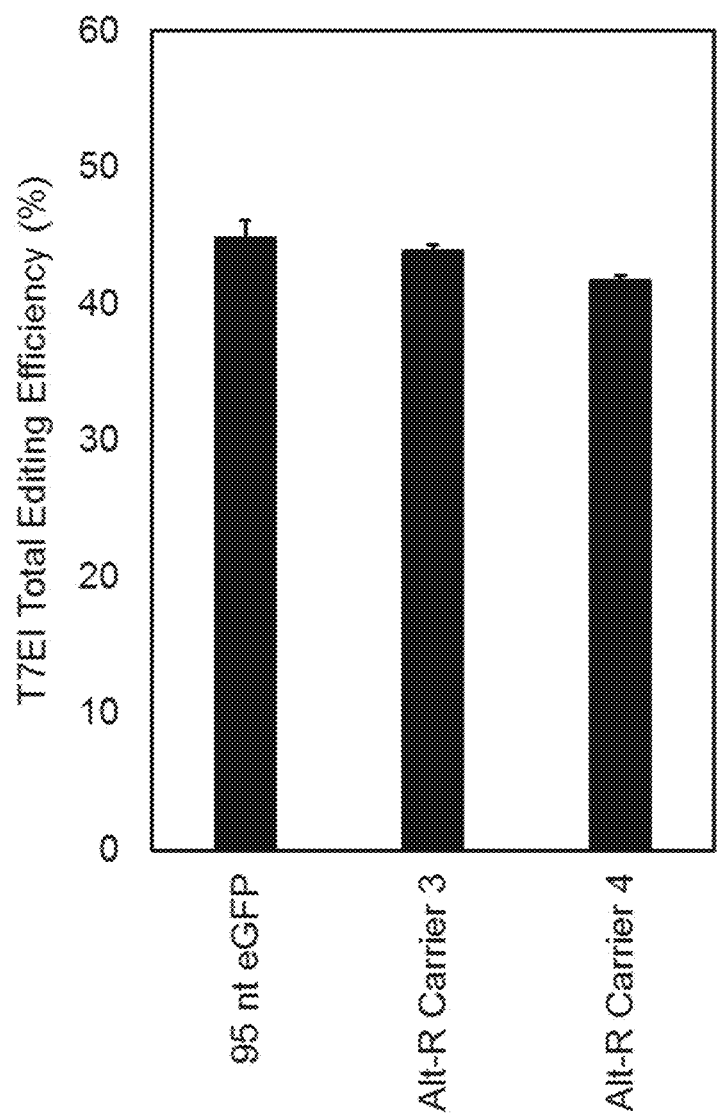
FIG. 3 illustrates the effect of different carrier DNA designs on editing efficiency. Editing efficiency was determined in HEK293 cells electroporated with a Cas9-based RNP as well as carrier DNA. After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.

For the initial results (FIG. 1), the carrier DNA was a single-stranded oligodeoxyribonucleotide with a length of 95 nucleotides based on a green fluorescent protein (eGFP) sequence (SEQ ID No. 1). This sequence was chosen as it does not share any homology with the human HEK293 cell line. To further investigate the necessary characteristics of the carrier DNA, the following parameters were tested: length (20 nt (SEQ ID No. 2), 95 nt (SEQ ID No. 1), 200 nt (SEQ ID No. 3)), concentration (1, 4 and 10 µM), and chemistry (deoxyribonucleotides, ribonucleotides). Additionally, different chemical modifications of the guide RNA (annealed crRNA:tracrRNA) were tested ('unmod/mod', 'min mod/mod', and 'med mod/mod'). FIG. 2 shows a positive correlation between editing efficiency and length of the carrier DNA. The concentrations in the tested range did not show a strong correlation with editing efficiency. No benefit was observed when ribonucleotides (tRNA) were used. In conclusion, optimal editing efficiency was obtained when using a single-stranded deoxyribonucleotide with a length of more than 20 nucleotides and a concentration of at least 1 µM. To further test sequence specificity, two 'carrier DNAs' were tested having different sequences. FIG. 3 shows the editing efficiency obtained when 'Alt-R carrier 3' (SEQ ID No. 4) and 'Alt-R carrier 4' (SEQ ID No. 5) were used as carrier DNA. The sequence of 'Alt-R carrier 3' and 'Alt-R carrier 4' has no homology with the human, mouse, or rat genomes. The length of 'Alt-R carrier 3' and 'Alt-R carrier 4' are both 100 nucleotides. These results show that editing efficiency is influenced by sequence, as differences in editing efficiency are observed between the 3 tested 'carrier DNAs' in FIG. 3. In conclusion, carrier DNA can enhance the efficiency of genome editing when electroporation of Cas9/RNP is employed and that this effect is dependent on the sequence, chemistry and length of the carrier DNA, with some sequences, chemistries and lengths showing greater effect than others.

HEK293 cells were electroporated using the Amaxa Nucleofector System (Lonza). After harvesting the cells using trypsinization and subsequent neutralization of the trypsin by addition of growth media containing 10% Fetal Bovine Serum (FBS), cells were counted and pelleted using centrifugation (200 rpm, 10 minutes at room temperature). The pelleted cells were washed with one volume of at least 5 mL 1× phosphate-buffered saline (PBS). The cells were then pelleted and resuspended in Nucleofection Solution SF at a concentration of 2.5E7 cells/mL. The guide RNA complex was formed by hybridization of equal molar amounts of crRNA and tracrRNA at a final concentration of 40 µM in IDTE. The crRNA was specific to the HPRT gene at position 38285-AS (Table 8: SEQ ID No. 67). The ribonucleoprotein complex (RNP) was generated by complexation of 100 pmol Cas9 protein with 120 pmol guide RNA complex in a total volume of 10 µL. Cas9 buffer was used to adjust to the final volume. Following mixing, complexes were formed by incubation of the RNP for 10-20 minutes at room temperature. For each electroporation, 10 µL of RNP complex was added to 20 µL of HEK293 cells in Nucleofection Solution SF (5E5 cells). Additionally, 1 µL of carrier DNA, diluted in IDTE, was added to achieve its desired final concentration. 25 µL out of 31 µL of the solution was mixed by pipetting up and down and transferred to an electroporation cuvette. The cells were electroporated according to the manufacturer's protocol using the Amaxa 96-well Shuttle device and Nucleofection settings 96-CM-120 or 96-DS-150. After electroporation, the cells were resuspended with 75 µL pre-warmed culture media in the electroporation cuvette. Triplicate aliquots of 25 µL of resuspended cells were further cultured in 175 µL pre-warmed media each. Genomic DNA was isolated after the cells were incubated for 48 hours at 37° C. containing 5% $CO_2$. The targeted genomic locus was amplified using PCR (Table 9: SEQ ID Nos. 81 and 82) Heteroduplexes were formed by denaturing the amplicons followed by a slow cool-down. Mismatches in heteroduplexes were cleaved by T7 Endonuclease I, and cleaved and non-cleaved products were quantified using a Fragment Analyzer.

ssDNA added to the CRISPR gene editing mix can lead to genome alterations via HDR mechanisms. For the carrier DNA to function solely to enhance transfection efficiency without altering the outcome of the genome editing products obtained it is preferred that the carrier DNA have no homology to the genome of the cell being transfected and edited. While there are many artificial sequences which could be used in this setting that have no homology to the target cell genome, SEQ ID No. 4 has been used successfully in present experiments and is usable in human, mouse, and rat cells.

TABLE 1

List of sequences employed in Example 1.

| SEQ ID No. | Sequence |
| --- | --- |
| SEQ ID No. 1: 95 nt eGFP | CCAGCAGAACACCCCCATCGGCGACGGCCCCGTGCTGCTGCCCGACAACCACTACCTGAGCA CCCAGTCCGCCCTGAGCAAAGACCCCAACGAGA |
| SEQ ID No. 2: 20 nt eGFP | CCAGCAGAACACCCCCATCG |
| SEQ ID No. 3: 200 nt eGFP | AGGACGGCAGCGTGCAGCTCGCCGACCACTACCAGCAGAACACCCCCATCGGCGACGGCCC CGTGCTGCTGCCCGACAACCACTACCTGAGCACCCAGTCCGCCCTGAGCAAAGACCCCAACG AGAAGCGCGATCACATGGTCCTGCTGGAGTTCGTGACCGCCGCCGGGATCACTCTCGGCATG GACGAGCTGTACAAG |
| SEQ ID No. 4: Alt-R Carrier 3 | TTAGCTCTGTTTACGTCCCAGCGGGCATGAGAGTAACAAGAGGGTGTGGTAATATTACGGTA CCGAGCACTATCGATACAATATGTGTCATACGGACACG |
| SEQ ID No. 5: Alt-R Carrier 4 | GTCCCAGCGGGCATGAGAGTAACAAGAGGGTGTGGTAATATTACGGTACCGAGCACTATCG ATACAATATGTGTCATACGGACACGTAACTGACATACAG |

EXAMPLE 2

The following example demonstrates the effect of different carrier DNA sequences on editing efficiency when transfecting RNP in a CRISPR/Cpf1 system.

Example 1 demonstrated that carrier DNA can enhance the efficiency of genome editing achieved using Cas9/RNP in mammalian cells and further demonstrated that this effect is influenced by the sequence, chemistry and length of the carrier DNA. The present example demonstrates optimization of sequences to use in the CRISPR/Cpf1 system.

Cpf1 is known to bind to PAM sequences, 5'-TTN, 5'-TTTN, or 5'-TTTV depending on the species of origin. It has also been shown, both by function (see Zetsche et al., Cell. (2015) 163(3):759-71) and by structure (see Gao et al., Cell Res. (2016) 26(8):901-13, and Yamano et al., Cell. (2016) 165(4):949-62), that the PAM sequences need to be double stranded in order for the Cpf1 PAM-binding domain to recognize and bind to a PAM site. Cpf1-specific carrier DNA designs were tested that included a double-stranded feature in the form of a hairpin structure.

Figure 4:
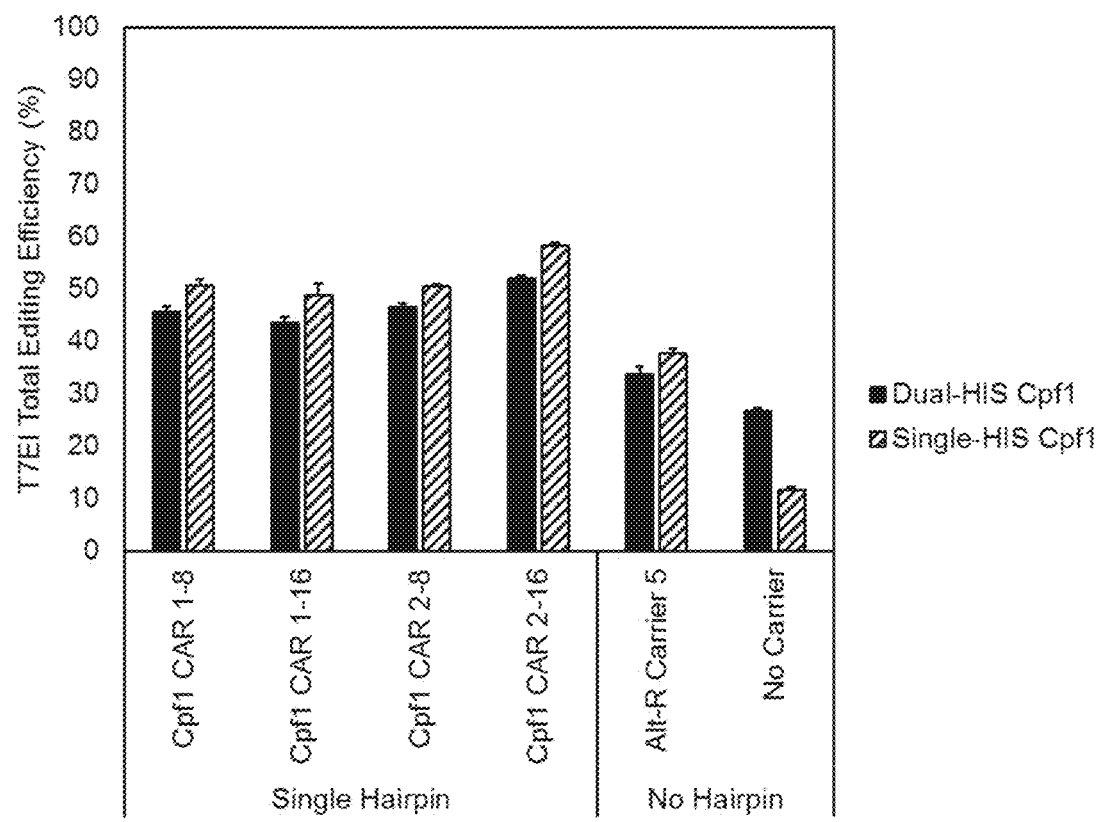
FIG. 4 illustrates the effect of different carrier DNA designs on editing efficiency. Editing efficiency was determined in HEK293 cells electroporated with a Cpf1-based RNP as well as carrier DNA. Solid and striped bars represent Cpf1 protein containing two or one HIS-tags, respectively. After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.

Editing efficiency was determined in HEK293 cells which were transfected with RNP complexes in the presence or absence of carrier DNA (FIG. 4). Different carrier DNA designs were tested that contain a hairpin structure with a length of 8 or 16 base pairs and with different sequences. Also, these hairpin-containing designs were compared to a carrier DNA without a hairpin design, but containing TTTN PAM motifs. These results show that the presence of carrier DNA results in an increase in editing efficiency, and that including a hairpin structure in the carrier DNA improves results.

HEK293 cells were electroporated (3.5E5 cells/DS-150 protocol) with RNP complex with different carrier constructs. The ratio of Cpf1:crRNA molar ratio was 1:1.2. and RNP concentration was 5 µM. Carrier constructs used were the hairpin designs Cpf1 CAR 1-8 (SEQ ID No. 6), Cpf1 CAR 1-16 (SEQ ID No. 7), Cpf1 CAR 2-8 (SEQ ID No. 8), Cpf1 CAR 2-16 (SEQ ID No. 9), and the non-hairpin Alt-R Carrier 5 (SEQ ID No. 10), as well as a no carrier control. The crRNA was specific to the HPRT gene at position 38104-S (Table 8: SEQ ID No. 68). The results are illustrated in FIG. 4. Solid black and striped bars represent Cpf1 protein containing two or one His-tags, respectively. After a 48 hour post-Nucleofection incubation, the genomic DNA was isolated, the target region amplified by PCR (Table 9: SEQ ID Nos. 81 and 82), digested with 2 U T7EI endonuclease, then the percent editing was determined via a fragment analyzer run. Table 2 lists the sequences tested in this example.

presence of phosphorothioate bonds in the carrier DNA, and presence of 2'-O-methyl modifications in the carrier DNA.

Figure 5A:
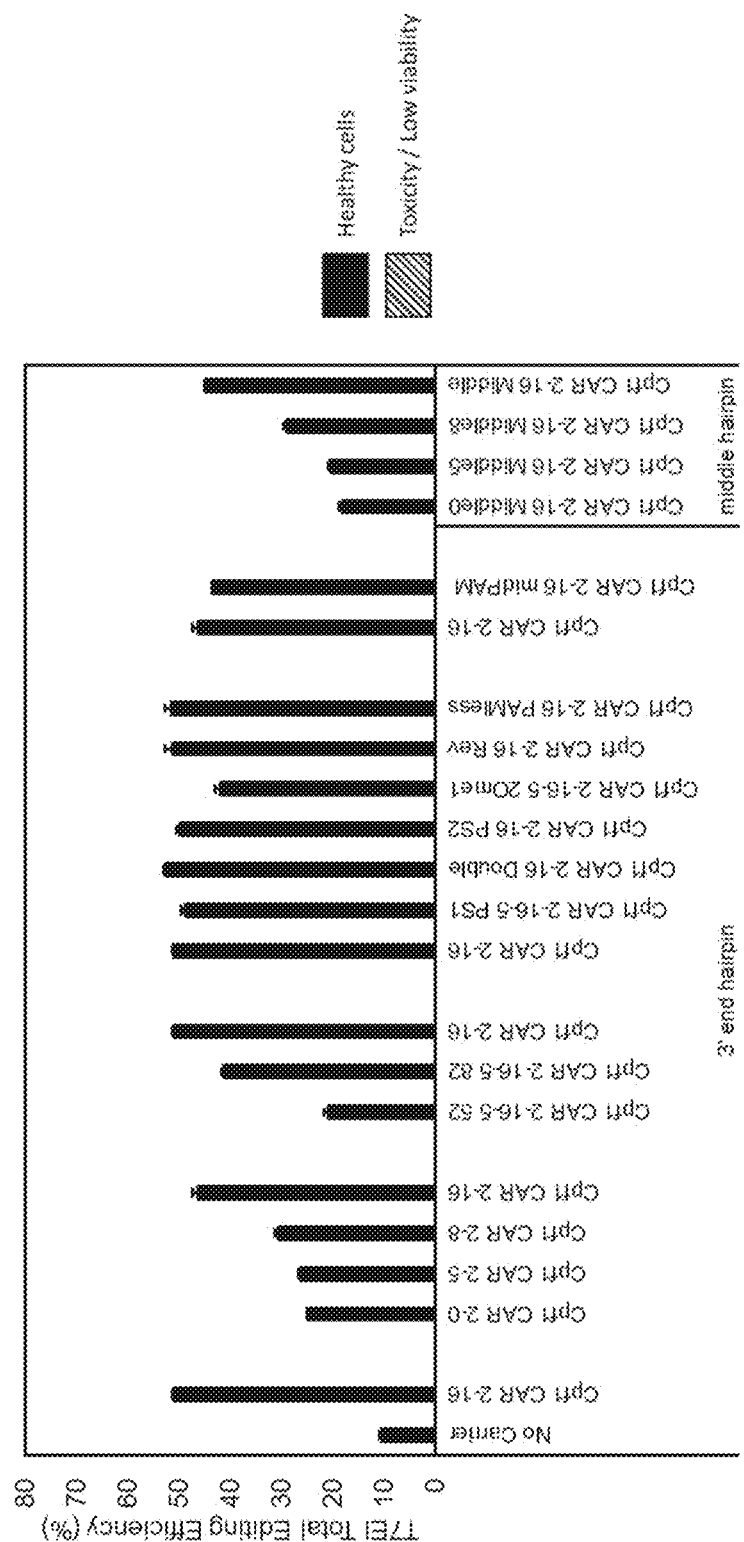
FIG. 5A shows the comparison of the editing efficiencies and cell toxicities for different Cpf1 carrier DNA designs containing either a hairpin structure at the 3' end or in the middle part of the carrier DNA. Editing efficiency was determined in HEK293 cells electroporated with a Cpf1-based RNP as well as different carrier DNA designs. After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.
Figure 5B:
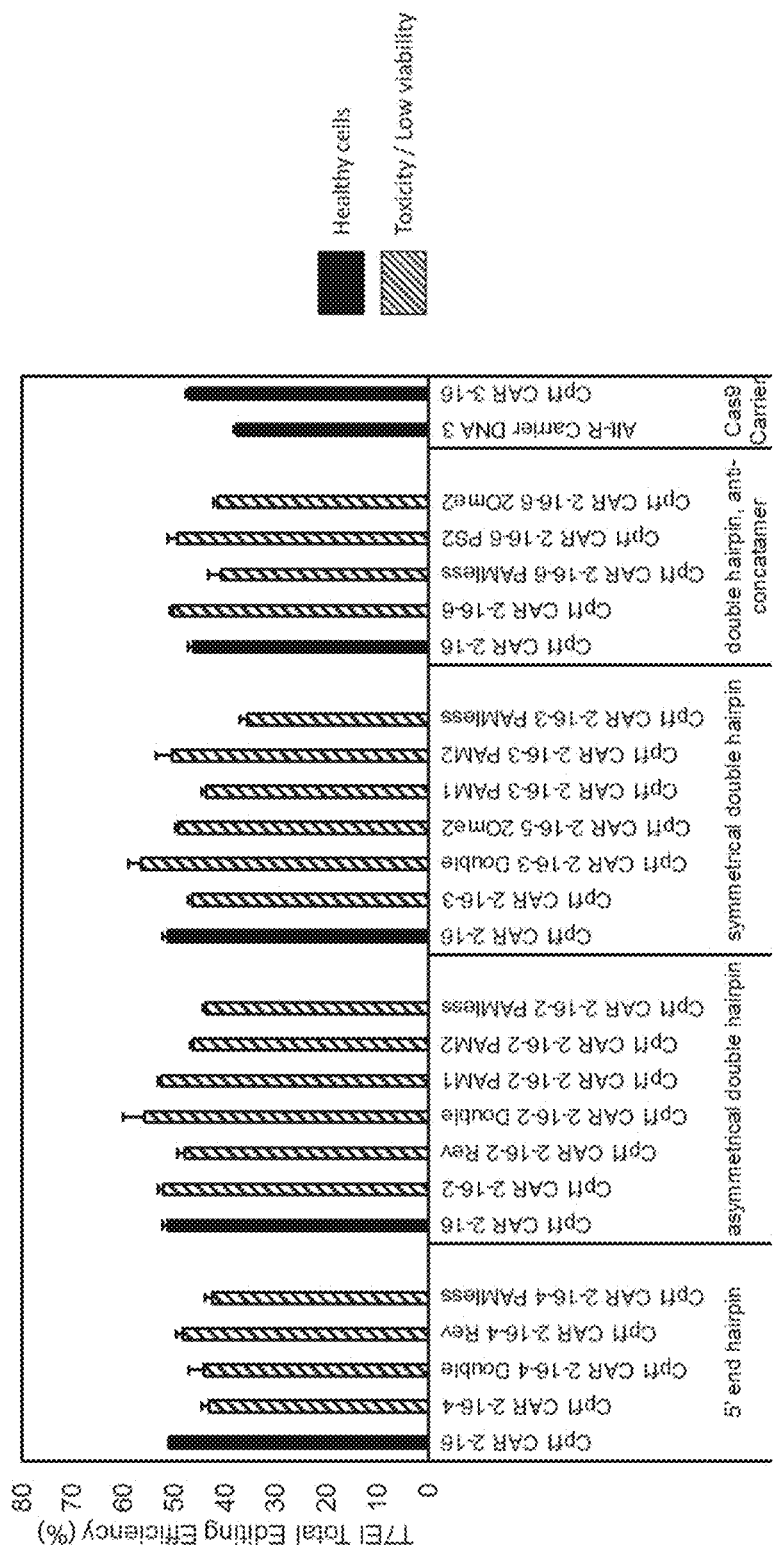
FIG. 5B shows the comparison of the editing efficiencies and cell toxicities for different carrier DNA designs containing either a hairpin structure at the 5' end, on both ends (asymmetrical and symmetrical), or on both ends of the carrier DNA in a fashion to prevent concatemerization. For each set of designs, Cpf1 CAR 2-16 (SEQ ID No. 9) was included as reference. Solid bars represent healthy cell cultures, whereas cell cultures that displayed cell toxicity or low viability are represented by diagonally striped bars. Experimental details and analyses are as presented in the legend to FIG. 5A.

HEK293 cells were electroporated (3.5E5 cells/DS-150 protocol) with RNP complex with different carrier DNA designs. The molar ratio of Cpf1:crRNA was 1:1.2 and RNP concentration was 5 µM. Carrier DNA concentrations were at 5 µM. The crRNA targets the HPRT gene at position 38104-S (Table 8: SEQ ID No. 68). After a 48 hour post-electroporation incubation, the genomic DNA was isolated, the target region amplified by PCR (Table 9: SEQ ID Nos. 81 and 82), digested with 2 U T7EI endonuclease, then the percent editing was measured by capillary electrophoresis using a Fragment Analyzer. Cell toxicity was assessed by visual inspection of the cell cultures 40 hours post transfection. FIG. 5A shows the comparison of the editing efficiencies and cell toxicities for the 3' single hairpin (SEQ ID Nos. 12-21) and middle hairpin (SEQ ID Nos. 23-25) designs and their corresponding no hairpin control constructs (SEQ ID Nos. 11 and 22). Healthy cell cultures are represented by solid bars, whereas cell cultures that displayed cell toxicity or low viability are represented by diagonally striped bars. FIG. 5B shows the comparison of the editing efficiencies and cell toxicities for the 5' single hairpin (SEQ ID Nos 26-29), asymmetrical double hairpin (SEQ ID Nos. 30-35), symmetrical double hairpin (SEQ ID Nos. 36-41), anti-concatemer double hairpin (SEQ ID Nos. 42-45), and Cas9 carrier (SEQ ID No. 46) designs. Solid bars represent healthy cell cultures, whereas cell cultures that displayed cell toxicity or low viability are represented

TABLE 2

List of sequences tested in Example 2.

| SEQ ID No. | Sequence |
|---|---|
| SEQ ID No. 6:<br>Cpf1 CAR 1-8 | CCCAGCGGGCATGAGAGTAACAAGAGGGTGTGGTAATATTACGGTACCGAGCACT<br>ATCGATACAATATGTGTCATACGGACACGGAAACATGTAATCATGTTTC |
| SEQ ID No. 7:<br>Cpf1 CAR 1-16 | CCCAGCGGGCATGAGAGTAACAAGAGGGTGTGGTAATATTACGGTACCGAGCACT<br>ATCGATACAATATGTGTCATAGAAACATGCGTGTCCGTAATCGGACACGCATGTTTC |
| SEQ ID No. 8:<br>Cpf1 CAR 2-8 | TGGATAATAATGAACGCATTAGATAGATTTGAATGCCGGAACTTTGGATTTAGATCA<br>CCCATTGACTTGGTCAACGATAGCGAAGAAACATGTAATCATGTTTC |
| SEQ ID No. 9:<br>Cpf1 CAR 2-16 | TGGATAATAATGAACGCATTAGATAGATTTGAATGCCGGAACTTTGGATTTAGATCA<br>CCCATTGACTTGGTCAACGGAAACATGTTCGCTATTAATATAGCGAACATGTTTC |
| SEQ ID No. 10:<br>Alt-R Carrier 5 | TTAGCTCTGTTTACGTCCCAGCGGGCATGAGAGTAACAAGAGGGTGTGGTAATATT<br>TCGGTACCGAGCACTTTCGATACAATATGTTTCATACGGACACG |

EXAMPLE 3

The following example demonstrates the effect of Cpf1' carrier DNA' sequence on editing efficiency and cell toxicity.

Figure 5C:
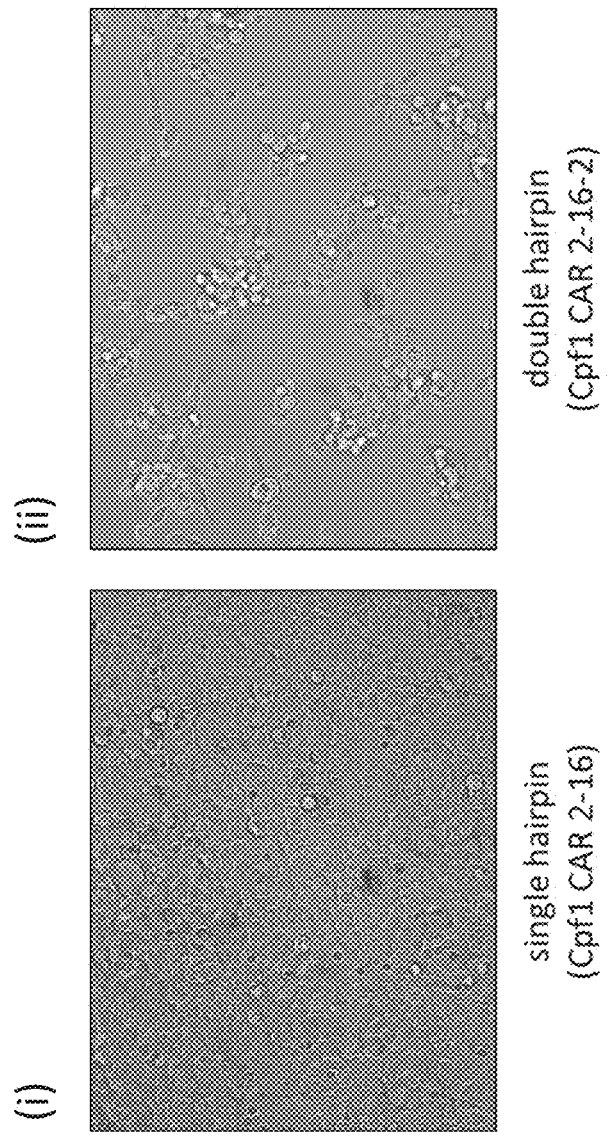
FIG. 5C shows representative cell culture images of healthy cells (single hairpin (panel (i))) versus cells displaying toxicity and low viability (double hairpin (panel (ii))). Experimental details and analyses are as presented in the legend to FIGS. 5A and 5B.

Table 3 shows representative sequences for the main classes of carrier DNA designs tested, which were based on the location of the hairpin structure in the carrier DNA: no hairpin (SEQ ID Nos. 11 and 22), 3' single hairpin (SEQ ID Nos. 12-21), middle hairpin (SEQ ID Nos. 23-25), 5' single hairpin (SEQ ID Nos 26-29), asymmetrical double hairpin (SEQ ID Nos. 30-35), symmetrical double hairpin (SEQ ID Nos. 36-41), anti-concatemer double hairpin (SEQ ID Nos. 42-45), and a version of the Cas9 carrier 3 (SEQ ID No. 4) with an additional 3' hairpin sequence (SEQ ID No. 46). Within these groups, different features were tested, such as hairpin length, total length, number of PAM sites in the hairpin structure, location of PAM sites in the hairpin structure, orientation of PAM sites in the hairpin structure, by diagonally striped bars. FIG. 5C shows examples of a healthy cell culture (left panel, single hairpin (Cpf1 CAR 2-16, SEQ ID No. 9)), and of a cell culture affected by toxicity and low viability (right panel, double hairpin (Cpf1 CAR 2-16-2, SEQ ID No. 30)).

FIG. 5A shows the editing efficiencies of the carrier DNA designs with a 3' hairpin. For the designs with the 3' hairpin, a number of features were tested to determine the effect on editing efficiency: 1) shortening the hairpin length reduces editing efficiency. Cpf1 CAR 2-0 (SEQ ID No. 11) does not have a hairpin structure, and results in 24.9% editing. Cpf1 CAR 2-5 has a hairpin length of 5 base pairs (SEQ ID No. 12), and results in 26.1% editing. Cpf1 CAR 2-8 (SEQ ID No. 8) has a hairpin length of 8 base pairs, and results in 30.5% editing. Cpf1 CAR 2-16 (SEQ ID No. 9) has a hairpin length of 16 base pairs, and results in 46.1% editing. 2) Shortening the carrier DNA while keeping the hairpin structure constant at 16 base pairs leads to a reduction of editing efficiency. Cpf1 CAR 2-16-5 52 (SEQ ID No. 13) has a total length of 52 nucleotides, and results in 20.7% editing. Cpf1 CAR 2-16-5 82 (SEQ ID No. 14) has a length of 82 nucleotides, and results in 41.2% editing. Cpf1 CAR 2-16 (SEQ ID No. 9) has a length of 112 nucleotides, and results in 51.0% editing. 3) Introduction of phosphorothioate linkages, two PAM sites in the hairpin structure, 2'-O-methyl modifications in the carrier DNA, or orientation of the PAM site in the hairpin structure did not lead to an increase in editing efficiency. Cpf1 CAR 2-16-5 PS1 (SEQ ID No. 15) has 3 phosphorothioate linkages at the 5' and 3' end, and results in 48.7% editing. Cpf1 CAR 2-16 Double (SEQ ID No. 16) has two PAM sites in the hairpin structure, and results in 52.7% editing. Cpf1 CAR 2-16 PS2 (SEQ ID No. 17) has 3 phosphorotioate linkages at the 5' and 3' end, as well as two PAM sites in the hairpin structure, and results in 49.8% editing. Cpf1 CAR 2-16-5 2Ome1 (SEQ ID No. 18) has 2'-O-methyl modified Uridine nucleotides in the loop region of the hairpin structure, and results in 41.8% editing. Cpf1 CAR 2-16 Rev (SEQ ID No. 19) has the orientation of the PAM site switched, and results in 51.2% editing. Cpf1 CAR 2-16 PAMless (SEQ ID No. 20) lacks a PAM site in the hairpin structure, and results in 51.4% editing. Cpf1 CAR 2-16 midPAM (SEQ ID No. 21) has the PAM site located in the middle of the hybridized section of the hairpin structure, and results in 43.4% editing. None of the designs with a 3' hairpin led to toxicity.

FIG. 5A also shows the editing efficiencies of the carrier DNA designs with a hairpin structure in the middle of the carrier DNA sequence. For these designs, only the effect of the length of the hairpin structure on editing efficiency was determined. Shortening of the hairpin length reduced editing efficiency. Cpf1 CAR 2-16 Middle0 (SEQ ID No. 22) does not have a hairpin structure, and results in 18.0% editing. Cpf1 CAR 2-16 Middle5 has a hairpin length of 5 base pairs (SEQ ID No. 23), and results in 20.4% editing. Cpf1 CAR 2-16 Middle8 (SEQ ID No. 24) has a hairpin length of 8 base pairs, and results in 29.0% editing. Cpf1 CAR 2-16 Middle (SEQ ID No. 25) has a hairpin length of 16 base pairs, and results in 44.8% editing. None of the designs with a hairpin design in the middle of the carrier DNA sequence led to toxicity.

FIG. 5B shows the editing efficiencies of the carrier DNA with a 5' hairpin structure. Cpf1 CAR 2-16-4 (SEQ ID No. 26) has a hairpin structure on the 5' end, and results in 43.0% editing. Furthermore, for the designs with the 5' hairpin, a number of features were tested to determine the effect on editing efficiency. Cpf1 CAR 2-16-4 Double (SEQ ID No. 27) contains two PAM sites in the hairpin structure, and leads to 44.1% editing. Cpf1 CAR 2-16-4 Rev (SEQ ID No. 28) has the orientation of the PAM site switched, and results in 48.4% editing. Cpf1 CAR 2-16-4 PAMless (SEQ ID No. 29) lacks a PAM site in the hairpin structure, and leads to 42.5% editing. The editing efficiencies of these designs were slightly lower compared to Cpf1 CAR 2-16 (SEQ ID No. 9), which gave 51.0% editing. All the designs with a 5' hairpin structure led to toxicity and low cell viability.

FIG. 5B also shows the editing efficiencies of the carrier DNA with an asymmetrical double hairpin, where one hairpin is located on the 5' end and one hairpin is located on the 3' end. For the designs with an asymmetrical double hairpin, both hairpins have identical sequences. Cpf1 CAR 2-16-2 (SEQ ID No. 30) has an asymmetrical double hairpin structure, and results in 52.0% editing. Furthermore, for the designs with the asymmetric double hairpin, a number of features were tested to determine the effect on editing efficiency. Cpf1 CAR 2-16-2 Rev (SEQ ID No. 31) has the orientation of the PAM sites switched on both hairpins, and leads to 47.8% editing. Cpf1 CAR 2-16-2 Double (SEQ ID No. 32) has two PAM sites present on each hairpin, and result in 55.9% editing. Cpf1 CAR 2-16-2 PAM1 (SEQ ID No. 33) only has a single PAM site present on the 5' hairpin, and leads to 52.4% editing. Cpf1 CAR 2-16-2 PAM2 (SEQ ID No. 34) only has a single PAM site present on the 3' hairpin, and leads to 46.2% editing. Cpf1 CAR 2-16-2 PAMless (SEQ ID No. 35) lacks PAM sites in either of the two hairpin structures, and leads to 43.7% editing. The editing efficiencies of these designs were compared to Cpf1 CAR 2-16 (SEQ ID No. 9), which gave 51.3% editing. All the designs with an asymmetric double hairpin structure led to toxicity and low cell viability.

FIG. 5B also shows the editing efficiencies of the carrier DNA with a symmetrical double hairpin, where one hairpin is located on the 5' end and one hairpin is located on the 3' end. For the designs with an symmetrical double hairpin, the hairpin on the 5' end is the reverse sequence of the hairpin on the 3' end. Cpf1 CAR 2-16-3 (SEQ ID No. 36) has a symmetrical double hairpin structure, and results in 46.3% editing. Furthermore, for the designs with the symmetric double hairpin, a number of features were tested to determine the effect on editing efficiency. Cpf1 CAR 2-16-3 Double (SEQ ID No. 37) has two PAM sites present on each hairpin, and result in 56.4% editing. Cpf1 CAR 2-16-5 2Ome2 (SEQ ID No. 38) also has two PAM sites present in each hairpin, as well as having 2'-O-methyl modified Uridine nucleotides in the loop region of each of the hairpin structures, and results in 49.1% editing. Cpf1 CAR 2-16-3 PAM1 (SEQ ID No. 39) only has a single PAM site present on the 5' hairpin, and leads to 43.7% editing. Cpf1 CAR 2-16-3 PAM2 (SEQ ID No. 40) only has a single PAM site present on the 3' hairpin, and leads to 50.5% editing. Cpf1 CAR 2-16-3 PAMless (SEQ ID No. 41) lacks PAM sites in either of the two hairpin structures, and leads to 35.5% editing. The editing efficiencies of these designs were compared to Cpf1 CAR 2-16 (SEQ ID No. 9), which gave 51.3% editing. All the designs with a symmetric double hairpin structure led to toxicity and low cell viability.

FIG. 5B also shows the editing efficiencies of the carrier DNA with a double hairpin, where one hairpin is located on the 5' end and one hairpin is located on the 3' end, and where concatamerization is not possible. Cpf1 CAR 2-16-6 (SEQ ID No. 42) has an anti-concatamer double hairpin structure, and results in 50.2% editing. Furthermore, for the designs with the anti-concatamer double hairpin, a number of features were tested to determine the effect on editing efficiency. Cpf1 CAR 2-16-6 PAMless (SEQ ID No. 43) lacks PAM sites in the hairpin structures, and leads to 40.9% editing. Cpf1 CAR 2-16-6 PS2 (SEQ ID No. 44) has 3 phosphorothioate linkages at the 5' and 3' end, and results in 49.4% editing. Cpf1 CAR 2-16-6 2Ome2 (SEQ ID No. 45) has 2'-O-methyl modified Uridine nucleotides in the loop region of each of the hairpin structures, and results in 41.3% editing. The editing efficiencies of these designs were compared to Cpf1 CAR 2-16 (SEQ ID No. 9), which gave 46.1% editing. All the designs with an anti-concatamer double hairpin structure led to toxicity and low cell viability.

FIG. 5B also shows editing efficiencies of an unrelated linear carrier (Alt-R Carrier 3, SEQ ID No. 4), which leads to 37.7% editing. Introduction of a 3' hairpin to this unrelated linear carrier (Cpf1 CAR 3-16, SEQ ID No. 46) increased editing efficiency to 47.1%. These designs did not lead to toxicity.

In conclusion, FIGS. 5A and 5B show increased Cpf1 editing efficiency in the presence of carrier DNA with either a 3' hairpin or a hairpin located in the middle of the oligonucleotide. Editing efficiency is dependent on hairpin length. Reducing the hairpin from a 16-mer to either an 8-mer or a 5-mer leads to reduced editing efficiency. Additionally, absence of the hairpin leads to a further lowering of editing efficiency. When the carrier lengths are decreased to 52 or 82 nucleotides without altering the hairpin structure, the beneficial effects are lost as well. Changing the orientation of the PAM site had no effect on editing efficiency. The presence of two 5'-TTTN PAM sequences does not increase editing efficiency compared to a single 5'-TTTN sequence. Removing the 5'-TTTN PAM site does not lead to drop in efficiency, however, alternative 5' TTN sites are still present and may still enable the Cpf1 to bind well enough for it to form a complex which can be transported into the cell. Since the presence of phosphorothioate ends doesn't diminish the transfection enhancement, it could be beneficial to include these as protection against degradation. Most importantly, when additional hairpins are incorporated into the carrier at the 5' end in combination with the 3' end hairpin, or if a single hairpin is present on the 5' end, cell viability decreases, independent of the presence or absence of 5'-(T) TTN PAM sites. These structures may be triggering an immune response, as is commonly seen with transfection of double stranded DNA into mammalian cells. Addition of the hairpin structure to an unrelated linear carrier (Alt-R Carrier 3, SEQ ID No. 4) also increased editing efficiency (Cpf1 CAR 3-16, SEQ ID No. 46). Therefore, both Cpf1 CAR 2-16 (SEQ ID No. 9) and Cpf1 CAR 2-16 Middle (SEQ ID No. 25) are superior to the other designs tested, although other sequences do show benefit. A carrier DNA having a length of about 112 nucleotides was optimal in this series of studies.

TABLE 3

List of sequences tested in Example 3.

| SEQ ID No. | Sequence |
| --- | --- |
| SEQ ID No. 11:<br>Cpf1 CAR 2-0 | TGGATAATAATGAACGCATTAGATAGATTTGAATGCCGGAACTTTGGATTTAGATCACCCAT<br>TGACTTGGTCAACGATAGCGAAGAAAGTA |
| SEQ ID No. 12:<br>Cpf1 CAR 2-5 | TGGATAATAATGAACGCATTAGATAGATTTGAATGCCGGAACTTTGGATTTAGATCACCCAT<br>TGACTTGGTCAACGATAGCGAAGAAAGTAATCTTTC |
| SEQ ID No. 13:<br>Cpf1 CAR 2-16-552 | ATTGACTTGGTCAACGGAAACATGTTCGCTATTAATATAGCGAACATGTTTC |
| SEQ ID No. 14:<br>Cpf1 CAR 2-16-582 | GAATGCCGGAACTTTGGATTTAGATCACCCATTGACTTGGTCAACGGAAACATGTTCGCTAT<br>TAATATAGCGAACATGTTTC |
| SEQ ID No. 15:<br>Cpf1 CAR 2-16-5<br>PS1 | T*G*G*ATAATAATGAACGCATTAGATAGATTTGAATGCCGGAACTTTGGATTTAGATCACC<br>CATTGACTTGGTCAACGGAAACATGTTCGCTATTAATATAGCGAACATGT*T*T*C |
| SEQ ID No. 16:<br>Cpf1 CAR 2-16<br>Double | TGGATAATAATGAACGCATTAGATAGATTTGAATGCCGGAACTTTGGATTTAGATCACCCAT<br>TGACTTGGTCAACGGAAACATGAAAGCTATTAATATAGCTTTCATGTTTC |
| SEQ ID No. 17:<br>Cpf1 CAR 2-16<br>PS2 | T*G*G*ATAATAATGAACGCATTAGATAGATTTGAATGCCGGAACTTTGGATTTAGATCACC<br>CATTGACTTGGTCAACGGAAACATGAAAGCTATTAATATAGCTTTCATGT*T*T*C |
| SEQ ID No. 18:<br>Cpf1 CAR 2-16-5<br>2Ome1 | TGGATAATAATGAACGCATTAGATAGATTTGAATGCCGGAACTTTGGATTTAGATCACCCAT<br>TGACTTGGTCAACGGAAACATGAAAGCTAmUmUmAmAmUmATAGCTTTCATGTTTC |
| SEQ ID No. 19:<br>Cpf1 CAR 2-16<br>Rev | TGGATAATAATGAACGCATTAGATAGATTTGAATGCCGGAACTTTGGATTTAGATCACCCAT<br>TGACTTGGTCAACGGTTTCATGTTCGCTATTAATATAGCGAACATGAAAC |
| SEQ ID No. 20:<br>Cpf1 CAR 2-16<br>PAMless | TGGATAATAATGAACGCATTAGATAGATAAGAATGCCGGAACTAAGGATAAAGATCACCCA<br>TTGACTTGGTCAACGGGCACATGTTCGCTATTAATATAGCGAACATGTGCC |
| SEQ ID No. 21:<br>Cpf1 CAR 2-16<br>midPAM | TGGATAATAATGAACGCATTAGATAGATTTGAATGCCGGAACTTTGGATTTAGATCACCCAT<br>TGACTTGGTCAACGGCATGAAATTCGCTATTAATATAGCGAATTTCATGC |
| SEQ ID No. 22:<br>Cpf1 CAR 2-16<br>Middle0 | TGGATAATAATGAACGCATTAGATAGATTTGAATGCGAAAGTACGGAACTTTGGATTTAGAT<br>CACCCATTGACTTGGTCAACG |
| SEQ ID No. 23:<br>Cpf1 CAR 2-16<br>Middle5 | TGGATAATAATGAACGCATTAGATAGATTTGAATGCGAAAGTAATCTTTCCGGAACTTTGGA<br>TTTAGATCACCCATTGACTTGGTCAACG |
| SEQ ID No. 24:<br>Cpf1 CAR 2-16<br>Middle8 | TGGATAATAATGAACGCATTAGATAGATTTGAATGCGAAACATGTAATCATGTTTCCGGAAC<br>TTTGGATTTAGATCACCCATTGACTTGGTCAACG |
| SEQ ID No. 25:<br>Cpf1 CAR 2-16<br>Middle | TGGATAATAATGAACGCATTAGATAGATTTGAATGCGAAACATGTTCGCTATTAATATAGCG<br>AACATGTTTCCGGAACTTTGGATTTAGATCACCCATTGACTTGGTCAACG |

TABLE 3-continued

List of sequences tested in Example 3.

| SEQ ID No. | Sequence |
| --- | --- |
| SEQ ID No. 26:<br>Cpf1 CAR 2-16-4 | CTTTGTACAAGCGATATAATTATCGCTTGTACAAAGTGGATAATAATGAACGCATTAGATAG<br>ATTTGAATGCCGGAACTTTGGATTTAGATCACCCATTGACTTGGTCAACG |
| SEQ ID No. 27:<br>Cpf1 CAR 2-16-4<br>Double | CTTTGTACTTTCGATATAATTATCGAAAGTACAAAGTGGATAATAATGAACGCATTAGATAG<br>ATTTGAATGCCGGAACTTTGGATTTAGATCACCCATTGACTTGGTCAACG |
| SEQ ID No. 28:<br>Cpf1 CAR 2-16-4<br>Rev | CAAAGTACAAGCGATATAATTATCGCTTGTACTTTGTGGATAATAATGAACGCATTAGATAG<br>ATTTGAATGCCGGAACTTTGGATTTAGATCACCCATTGACTTGGTCAACG |
| SEQ ID No. 29:<br>Cpf1 CAR 2-16-4<br>PAMless | CGCTGTACAAGCGATATAATTATCGCTTGTACAGCGTGGATAATAATGAACGCATTAGATAG<br>ATAAGAATGCCGGAACTAAGGATAAAGATCACCCATTGACTTGGTCAACG |
| SEQ ID No. 30:<br>Cpf1 CAR 2-16-2 | GAAACATGTTCGCTATTAATATAGCGAACATGTTTCTGGATAATAATGAACGCATTAGATAG<br>ATTTGAATGCCGGAACTTTGGATTTAGATCACCCATTGACTTGGTCAACGGAAACATGTTCG<br>CTATTAATATAGCGAACATGTTTC |
| SEQ ID No. 31:<br>Cpf1 CAR 2-16-2<br>Rev | GTTTCATGTTCGCTATTAATATAGCGAACATGAAACTGGATAATAATGAACGCATTAGATAG<br>ATTTGAATGCCGGAACTTTGGATTTAGATCACCCATTGACTTGGTCAACGGTTTCATGTTCGC<br>TATTAATATAGCGAACATGAAAC |
| SEQ ID No. 32:<br>Cpf1 CAR 2-16-2<br>Double | GAAACATGAAAGCTATTAATATAGCTTTCATGTTTCTGGATAATAATGAACGCATTAGATAG<br>ATTTGAATGCCGGAACTTTGGATTTAGATCACCCATTGACTTGGTCAACGGAAACATGAAAG<br>CTATTAATATAGCTTTCATGTTTC |
| SEQ ID No. 33:<br>Cpf1 CAR 2-16-2<br>PAM 1 | GAAACATGTTCGCTATTAATATAGCGAACATGTTTCTGGATAATAATGAACGCATTAGATAG<br>ATTTGAATGCCGGAACTTTGGATTTAGATCACCCATTGACTTGGTCAACGGGCACATGTTCG<br>CTATTAATATAGCGAACATGTGCC |
| SEQ ID No. 34:<br>Cpf1 CAR 2-16-2<br>PAM 2 | GGCACATGTTCGCTATTAATATAGCGAACATGTGCCTGGATAATAATGAACGCATTAGATAG<br>ATTTGAATGCCGGAACTTTGGATTTAGATCACCCATTGACTTGGTCAACGGAAACATGTTCG<br>CTATTAATATAGCGAACATGTTTC |
| SEQ ID No. 35:<br>Cpf1 CAR 2-16-2<br>PAMless | GGCACATGTTCGCTATTAATATAGCGAACATGTGCCTGGATAATAATGAACGCATTAGATAG<br>ATTTGAATGCCGGAACTTTGGATTTAGATCACCCATTGACTTGGTCAACGGGCACATGTTCG<br>CTATTAATATAGCGAACATGTGCC |
| SEQ ID No. 36:<br>Cpf1 CAR 2-16-3 | CTTTGTACAAGCGATATAATTATCGCTTGTACAAAGTGGATAATAATGAACGCATTAGATAG<br>ATTTGAATGCCGGAACTTTGGATTTAGATCACCCATTGACTTGGTCAACGGAAACATGTTCG<br>CTATTAATATAGCGAACATGTTTC |
| SEQ ID No. 37:<br>Cpf1 CAR 2-16-3<br>Double | CTTTGTACTTTCGATATAATTATCGAAAGTACAAAGTGGATAATAATGAACGCATTAGATAG<br>ATTTGAATGCCGGAACTTTGGATTTAGATCACCCATTGACTTGGTCAACGGAAACATGAAAG<br>CTATTAATATAGCTTTCATGTTTC |
| SEQ ID No. 38:<br>Cpf1 CAR 2-16-5<br>2Ome2 | CTTTGTACTTTCGATmAmUmAmAmUmUATCGAAAGTACAAAGTGGATAATAATGAACGC<br>ATTAGATAGATTTGAATGCCGGAACTTTGGATTTAGATCACCCATTGACTTGGTCAACGGAA<br>ACATGAAAGCTAmUmUmAmAmUmATAGCTTTCATGTTTC |
| SEQ ID No. 39:<br>Cpf1 CAR 2-16-3<br>PAM1 | CTTTGTACAAGCGATATAATTATCGCTTGTACAAAGTGGATAATAATGAACGCATTAGATAG<br>ATTTGAATGCCGGAACTTTGGATTTAGATCACCCATTGACTTGGTCAACGGGCACATGTTCG<br>CTATTAATATAGCGAACATGTGCC |
| SEQ ID No. 40:<br>Cpf1 CAR 2-16-3<br>PAM2 | CGCTGTACAAGCGATATAATTATCGCTTGTACAGCGTGGATAATAATGAACGCATTAGATAG<br>ATTTGAATGCCGGAACTTTGGATTTAGATCACCCATTGACTTGGTCAACGGAAACATGTTCG<br>CTATTAATATAGCGAACATGTTTC |
| SEQ ID No. 41:<br>Cpf1 CAR 2-16-3<br>PAMless | CGCTGTACAAGCGATATAATTATCGCTTGTACAGCGTGGATAATAATGAACGCATTAGATAG<br>ATTTGAATGCCGGAACTTTGGATTTAGATCACCCATTGACTTGGTCAACGGGCACATGTTCG<br>CTATTAATATAGCGAACATGTGCC |
| SEQ ID No. 42:<br>Cpf1 CAR 2-16-6 | ATTTACTAGGTTACGCTAATGCGTAACCTAGTAAATTGGATAATAATGAACGCATTAGATAG<br>ATTTGAATGCCGGAACTTTGGATTTAGATCACCCATTGACTTGGTCAACGGAAACATGTTCG<br>CTATTAATATAGCGAACATGTTTC |
| SEQ ID No. 43:<br>Cpf1 CAR 2-16-6<br>PAMless | AGCTACTAGGTTACGCTAATGCGTAACCTAGTAGCTTGGATAATAATGAACGCATTAGATAG<br>ATAAGAATGCCGGAACTAAGGATAAAGATCACCCATTGACTTGGTCAACGGGCACATGTTC<br>GCTATTAATATAGCGAACATGTGCC |
| SEQ ID No. 44:<br>Cpf1 CAR 2-16-6<br>PS2 | A*T*T*TACTAGGTTACGCTAATGCGTAACCTAGTAAATTGGATAATAATGAACGCATTAGAT<br>AGATTTGAATGCCGGAACTTTGGATTTAGATCACCCATTGACTTGGTCAACGGAAACATGTT<br>CGCTATTAATATAGCGAACATGT*T*T*C |

TABLE 3-continued

List of sequences tested in Example 3.

| SEQ ID No. | Sequence |
|---|---|
| SEQ ID No. 45:<br>Cpf1 CAR 2-16-6<br>2Ome2 | ATTTACTAGGTTACGmCmUmAmAmUmGCGTAACCTAGTAAATTGGATAATAATGAACGC<br>ATTAGATAGATTTGAATGCCGGAACTTTGGATTTAGATCACCCATTGACTTGGTCAACGGAA<br>ACATGTTCGCTAmUmUmAmAmUmATAGCGAACATGTTTC |
| SEQ ID No. 46:<br>Cpf1 CAR 3-16 | TTAGCTCTGTTTACGTCCCAGCGGGCATGAGAGTAACAAGAGGGTGTGGTAATATTACGGT<br>ACCGAGCACTATCGATACAATATGTGTCATACGGACACGGAAACATGTTCGCTATTAATATA<br>GCGAACATGTTTC |

DNA bases are uppercase, mA mC mU mG are 2'-O-methylated residues. "*" indicates a phosphorothioate internucleotide linkage.

EXAMPLE 4

The following example illustrates the effects of dilution of the carrier DNA on cell transfection.

Example 3 demonstrated the effect of different designs of the Cpf1-based carrier DNA on editing efficiency. In this example, two designs were studied in more detail; Cpf1 CAR 2-16 (SEQ ID No. 9) which has a 3' hairpin structure, and Cpf1 CAR 2-16 Middle (SEQ ID No. 25) which has a hairpin structure in the middle of the carrier DNA.

Figure 6A:
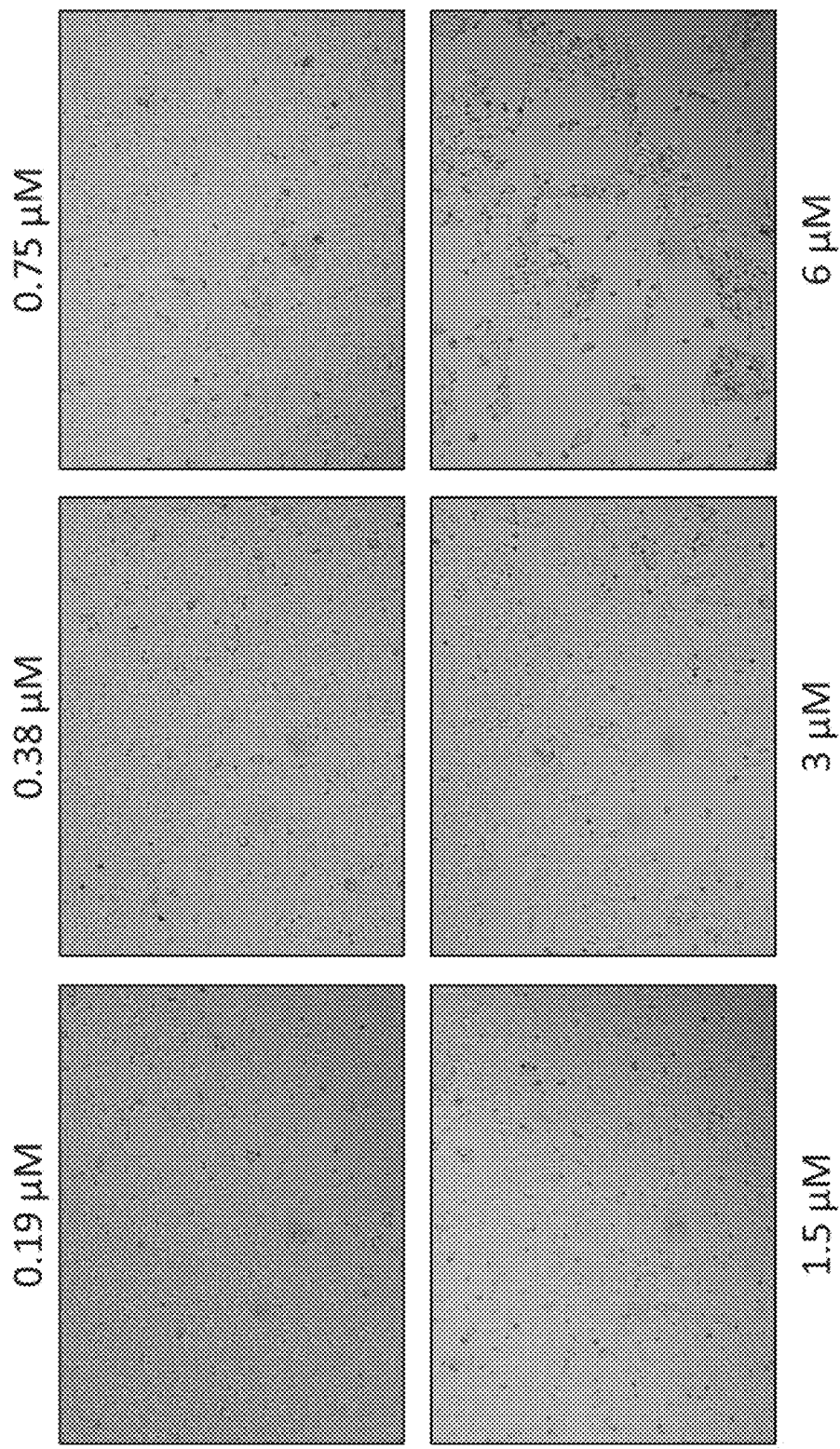
FIGS. 6A-6C illustrate a dilution series for carrier DNA Cpf1 CAR 2-16 and Cpf1 CAR 2-16 Middle (SEQ ID No. 25). HEK293 cells were Nucleofected (3.5E5 cells/DS-150 protocol) with RNP in complex with either Cpf1 CAR 2-16 and Cpf1 CAR 2-16 Middle carrier constructs, these constructs being at a concentration range of 0.19-6 µM. The ratio of Cpf1:crRNA was 1:1.2. RNP concentration was held constant at 5 µM. The crRNA was specific to the HPRT gene at position 38104-S. After a 48 hour post-Nucleofection incubation, the genomic DNA was isolated, the target region amplified by PCR, digested with 2 U T7EI endonuclease, then the percent editing was determined via capillary electrophoresis using a Fragment Analyzer.
Figure 6B:
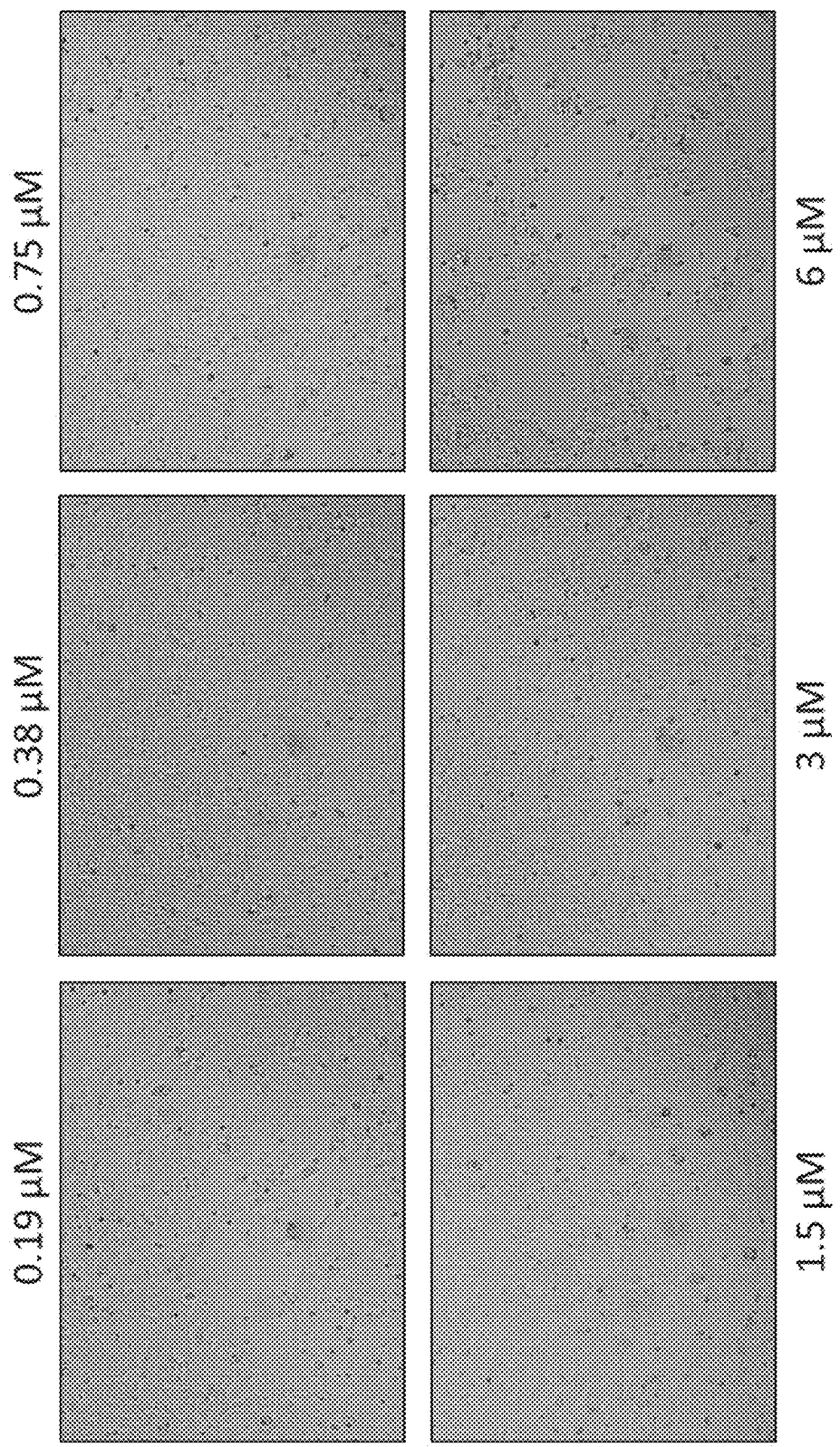
Figure 6C:
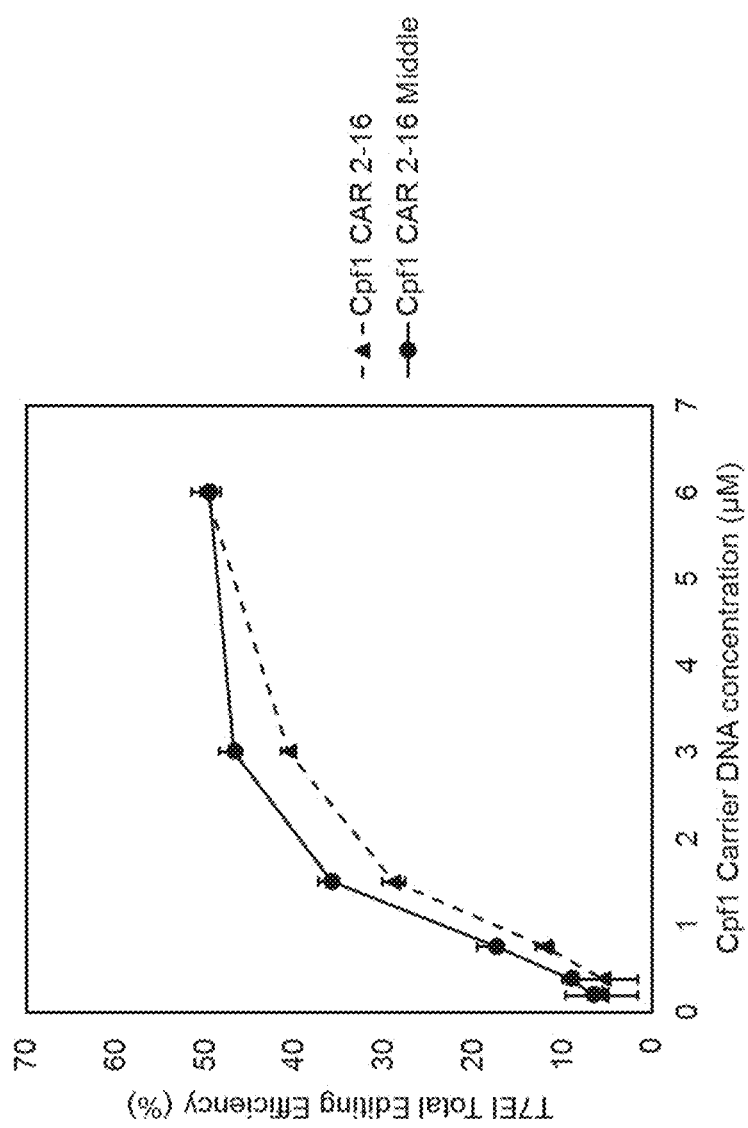

HEK293 cells were Nucleofected (3.5E5 cells/DS-150 protocol) with RNP in complex with either Cpf1 CAR 2-16 (SEQ ID No. 9) or Cpf1 CAR 2-16 Middle (SEQ ID No. 25) carrier DNAs, with these carrier DNAs having a concentration range of 0.19-6 µM during electroporation. The ratio of Cpf1:crRNA was 1:1.2. RNP concentration was 5 µM. The crRNA was specific to the HPRT gene at position 38104-S (Table 8: SEQ ID No. 68). After a 48 hour post-Nucleofection incubation, the genomic DNA was isolated, the target region amplified by PCR (Table 9: SEQ ID Nos. 81 and 82), digested with 2 U T7EI endonuclease, then the percent editing was determined via capillary electrophoresis using a Fragment Analyzer. FIGS. 6A-6C illustrate a dilution series for Cpf1 CAR 2-16 and Cpf1 CAR 2-16 Middle. Analysis of cell toxicity as a function of carrier DNA concentration for Cpf1 CAR 2-16 (FIG. 6A) and Cpf1 CAR 2-16 Middle (FIG. 6B). Cell culture images were taken at 40 hours post-Nucleofection. Editing efficiency of Cpf1 as a function of the concentrations of Cpf1 CAR 2-16 (dashed line) and Cpf1 CAR 2-16 Middle (solid line) carrier DNA concentrations (FIG. 6C).

Optimal concentration of either a 3' hairpin (Cpf1 CAR 2-16, SEQ ID No. 9) or middle hairpin (Cpf1 CAR 2-16 Middle, SEQ ID No. 25) carrier DNA was determined by generating a dose response curve. FIG. 6C shows a positive correlation between carrier DNA concentration and editing efficiency. Maximum editing efficiency for site HPRT 38104-S is reached with 3 µM carrier DNA in combination with 5 µM RNP. Cellular toxicity was observed at high doses of carrier DNA (6 µM) for both Cpf1 CAR 2-16 and Cpf1 CAR 2-16 Middle. Toxicity might depend on cell type.

EXAMPLE 5

The following example demonstrates the effect of varying the ratio of carrier to RNP.

Example 4 demonstrated optimization of Cpf1 carrier DNA concentration when a constant RNP concentration was used. In this example, a range of RNP concentrations was tested with two different ratios of Cpf1 CAR 2-16 Middle (SEQ ID No. 25).

Figure 7A:
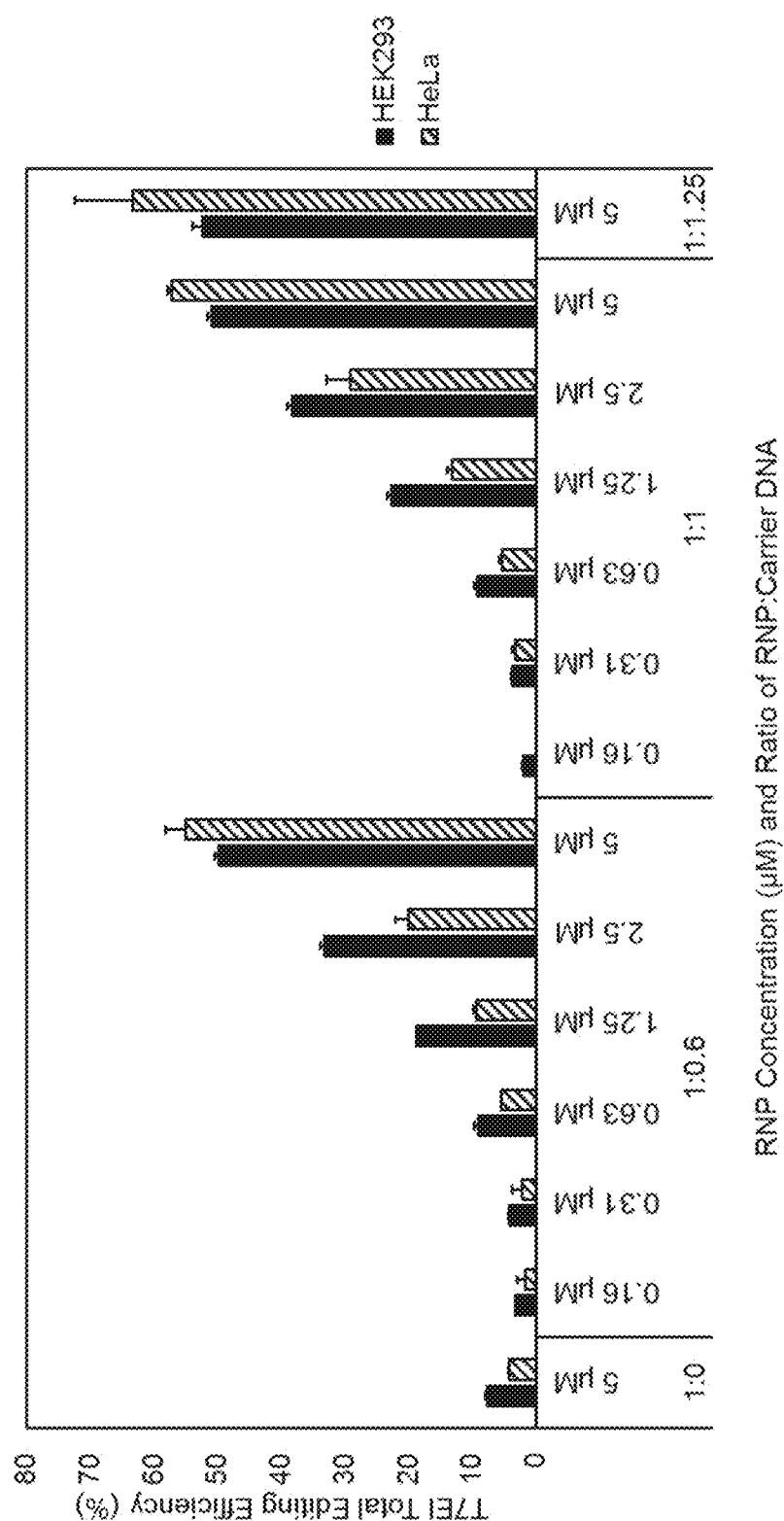
FIG. 7A illustrates the effect of RNP and carrier ratios on editing efficiency, wherein the editing efficiency of RNP complexes ranging in concentration from 0.16-5 µM complexed with Cpf1 CAR 2-16 Middle carrier DNA at RNP:carrier ratios of either 1:1, 1:0.6, 1:0 or 1:1.25 in either HEK293 cells (solid black bars) or HeLa cells (striped bars).
Figure 7B:
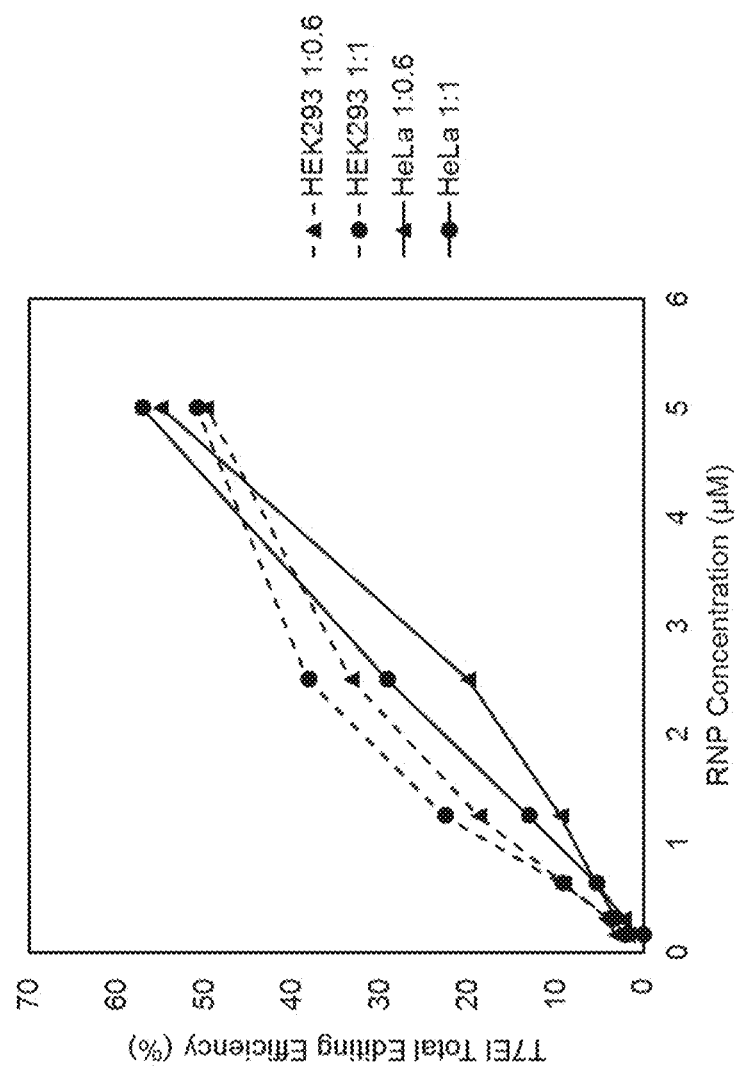
FIG. 7B shows a line graph version of the data in FIG. 7A.

FIGS. 7A and 7B illustrate the effect of RNP and carrier DNA ratios on editing efficiency. FIG. 7A shows the editing efficiency of RNP complexes ranging in concentration from 0.16-5 µM complexed with Cpf1 CAR 2-16 Middle (SEQ ID No. 25) at RNP:carrier DNA ratios of either 1:1, 1:0.6, 1:0 or 1:1.25 in either HEK293 cells (solid black bars) or HeLa cells (striped bars). FIG. 7B shows a line graph version of the data in FIG. 7A. Both cell types were Nucleofected (3.5E5 cells using the DS-150 (HEK293) or CN-114 (HeLa) protocol) with the RNP:carrier DNA described above. The ratio of Cpf1:crRNA was 1:1.2. The crRNA is specific to the HPRT gene at position 38104-S (Table 8: SEQ ID No. 68). After a 48 hour post-Nucleofection incubation, the genomic DNA was isolated, the target region amplified by PCR (SEQ ID Nos. 81 and 82), digested with 2 U T7EI endonuclease, then the percent editing was determined via capillary electrophoresis on a Fragment Analyzer.

Optimal ratios of RNP:carrier DNA were determined by testing different RNP concentrations with the addition of carrier DNA at specific ratios. FIG. 7A shows absence of carrier DNA (ratio 1:0) leads to low levels of editing. A positive correlation was found between RNP/carrier DNA concentration and editing efficiency. A ratio of RNP:carrier DNA of 1:1 leads to higher editing efficiencies compared to a ratio of 1:0.6. However, as high concentrations of carrier DNA can lead to increased toxicity and high concentrations of RNP lead to high levels of editing, the optimal RNP concentration ratio is 5 µM with a carrier DNA concentration of 3 µM.

EXAMPLE 6

The following example demonstrates the effect of Cpf1 CAR 2-16 Middle (SEQ ID No. 25) on editing efficiency of different targets within the HPRT gene locus.

HEK293 cells were Nucleofected (3.5E5 cells/DS-150) using different crRNAs targeting the HPRT gene (Table 8: SEQ ID No. 68-79). RNPs were delivered at 5 µM with a Cpf1:crRNA ratio of 1:1.2 with or without Cpf1 CAR 2-16 Middle (SEQ ID No. 25) at a concentration of 3 µM. After a 48 hour post-Nucleofection incubation, the genomic DNA was isolated, the target region amplified by PCR (SEQ ID Nos. 81 and 82), digested with 2 U T7EI endonuclease, then the percent editing was determined via capillary electrophoresis on a Fragment Analyzer. Addition of carrier DNA dramatically increases editing efficiency at all sites.

Figure 8:
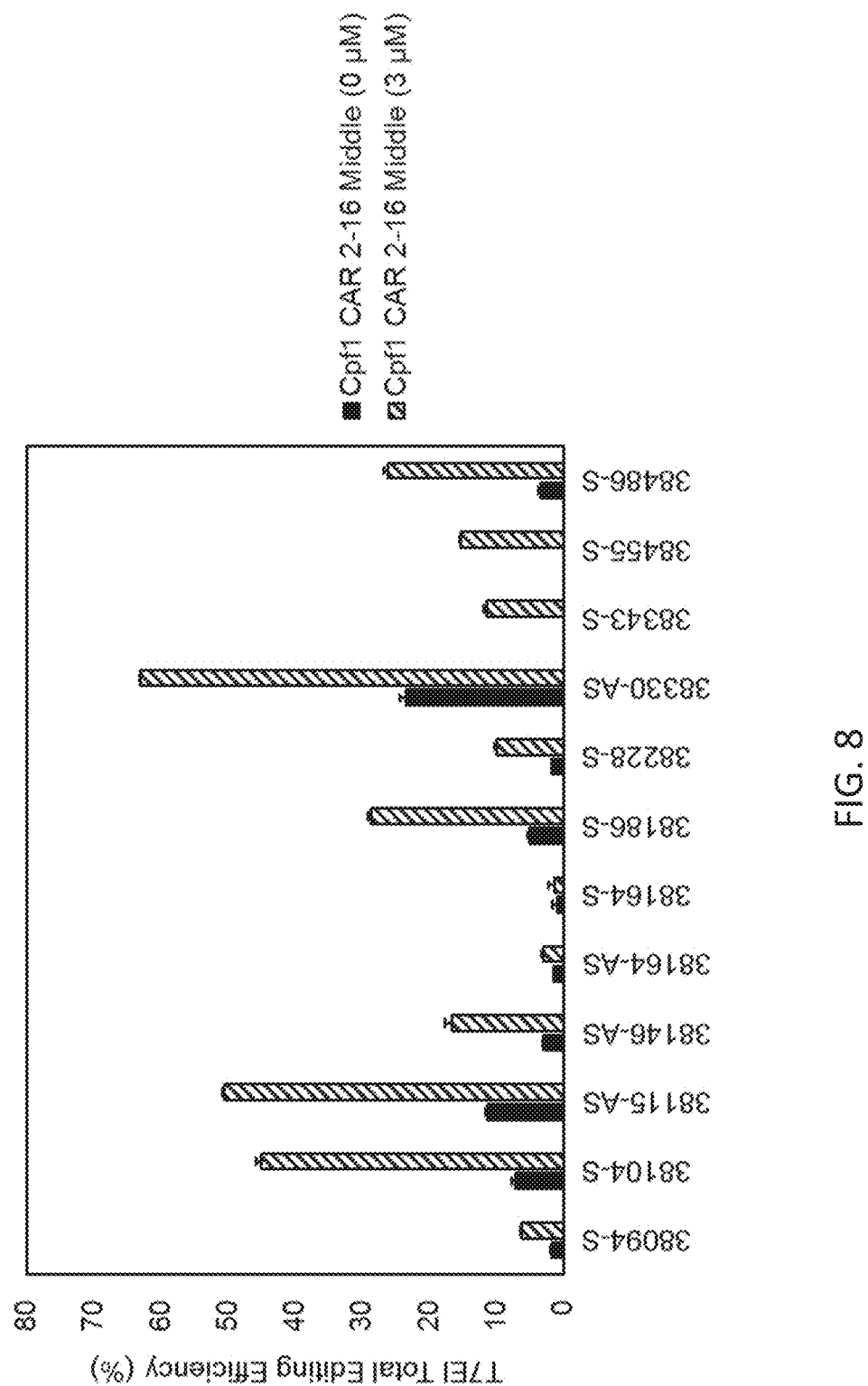
FIG. 8 illustrates the effect of carrier DNA Cpf1 CAR 2-16 Middle on editing efficiency of different targets within the HPRT gene locus. HEK293 cells were Nucleofected (3.5E5 cells/DS-150) using different crRNAs targeting the HPRT gene. RNPs were delivered at 5 µM with a Cpf1:crRNA ratio of 1:1.2 with or without carrier DNA Cpf1 CAR 2-16 Middle at a concentration of 3 µM. Addition of carrier DNA dramatically increases editing efficiency at all sites.

Editing efficiency also depends on the potency of the target crRNA. The effect of adding carrier DNA on editing efficiency was determined at 12 different target sites within the HPRT gene (FIG. 8). In all cases, the addition of Cpf1 CAR 2-16 Middle led to an increase in editing efficiency. As a result, the editing reached high levels (>25%) for some sites (38104-S (SEQ ID No. 68), 38115-AS (SEQ ID No. 70), 38186-S (SEQ ID No. 74), 38330-AS (SEQ ID No. 76), 38486-S (SEQ ID No. 79)). For other sites, addition of carrier DNA was required for editing to occur (38343-S (SEQ ID No. 77), 38455-S (SEQ ID No. 78)). The remaining sites had overall low editing efficiencies (38094-S (SEQ ID No. 69), 38146-AS (SEQ ID No. 71), 38164-AS (SEQ ID No. 72), 38164-S (SEQ ID No. 73), 38228-S (SEQ ID No. 75)), but addition of carrier DNA still increased editing efficiency significantly.

EXAMPLE 7

The following example demonstrates integration of single-stranded and double-stranded oligonucleotides at double-stranded breaks.

HEK293 cells were electroporated using the Amaxa Nucleofector System by Lonza. After harvesting the cells using trypsinization and subsequent neutralization of the trypsin by addition of growth media containing 10% Fetal Bovine Serum (FBS), cells were counted and pelleted using centrifugation (200 rpm, 10 minutes at room temperature). The pelleted cells were washed with one volume of at least 5 mL 1× phosphate-buffered saline (PBS). The cells were then pelleted and resuspended in Nucleofection Solution SF at a concentration of 1.75E7 cells/mL. The guide RNA complex was generated by hybridization of crRNA and tracrRNA at a final concentration of 60 µM in IDTE. The crRNA was specific to the EMX1 gene (Table 8: EMX1C3 (SEQ ID No. 80)). The ribonucleoprotein complex (RNP) was generated by complexation of 108 pmol Cas9 protein with 129.6 pmol guide RNA complex in a total volume of 5 µL. Phosphate-Buffered Saline was used to adjust to the final volume. The complexation of the RNP was achieved by incubation for 10-20 minutes at room temperature. Single-stranded oligonucleotides were resuspended at a concentration of 64.8 µM. Double-stranded oligonucleotides were combined at equimolar concentrations in IDTE, heated at 95° C. for 5 minutes and cooled down at room temperature. The final concentration of double-stranded oligonucleotides was 16.2 µM. For each electroporation, 5 µL of RNP complex and 2 µL of either single-, or double-stranded oligonucleotides were added to 20 µL of HEK293 cells in Nucleofection Solution SF (3.5E5 cells). 25 µL out of 27 µL of the solution was mixed by pipetting up and down and transferred to an electroporation cuvette. The cells were electroporated according to the manufacturers protocol using the Amaxa 96-well Shuttle device and Nucleofection setting 96-DS-150. After electroporation, the cells were resuspended with 75 µL pre-warmed culture media in the electroporation cuvette. Triplicate aliquots of 25 µL of resuspended cells were further cultured in 175 µL pre-warmed media each. Genomic DNA was isolated after the cells were incubated for 48 hours at 37° C. containing 5% $CO_2$.

The integration of single-, and double-stranded DNA was studied in a non-biased screen using the GUIDE-Seq approach (Tsai et al., Nat Biotech (2015) 33:187-197). In short, the GUIDE-Seq (genome-wide, unbiased identification of DSBs enabled by sequencing) methodology is an NGS based method which relies on the capture of double-stranded oligonucleotides into DSBs. The list of sequences used for this Example is presented in Table 4. The double-stranded GUIDE-Seq tag (dsGS-tag) is generated by hybridizing the GUIDE-Seq top strand (SEQ ID No. 49) with the GUIDE-Seq bottom strand (SEQ ID No. 50) in equimolar fashion. Next to the dsGS-tag, a 134-nucleotide long single-stranded oligonucleotide was used that is a combination of the Alt-R Carrier 3 (SEQ ID No. 4) sequence and the 34 nucleotide GUIDE-Seq sequence (GUIDE-Seq top strand, SEQ ID No. 49). This resulted in ss134nt (SEQ ID No. 47). Additionally, a double stranded version of this (ds134nt) was tested as well. The ds134nt is generated by hybridizing the ss134nt (SEQ ID No. 47) with ss134rc (SEQ ID No. 48) in equimolar fashion. These 3 templates (ss134nt, ds134nt, and dsGS-tag) were introduced separately into HEK293 cells in the presence of a ribonucleoprotein complex targeting EMX1. Libraries were generated from genomic DNA isolated after 48 hours of incubation, and these were run on an Illumina MiSeq cartridge per the manufacturers protocol. The number of unique targeted reads was normalized against the number of total reads for each sample. Bioinformatic analysis of the reads allows for the identification of the genomic location where the integration occurs. Integration of single-, and double-stranded tags was detected at the same genomic locations, which corresponded with the earlier published ON- and OFF-target sites (Table 5).

TABLE 4

List of sequences used in Example 7.

| SEQ ID No. | Sequence |
| --- | --- |
| SEQ ID No. 47: ss134nt | TTAGCTCTGTTTACGTCCCAGCGGGCATGAGAGTAACAAGAGGGTGTGGTAATAT TACGGTACCGAGCACTATCGATACAATATGTGTCAGTTTAATTGAGTTGTCATATG TTAATAACGGTATTACGGACACG |
| SEQ ID No. 48: ss134rc | CGTGTCCGTAATACCGTTATTAACATATGACAACTCAATTAAACTGACACATATTGT ATCGATAGTGCTCGGTACCGTAATATTACCACACCCTCTTGTTACTCTCATGCCCGC TGGGACGTAAACAGAGCTAA |
| SEQ ID No. 49: GUIDE-Seq top strand | /5Phos/G*T*TTAATTGAGTTGTCATATGTTAATAACGGT*A*T |
| SEQ ID No. 50: GUIDE-Seq bottom strand | /5Phos/A*T*ACCGTTATTAACATATGACAACTCAATTAA*A*C |

Table 5 shows the normalized number of unique targeted reads for the ON-target site (EMX1C3 protospacer; SEQ ID No. 80) as well as 5 OFF-target sites (SEQ ID Nos. 87-91) identified by the GUIDE-Seq method when 3 different oligonucleotide constructs were introduced together with the CRISPR machinery targeting EMX1. The double-stranded oligonucleotides ds134nt (hybridization product of SEQ ID Nos. 47 and 48) and dsGS-tag (hybridization product of SEQ ID Nos. 49 and 50) showed 58 and 153 reads at the ON-target site, respectively. The single-stranded ss134nt showed a smaller number of reads (12 reads). For the OFF-target sites a similar pattern was observed; the double-stranded oligonucleotides integrate more efficiently than the single-stranded oligonucleotide. Therefore, when single-stranded carrier DNA is used to boost editing efficiency, integration of the carrier DNA can occur at the ON-target as well as OFF-target sites.

TABLE 5

Number of targeted reads for each of the genomic locations where insertion of the tag was detected. The published sites are found in (Tsai et al., Nat Biotech (2015) 33: 187-197)

| ON/OFF target | Chromo-some | Target sequence | SEQ ID No. | Published site* | Number of Unique Targeted Reads ||| 
|---|---|---|---|---|---|---|---|
| | | | | | ss134nt | ds134nt | dsGS-tag |
| ON  | Chr2  | GAGTCCGAGCAGAAGAAGAA | 80 | ON   | 12 | 58 | 153 |
| OFF | Chr5  | GAGTTAGAGCAGAAGAAGAA | 87 | OFF1 | 27 | 40 | 67  |
| OFF | Chr15 | GAGTCTAAGCAGAAGAAGAA | 88 | OFF2 | 0  | 15 | 8   |
| OFF | Chr2  | GAGGCCGAGCAGAAGAAAGA | 89 | OFF3 | 0  | 5  | 0   |
| OFF | Chr13 | CACAGCTAGCAGAAAAAGTA | 90 | —    | 0  | 0  | 2   |
| OFF | Chr5  | AAGTCTGAGCACAAGAAGAA | 91 | OFF5 | 0  | 0  | 1   |

EXAMPLE 8

The following example demonstrates the effects of modifications of the carrier DNA on editing efficiency, as well as the rate of integration of the carrier DNA.

Example 7 shows that single-stranded DNA integrates into double-stranded breaks, but not as efficiently as double-stranded DNA does. This example focuses on the effect of modifications in the carrier DNA on editing efficiency and rate of integration of the carrier DNA. The carrier DNA variants were based on the Alt-R Carrier 3 sequence (SEQ ID No. 4) for Cas9, and the Cpf1 CAR 2-16 Middle sequence (SEQ ID No. 25) for Cpf1. Table 6 shows the different carrier DNA designs; Cas9-based 'carrier DNAs' with C3 and S9 spacer variants (SEQ ID Nos. 51-60), Cas9-based 'carrier DNAs' with dSpacer variants (SEQ ID Nos. 60-64), and Cpf1-based carrier DNA variants (SEQ ID Nos. 65-66).

TABLE 6

List of sequences tested in Examples 8.

| SEQ ID No. | Sequence |
|---|---|
| SEQ ID No. 51:<br>AC3-No spacers,<br>blocked ends | /5SpC3/TTAGCTCTGTTTACGTCCCAGCGGGCATGAGAGTAACAAGAGGGTGTGGT<br>AATATTACGGTACCGAGCACTATCGATACAATATGTGTCATACGGACACG/3SpC3/ |
| SEQ ID No. 52:<br>AC3-3x C3 | TTAGCTCTGT/iSpC3/TTACGTCCCAGCGGGCATGAGAGTAACAAGAGGGTGTGGT/<br>iSpC3/AATATTACGGTACCGAGCACTATCGATACAATATGTGTCA/iSpC3/TACGGA<br>CACG |
| SEQ ID No. 53:<br>AC3-6x C3 | TTAGCTCTGT/iSpC3/TTACGTCCCA/iSpC3/GCGGGCATGAGAGTAACAAG/iSpC3/<br>AGGGTGTGGTAATATTACGG/iSpC3/TACCGAGCACTATCGATACA/iSpC3/ATATG<br>TGTCA/iSpC3/TACGGACACG |
| SEQ ID No. 54:<br>AC3-9x C3 | TTAGCTCTGT/iSpC3/TTACGTCCCA/iSpC3/GCGGGCATGA/iSpC3/GAGTAACAAG<br>/iSpC3/AGGGTGTGGT/iSpC3/AATATTACGG/iSpC3/TACCGAGCAC/iSpC3/TATC<br>GATACA/iSpC3/ATATGTGTCA/iSpC3/TACGGACACG |
| SEQ ID No. 55:<br>AC3-9x C3,<br>blocked ends | /5SpC3/TTAGCTCTGT/iSpC3/TTACGTCCCA/iSpC3/GCGGGCATGA/iSpC3/GAGT<br>AACAAG/iSpC3/AGGGTGTGGT/iSpC3/AATATTACGG/iSpC3/TACCGAGCAC/iSpC3/<br>TATCGATACA/iSpC3/ATATGTGTCA/iSpC3/TACGGACACG/3SpC3/ |
| SEQ ID No. 56:<br>AC3-9x S9 | TTAGCTCTGT/iSp9/TTACGTCCCA/iSp9/GCGGGCATGA/iSp9/GAGTAACAAG/iSp9/<br>AGGGTGTGGT/iSp9/AATATTACGG/iSp9/TACCGAGCAC/iSp9/TATCGATACA/<br>iSp9/ATATGTGTCA/iSp9/TACGGACACG |
| SEQ ID No. 57:<br>AC3-19x C3 | TTAGC/iSpC3/TCTGT/iSpC3/TTACG/iSpC3/TCCCA/iSpC3/GCGGG/iSpC3/CATGA<br>/iSpC3/GAGTA/iSpC3/ACAAG/iSpC3/AGGGT/iSpC3/GTGGT/iSpC3/AATAT/iSpC3/<br>TACGG/iSpC3/TACCG/iSpC3/AGCAC/iSpC3/TATCG/iSpC3/ATACA/iSpC3/ATA<br>TG/iSpC3/TGTCA/iSpC3/TACGG/iSpC3/ACACG |
| SEQ ID No. 58:<br>AC3-58x C3,<br>blocked ends | /5SpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//iSpC3/CGG /iSpC3//iSpC3//iSpC3//iSpC3/CGG<br>/iSpC3//iSpC3//iSpC3//3SpC3/ |

TABLE 6-continued

List of sequences tested in Examples 8.

| SEQ ID No. | Sequence |
|---|---|
| SEQ ID No. 59:<br>AC3-100x C3,<br>blocked ends | /5SpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//iSpC3//iSpC3//iSpC3//iSpC3//iSpC3//iSpC3//iSpC3//iSpC3//<br>iSpC3//3SpC3/ |
| SEQ ID No. 60:<br>AC3-58x C3,<br>42x dSp,<br>blocked ends | /5SpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//iSpC3//idSp//idSp//idSp/<br>/iSpC3//iSpC3//iSpC3//3SpC3/ |
| SEQ ID No. 61:<br>AC3-9x dSp,<br>blocked ends | /5SpC3/TTAGCTCTGT/idSp/TTACGTCCCA/idSp/GCGGGCATGA/idSp/GAGTAAC<br>AAG/idSp/AGGGTGTGGT/idSp/AATATTACGG/idSp/TACCGAGCAC/idSp/TATCG<br>ATACA/idSp/ATATGTGTCA/idSp/TACGGACACG/3SpC3/ |
| SEQ ID No. 62:<br>AC3-19x dSp,<br>blocked ends | /5SpC3/TTAGC/idSp/TCTGT/idSp/TTACG/idSp/TCCCA/idSp/GCGGG/idSp/CAT<br>GA/idSp/GAGTA/idSp/ACAAG/idSp/AGGGT/idSp/GTGGT/idSp/AATAT/idSp/TA<br>CGG/idSp/TACCG/idSp/AGCAC/idSp/TATCG/idSp/ATACA/idSp/ATATG/idSp/T<br>GTCA/idSp/TACGG/idSp/ACACG/3SpC3/ |
| SEQ ID No. 63:<br>AC3-36x dSp,<br>blocked ends | /5SpC3//idSp//idSp/CGG/idSp//idSp/CGG/idSp//idSp/CGG/idSp//idSp/CGG/<br>idSp//idSp/CGG/idSp//idSp/CGG/idSp//idSp/CGG/idSp//idSp/CGG/idSp//idSp/<br>CGG/idSp//idSp/CGG/idSp//idSp/CGG/idSp//idSp/CGG/idSp//idSp/CGG/idSp//<br>idSp/CGG/idSp//idSp/CGG/idSp//idSp/CGG/idSp//idSp/CGG/idSp//idSp/3SpC3/ |
| SEQ ID No. 64:<br>AC3-100x dSp,<br>blocked ends | /5dSp//idSp//idSp//idSp//idSp//idSp//idSp//idSp//idSp//idSp//idSp//<br>idSp//idSp//idSp//idSp//idSp//idSp//idSp//idSp//idSp//idSp//idSp/<br>/idSp//idSp//idSp//idSp//idSp//idSp//idSp//idSp//idSp//idSp//idSp//<br>idSp//idSp//idSp//idSp//idSp//idSp//idSp//idSp//idSp//idSp//idSp/<br>/idSp//idSp//idSp//idSp//idSp//idSp//idSp//idSp//idSp//idSp//<br>idSp//idSp//idSp//idSp//idSp//idSp//idSp//idSp//idSp//idSp//idSp/<br>/idSp//idSp//idSp//idSp//idSp//idSp//idSp//idSp//idSp//idSp//<br>idSp//idSp//idSp//idSp//idSp//idSp//idSp//idSp//idSp//idSp//idSp/<br>/idSp//3d5p/ |
| SEQ ID No. 65:<br>216M-No<br>spacers,<br>blocked ends | /5SpC3/TGGATAATAATGAACGCATTAGATAGATTTGAATGCGAAACATGTTCGCT<br>ATTAATATAGCGAACATGTTTCCGGAACTTTGGATTTAGATCACCCATTGACTTGGT<br>CAACG/3SpC3/ |
| SEQ ID No. 66:<br>216M-6x dSp,<br>blocked ends | /5SpC3/TGGATAATAA/iSpC3/TGAACGCATT/iSpC3/AGATAGATTT/iSpC3/GAAT<br>GCGAAACATGTTCGCTATTAATATAGCGAACATGTTTCCGGAACTTTG/iSpC3/GATT<br>TAGATC/iSpC3/ACCCATTGAC/iSpC3/TTGGTCAACG/3SpC3/ |

SpC3 indicates C3 spacer (propanediol), Sp9 indicates Spacer 9 (triethylene glycol), and dSp indicates dSpacer (abasic ribose).

HEK293 cells were electroporated using the Amaxa Nucleofector System (Lonza). After harvesting the cells using trypsinization and subsequent neutralization of the trypsin by addition of growth media containing 10% Fetal Bovine Serum (FBS), cells were counted and pelleted using centrifugation (200 rpm, 10 minutes at room temperature). The pelleted cells were washed with one volume of at least 5 mL 1× phosphate-buffered saline (PBS). The cells were then pelleted and resuspended in Nucleofection Solution SF at a concentration of 1.75E7 cells/mL. For Cas9 experiments, the guide RNA complex was generated by hybridization of crRNA and tracrRNA at a final concentration of 60 µM in IDTE. The crRNA was specific to the HPRT gene at position 38285-AS (Table 8: SEQ ID No. 67). The ribonucleoprotein complex (RNP) was generated by complexation of 108 pmol Cas9 protein with 129.6 pmol guide RNA complex in a total volume of 5 µL. Phosphate-Buffered Saline was used to adjust to the final volume. For Cpf1 experiments, 135 pmol Cpf1 protein was mixed with 162 pmol guide RNA in a total volume of 5 μL. The complexation of the RNP was achieved by incubation for 10-20 minutes at room temperature. The crRNA was specific to the HPRT gene at position 38104-S (Table 8: SEQ ID No. 68). For each electroporation, 5 μL of RNP complex was added to 20 μL of HEK293 cells in Nucleofection Solution SF (3.5E5 cells). Additionally, 2 μL of carrier DNA, diluted in IDTE, was added to achieve its desired final concentration; 4.8 μM for the Cas9-based variants, and 3 μM for the Cpf1-based variants. 25 μL out of 27 μL of the solution was mixed by pipetting up and down and transferred to an electroporation cuvette. The cells were electroporated according to the manufacturers protocol using the Amaxa 96-well Shuttle device and Nucleofection setting 96-DS-150. After electroporation, the cells were resuspended with 75 μL pre-warmed culture media in the electroporation cuvette. Triplicate aliquots of 25 μL of resuspended cells were further cultured in 175 μL pre-warmed media each. Genomic DNA was isolated after the cells were incubated for 48 hours at 37° C. containing 5% $CO_2$. The targeted genomic locus was amplified using PCR (Table 9: SEQ ID Nos 81 and 82). Heteroduplexes were formed by denaturing the amplicons followed by a slow cool-down. Mismatches in heteroduplexes were cleaved by T7 Endonuclease I (T7EI), and cleaved and non-cleaved products were quantified by capillary electrophoresis using a Fragment Analyzer. Targeted next-generation sequencing was performed on the ON-target site using primer pairs for Cas9-based experiments (Table 9: SEQ ID Nos. 83 and 84) or using primer pairs for Cpf1-based experiments (Table 9: SEQ ID Nos. 85 and 86).

Figure 9A:
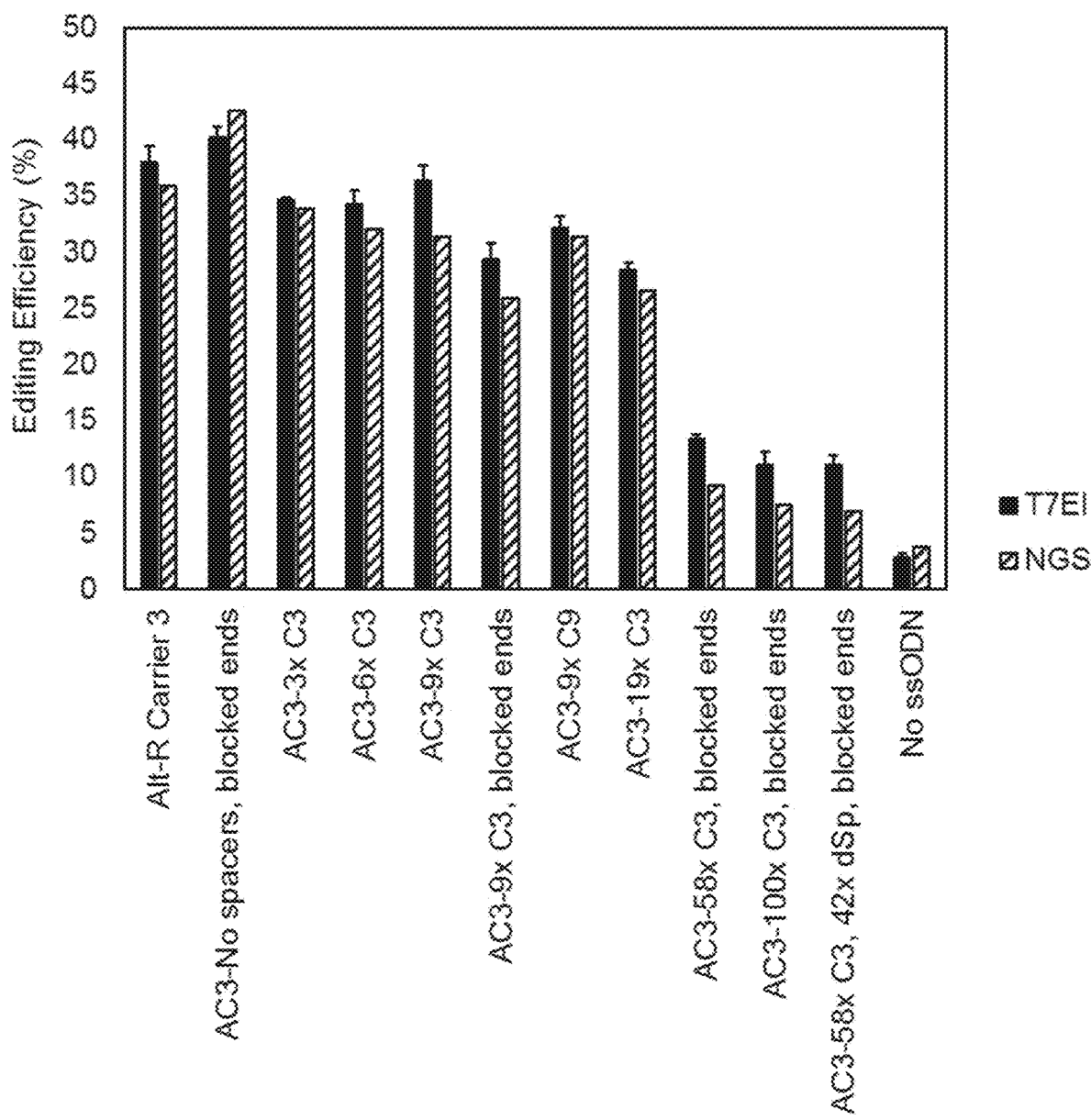
FIG. 9A shows the effect of different carrier DNA designs on editing efficiency using Cas9 carrier DNA variants with C3 or S9 spacers. Editing efficiency was determined in HEK293 cells electroporated with either a Cpf1-based RNP or a Cas9-based RNP as well as different carrier DNA designs. Editing efficiency was measured with the T7EI mismatch assay (solid black bars) or via next-generation sequencing (striped bars).
Figure 9B:
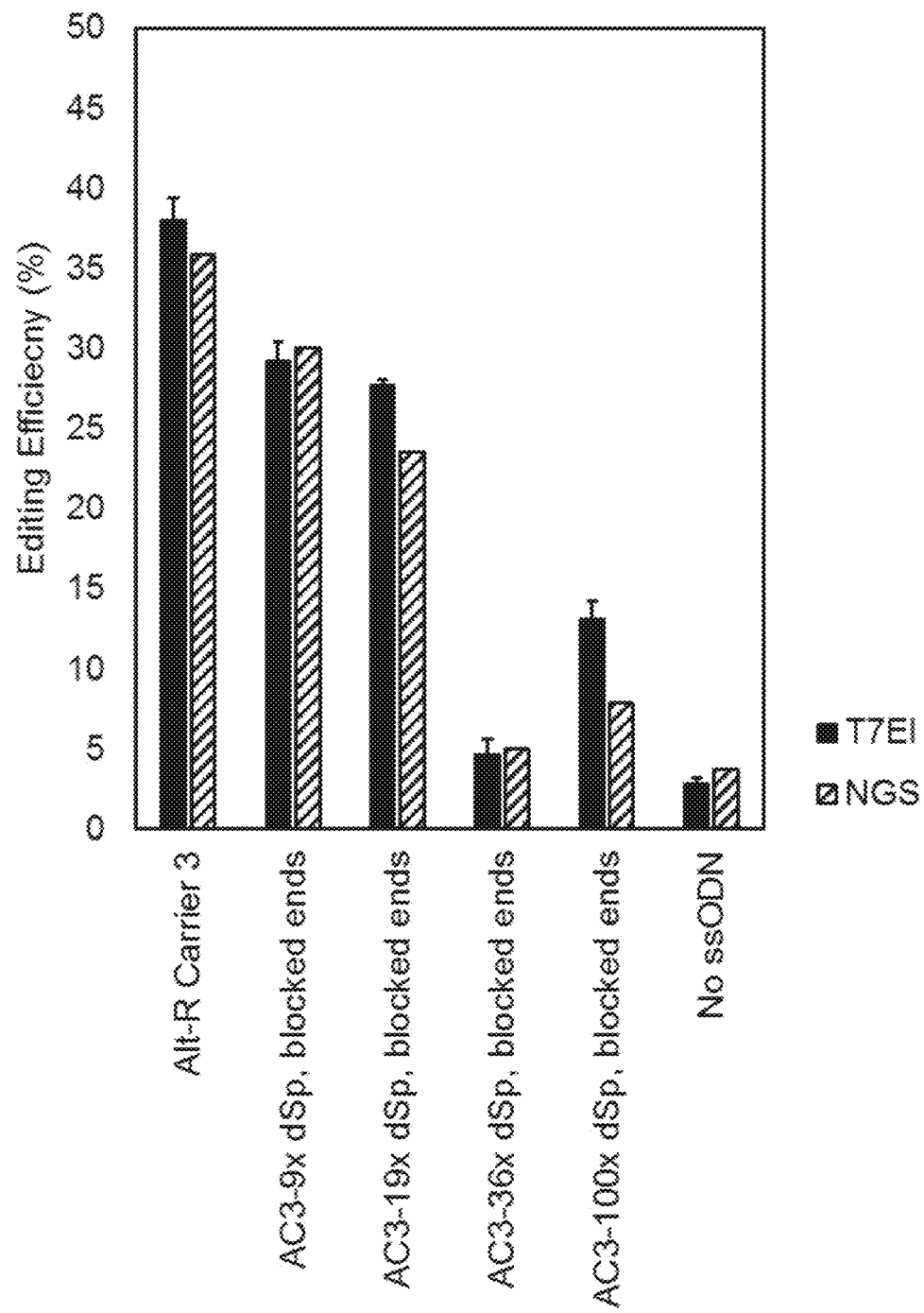
FIG. 9B show the effect of different carrier DNA designs on editing efficiency using Cas9 carrier DNA variants containing abasic dSpacers. Editing efficiency was determined in HEK293 cells as described in FIG. 9A FIG. 9C show the effect of different carrier DNA designs on editing efficiency using Cpf1 carrier DNA variants. Editing efficiency was determined in HEK293 cells as described in FIG. 9A
Figure 9C:
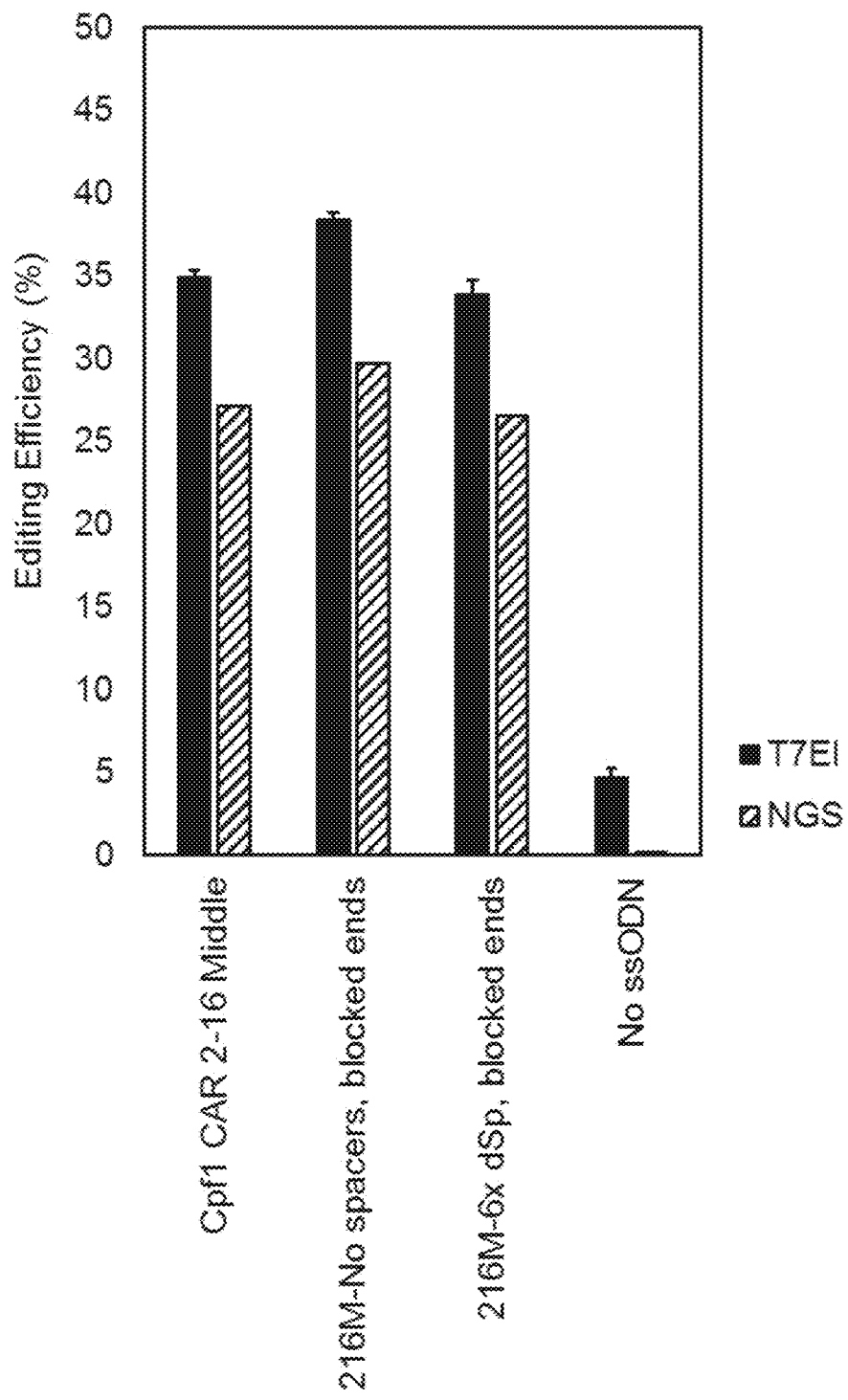

Similar editing efficiencies were detected with the T7EI mismatch endonuclease assay and targeted next-generation sequencing (NGS). The introduction of no more than 19 C3 or S9 spacers in the Cas9-related carrier DNA variants led to a slight drop in editing efficiency compared to the control without spacers, which is Alt-R Carrier 3 (SEQ ID No. 4) (FIG. 9A). However, large numbers of C3 spacers (SEQ ID Nos. 58 and 59) or a combination of 58 C3 spacers and 42 dSpacers (SEQ ID No. 60) resulted in a significant drop in editing efficiency (FIG. 9A). A similar effect was seen when using dSpacers in the Cas9-related carrier DNA variant (SEQ ID Nos. 63 and 64). See FIG. 9B. The effect of blocked ends only was beneficial for the Cpf1-related carrier DNA variant (SEQ ID No. 65). See FIG. 9C. In conclusion, for carrier DNA to maintain a boosting effect on editing efficiency requires the presence of DNA residues. The DNA residues can be continuous or can be interrupted by the presence of non-base modifiers, such as C3 spacer (propanediol) or S9 spacer (triethylene glycol).

Figure 10A:
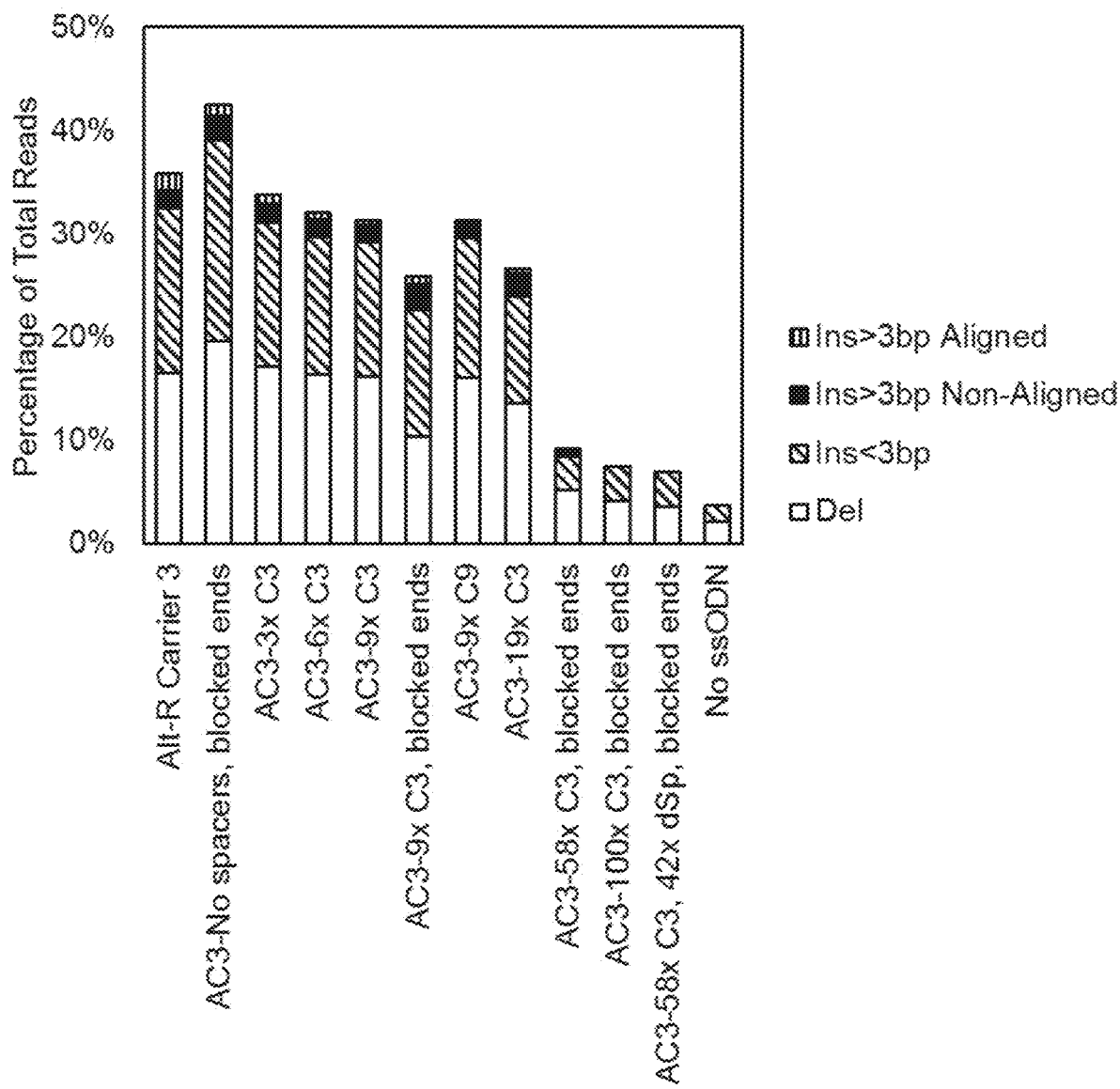
FIG. 10A illustrates the distribution of integration and deletion events for each carrier DNA variants Cas9 using carrier DNA variants with C3 or S9 spacers. The events were determined through next-generation sequencing.
Figure 10B:
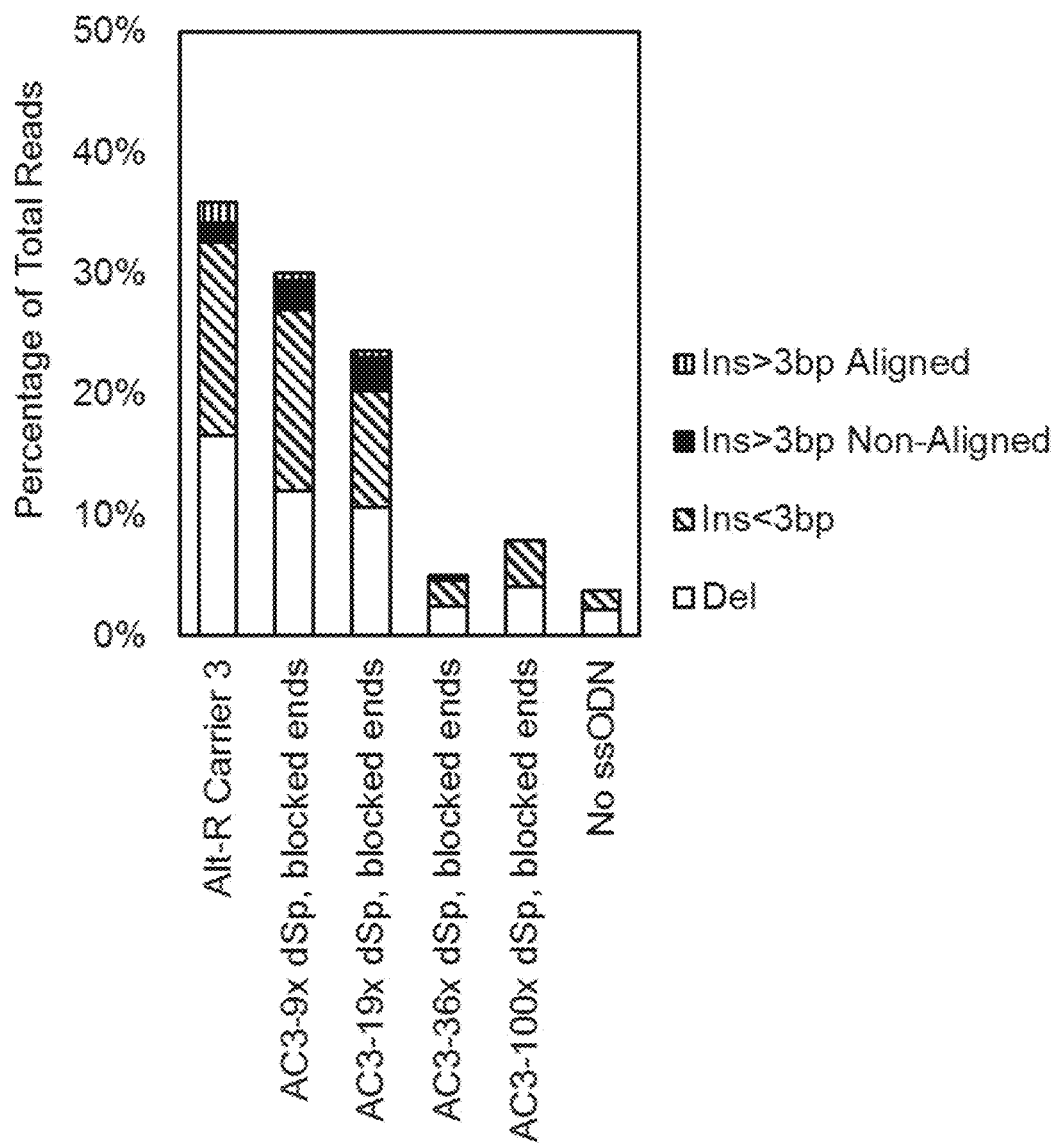
FIG. 10B shows the distribution of integration and deletion events for each carrier DNA variants Cas9 using Cas9 carrier DNA variants with abasic dSpacers. The events were determined as described in FIG. 10A.
Figure 10C:
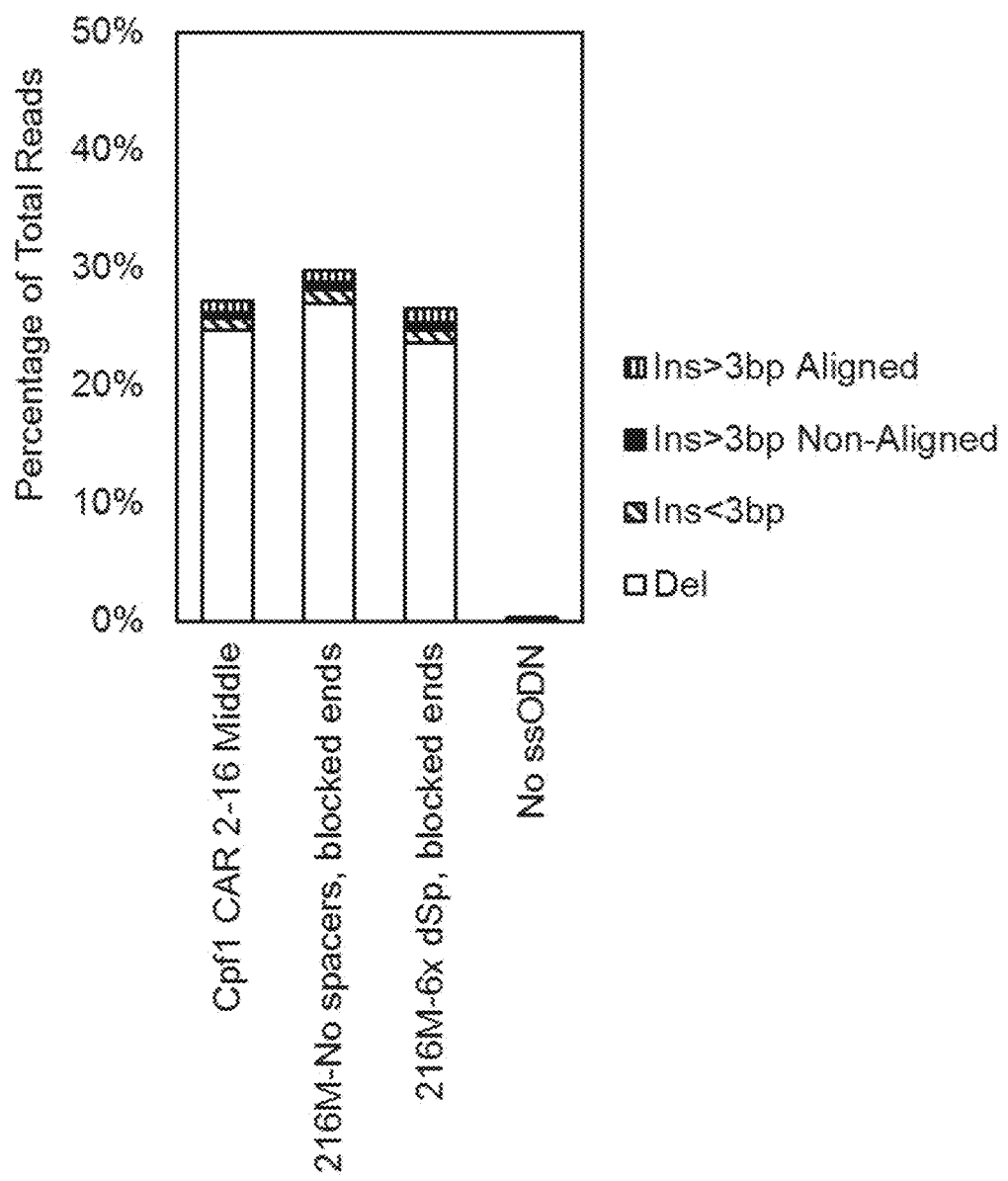
FIG. 10C shows the distribution of integration and deletion events for Cpf1 carrier DNA variants. The events were determined as described in FIG. 10A.
Figure 11A:
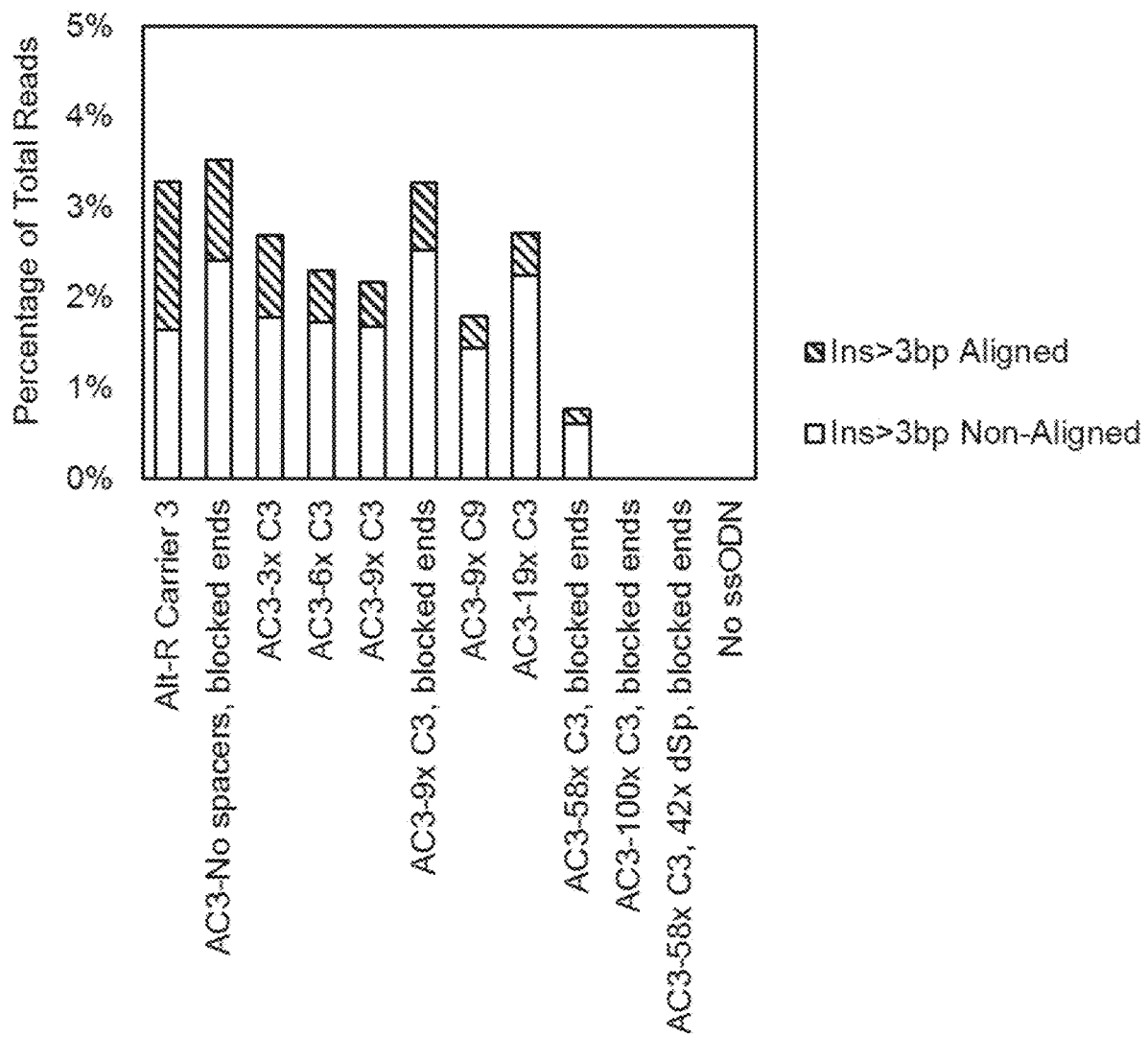
FIG. 11A illustrates the distribution of integration events of more than 3 basepairs for each carrier DNA variant using Cas9 carrier DNA variants with C3 or S9 spacers. The events were determined through next-generation sequencing. Solid black bars illustrate insertions of more than 3 basepairs that do not align with the carrier DNA, whereas striped bars illustrate insertions of more than 3 basepairs that do align with the carrier DNA.
Figure 11B:
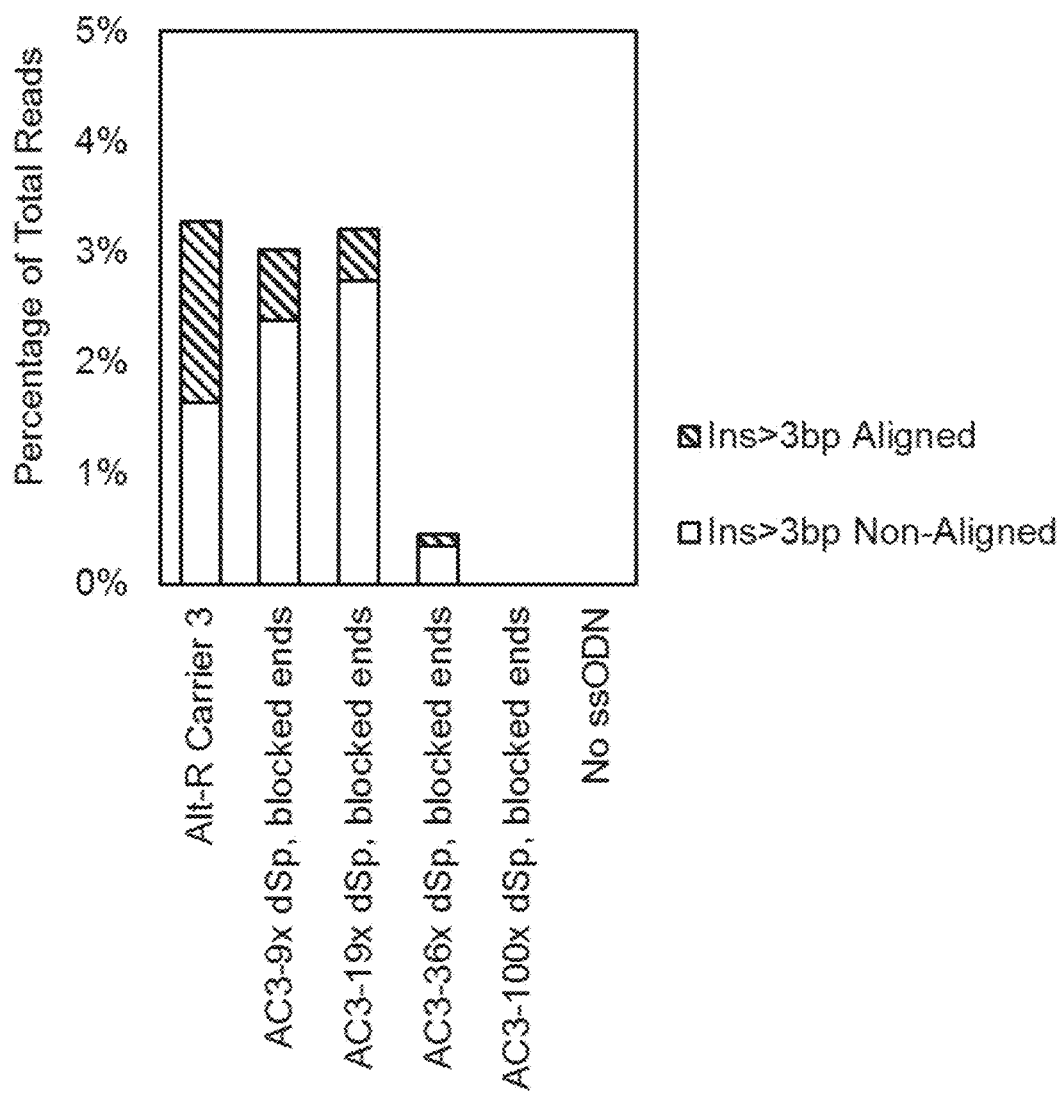
FIG. 11B illustrates the distribution of integration events of more than 3 basepairs for each carrier DNA variant using Cas9 carrier DNA variants with abasic dSpacers. The events were determined and analyzed as described in FIG. 11A.
Figure 11C:
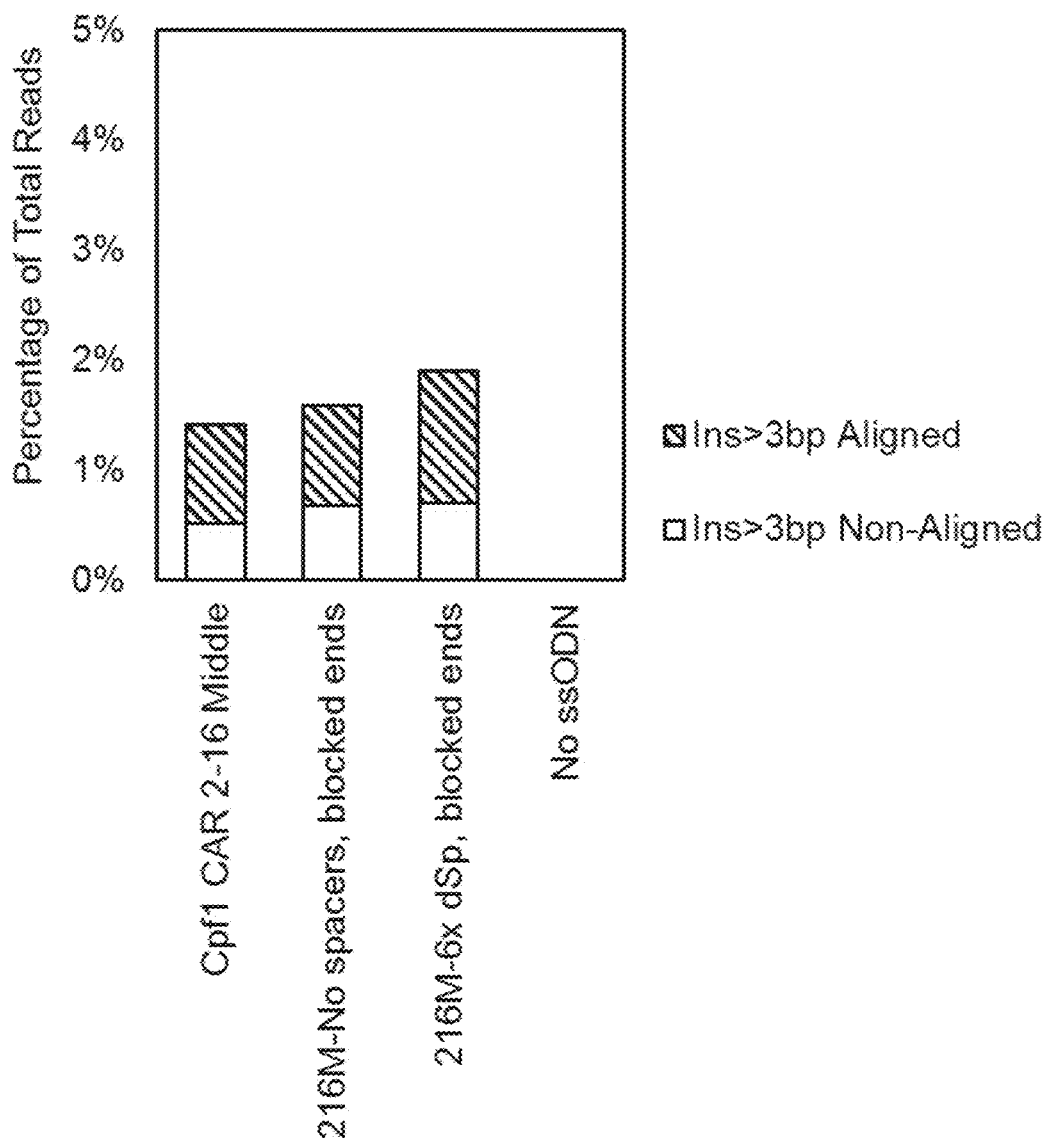
FIG. 11C illustrates the distribution of integration events of more than 3 basepairs for each carrier DNA variant using Cpf1 carrier DNA variants. The events were determined and analyzed as described in FIG. 11A.

The targeted next-generation sequencing data allowed for determination of specific editing events. For each variant, the percentage of deletions, insertions of 3 bp or less, insertions more than 3 bp without sequence homology to the variant, and insertions more than 3 bp with sequence homology to the variant were calculated (FIG. 10A-C). The distribution of deletions and insertions of less than 3 bp were similar between the different Cas9-related carrier DNA variants compared to total observed edits. These edits are not linked to integration of the carrier DNA. The insertions of more than 3 bp could reflect integration of the carrier DNA. These larger insertions were examined for sequence homology with the carrier DNA sequence. These larger integration events were relative occurring in small percentages, and therefore visualized on a separate graph (FIG. 11A-C). The ratio of aligned versus non-aligned insertions >3 bp were calculated (see Table 7).

TABLE 7

Ratio of aligned versus non-aligned insertions >3 bp.

| | SEQ ID No. | Ins >3 bp Aligned | Ins >3 bp Non-Aligned | Ratio |
|---|---|---|---|---|
| Cas9-C3/S9 spacers | | | | |
| Alt-R Carrier 3 | 4 | 1.63% | 1.65% | 0.99 |
| No spacers, blocked ends | 51 | 1.10% | 2.42% | 0.46 |
| 3x C3 | 52 | 0.90% | 1.79% | 0.51 |
| 6x C3 | 53 | 0.57% | 1.73% | 0.33 |
| 9x C3 | 54 | 0.49% | 1.69% | 0.29 |
| 9x C3, blocked ends | 55 | 0.74% | 2.53% | 0.29 |
| 9x S9 | 56 | 0.34% | 1.45% | 0.24 |
| 19x C3 | 57 | 0.46% | 2.25% | 0.20 |
| 58x C3, blocked ends | 58 | 0.16% | 0.61% | 0.27 |
| 100x C3, blocked ends | 59 | 0.00% | 0.00% | n/a |
| 58x C3, 42x dSp, blocked ends | 60 | 0.00% | 0.00% | n/a |
| No ssODN | n/a | 0.00% | 0.00% | n/a |
| Cas9-dSpacers | | | | |
| Alt-R Carrier 3 | 4 | 1.63% | 1.65% | 0.99 |
| 9x dSp, blocked ends | 61 | 0.64% | 2.38% | 0.27 |
| 19x dSp, blocked ends | 62 | 0.46% | 2.75% | 0.17 |
| 36x dSp, blocked ends | 63 | 0.10% | 0.35% | 0.29 |
| 100x dSp, blocked ends | 64 | 0.00% | 0.00% | n/a |
| No ssODN | n/a | 0.00% | 0.00% | n/a |
| Cpf1 | | | | |
| Cpf1 CAR 2-16 Middle | 25 | 0.91% | 0.51% | 1.78 |
| No spacers, blocked ends | 65 | 0.91% | 0.68% | 1.34 |
| 6x dSp, blocked ends | 66 | 1.19% | 0.70% | 1.70 |
| No ssODN | n/a | 0.00% | 0.00% | n/a |

With the inclusion of C3, S9, or dSpacers in the Cas9-related carrier DNA variants, a noticeable shift takes place where the percentage of insertions aligning to the carrier DNA drops. For instance, the Cas9-related Alt-R Carrier 3 (SEQ ID No. 4) shows an even distribution of aligned (1.63%) and non-aligned sequences (1.65%) resulting in a ratio of 0.99 (Table 7). The ratio becomes lower as more spacers are introduced, with 19× dSpacers (SEQ ID No. 62) showing the largest reduction (almost 6-fold, from 0.99 to 0.17). Thus, a negative correlation is observed between the number of spacers in the carrier DNA and the likelihood of integration of the carrier DNA.

The effects of placing spacers in the Cpf1-related carrier DNA showed a different pattern. The overall editing is heavily shifted to deletions when the Cpf1 nuclease is used (FIG. 10C). This is most likely caused by a different repair mechanism in the cell, as Cpf1 creates 5' overhangs when cleaving genomic DNA. Furthermore, the effect of spacers in the Cpf1-related carrier DNA (SEQ ID No. 66) showed limited effects, both on overall editing efficiency and reduction of integration events.

TABLE 8 crRNA protospacer sequences

| SEQ ID No. | Sequence | |
|---|---|---|
| SEQ ID No. 67: | HPRT 38285-AS protospacer | CTTATATCCAACACTTCGTG |
| SEQ ID No. 68: | HPRT 38104-S protospacer | CTTGGGTGTGTTAAAAGTGAC |
| SEQ ID No. 69: | HPRT 38094-S protospacer | ATAGTCTTTCCTTGGGTGTGT |
| SEQ ID No. 70: | HPRT 38115-AS protospacer | ACACACCCAAGGAAAGACTAT |
| SEQ ID No. 71: | HPRT 38146-AS protospacer | ATCCGTGCTGAGTGTACCATG |
| SEQ ID No. 72: | HPRT 38164-AS protospacer | TAAACACTGTTTCATTTCATC |
| SEQ ID No. 73: | HPRT 38164-S protospacer | GAAACGTCAGTCTTCTCTTTT |
| SEQ ID No. 74: | HPRT 38186-S protospacer | TAATGCCCTGTAGTCTCTCTG |
| SEQ ID No. 75: | HPRT 38228-S protospacer | TAATTAACAGCTTGCTGGTGA |
| SEQ ID No. 76: | HPRT 38330-AS protospacer | GGTTAAAGATGGTTAAATGAT |
| SEQ ID No. 77: | HPRT 38343-S protospacer | TGTGAAATGGCTTATAATTGC |
| SEQ ID No. 78: | HPRT 38455-S protospacer | GTTGTTGGATTTGAAATTCCA |
| SEQ ID No. 79: | HPRT 38486-S protospacer | TTGTAGGATATGCCCTTGACT |
| SEQ ID No. 80: | EMX1C3 protospacer | GAGTCCGAGCAGAAGAAGAA |

The crRNAs were synthesized based on the Alt-R® system (Integrated DNA Technologies).

TABLE 9

Primer sequences for PCR-based assays

| SEQ ID No. | Sequence | |
|---|---|---|
| SEQ ID No. 81: | T7EI HPRT FWD primer | AAGAATGTTGTGATAAAAGGTGATGCT |
| SEQ ID No. 82: | T7EI HPRT RVS primer | ACACATCCATGGGACTTCTGCCTC |
| SEQ ID No. 83: | NGS Cas9 HPRT FWD primer | CCCTGTAGTCTCTCTGTATGTTATAT |
| SEQ ID No. 84: | NGS Cas9 HPRT RVS primer | TGTGCCTCTCTACAAATATTCTCTA |
| SEQ ID No. 85: | NGS Cpf1 HPRT FWD primer | CAGAACTGTCCTTCAGGTTC |
| SEQ ID No. 86: | NGS Cpf1 HPRT RVS primer | CACTGTTTCATTTCATCCGTG |

All references, including publications, patent applications, and patents, cited herein are hereby incorporated by reference to the same extent as if each reference were individually and specifically indicated to be incorporated by reference and were set forth in its entirety herein.

The terms "carrier DNA", "carrier nucleic acid" and "carrier oligonucleotide" have the same meaning in the context of the present application and are used interchangeably herein. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A carrier oligonucleotide to improve transfection of ribonucleoprotein (RNP) into a cell in a sample, wherein the carrier oligonucleotide is selected from SEQ ID Nos.: 4, 9, and 25.

2. The carrier oligonucleotide of claim 1, wherein the carrier oligonucleotide is SEQ ID NO.: 4.

3. The carrier oligonucleotide of claim 1, wherein the carrier oligonucleotide is SEQ ID NO.: 9.

4. The carrier oligonucleotide of claim 1, wherein the carrier oligonucleotide is SEQ ID NO.: 25.

5. A method of improving transfection of a ribonucleoprotein into a cell of a sample, comprising:
   contacting the cell of the sample with composition having a carrier oligonucleotide,
   wherein the carrier oligonucleotide is selected from SEQ ID Nos.: 4, 9, and 25.

6. The method of claim 5, wherein the concentration of the carrier oligonucleotide in the composition is at least 1 µM.

7. The method of claim 5, wherein the carrier oligonucleotide is SEQ ID NO.: 4.

8. The method of claim 5, wherein the carrier oligonucleotide is SEQ ID NO.: 9.

9. The method of claim 5, wherein the carrier oligonucleotide is SEQ ID NO.: 25.

10. The method of claim 5, wherein the ribonucleoprotein comprises a Cpf1 ribonucleoprotein.

11. The method of claim 10, wherein the carrier oligonucleotide comprises SEQ ID No.: 4.

12. The method of claim 10, wherein the carrier oligonucleotide comprises SEQ ID NO.: 9.

13. The method of claim 10, wherein the carrier oligonucleotide comprises SEQ ID NO.: 25.

* * * * *

```
                           SEQUENCE LISTING

<160> NUMBER OF SEQ ID NOS: 91

<210> SEQ ID NO 1
<211> LENGTH: 95
<212> TYPE: DNA
<213> ORGANISM: Artificial Sequence
<220> FEATURE:
<223> OTHER INFORMATION: Synthetic DNA Oligonucleotide

<400> SEQUENCE: 1
ccagcagaac accccatcg gcgacggccc cgtgctgctg cccgacaacc actacctgag        60
cacccagtcc gccctgagca aagacccaa cgaga                                   95

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 2
ccagcagaac accccatcg                                                    20

<210> SEQ ID NO 3
<211> LENGTH: 200
<212> TYPE: DNA
<213> ORGANISM: Artificial Sequence
<220> FEATURE:
<223> OTHER INFORMATION: Synthetic DNA Oligonucleotide

<400> SEQUENCE: 3
aggacggcag cgtgcagctc gccgaccact accagcagaa caccccatc ggcgacggcc        60 ccgtgctgct gcccgacaac cactacctga gcacccagtc cgccctgagc aaagacccca      120
acgagaagcg cgatcacatg gtcctgctgg agttcgtgac cgccgccggg atcactctcg      180
gcatggacga gctgtacaag                                                  200

<210> SEQ ID NO 4
<211> LENGTH: 100
<212> TYPE: DNA
<213> ORGANISM: Artificial Sequence
<220> FEATURE:
<223> OTHER INFORMATION: Synthetic DNA Oligonucleotide

<400> SEQUENCE: 4
ttagctctgt ttacgtccca gcgggcatga gagtaacaag agggtgtggt aatattacgg       60
taccgagcac tatcgataca atatgtgtca tacggacacg                            100

<210> SEQ ID NO 5
<211> LENGTH: 100
<212> TYPE: DNA
<213> ORGANISM: Artificial Sequence
<220> FEATURE:
<223> OTHER INFORMATION: Synthetic DNA Oligonucleotide

<400> SEQUENCE: 5
gtcccagcgg gcatgagagt aacaagaggg tgtggtaata ttacggtacc gagcactatc       60
gatacaatat gtgtcatacg gacacgtaac tgacatacag                            100
```

<210> SEQ ID NO 6
<211> LENGTH: 104
<212> TYPE: DNA
<213> ORGANISM: Artificial Sequence
<220> FEATURE:
<223> OTHER INFORMATION: Synthetic DNA Oligonucleotide

<400> SEQUENCE: 6
cccagcgggc atgagagtaa caagagggtg tggtaatatt acggtaccga gcactatcga    60
tacaatatgt gtcatacgga cacggaaaca tgtaatcatg tttc                    104

<210> SEQ ID NO 7
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 7
cccagcgggc atgagagtaa caagagggtg tggtaatatt acggtaccga gcactatcga    60
tacaatatgt gtcatagaaa catgcgtgtc cgtaatcgga cacgcatgtt tc            112

<210> SEQ ID NO 8
<211> LENGTH: 104
<212> TYPE: DNA
<213> ORGANISM: Artificial Sequence
<220> FEATURE:
<223> OTHER INFORMATION: Synthetic DNA Oligonucleotide

<400> SEQUENCE: 8
tggataataa tgaacgcatt agatagattt gaatgccgga actttggatt tagatcaccc    60
attgacttgg tcaacgatag cgaagaaaca tgtaatcatg tttc                    104

<210> SEQ ID NO 9
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 9
tggataataa tgaacgcatt agatagattt gaatgccgga actttggatt tagatcaccc    60
attgacttgg tcaacggaaa catgttcgct attaatatag cgaacatgtt tc            112

<210> SEQ ID NO 10
<211> LENGTH: 100
<212> TYPE: DNA
<213> ORGANISM: Artificial Sequence
<220> FEATURE:
<223> OTHER INFORMATION: Synthetic DNA Oligonucleotide

<400> SEQUENCE: 10
ttagctctgt ttacgtccca gcgggcatga gagtaacaag agggtgtggt aatatttcgg    60
taccgagcac tttcgataca atatgtttca tacggacacg                         100

<210> SEQ ID NO 11
<211> LENGTH: 91
<212> TYPE: DNA
<213> ORGANISM: Artificial Sequence
<220> FEATURE:
<223> OTHER INFORMATION: Synthetic DNA Oligonucleotide

<400> SEQUENCE: 11

```
tggataataa tgaacgcatt agatagattt gaatgccgga actttggatt tagatcaccc      60
attgacttgg tcaacgatag cgaagaaagt a                                     91

<210> SEQ ID NO 12
<211> LENGTH: 98
<212> TYPE: DNA
<213> ORGANISM: Artificial Sequence
<220> FEATURE:
<223> OTHER INFORMATION: Synthetic DNA Oligonucleotide

<400> SEQUENCE: 12
tggataataa tgaacgcatt agatagattt gaatgccgga actttggatt tagatcaccc      60
attgacttgg tcaacgatag cgaagaaagt aatctttc                              98

<210> SEQ ID NO 13
<211> LENGTH: 52
<212> TYPE: DNA
<213> ORGANISM: Artificial Sequence
<220> FEATURE:
<223> OTHER INFORMATION: Synthetic DNA Oligonucleotide

<400> SEQUENCE: 13
attgacttgg tcaacggaaa catgttcgct attaatatag cgaacatgtt tc              52

<210> SEQ ID NO 14
<211> LENGTH: 82
<212> TYPE: DNA
<213> ORGANISM: Artificial Sequence
<220> FEATURE:
<223> OTHER INFORMATION: Synthetic DNA Oligonucleotide

<400> SEQUENCE: 14
gaatgccgga actttggatt tagatcaccc attgacttgg tcaacggaaa catgttcgct      60
attaatatag cgaacatgtt tc                                               82

<210> SEQ ID NO 15
<211> LENGTH: 112
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (2)..(4)
<223> OTHER INFORMATION: phosphorothioate internucleotide linkage
<220> FEATURE:
<221> NAME/KEY: misc_feature
<222> LOCATION: (110)..(112)
<223> OTHER INFORMATION: phosphorothioate internucleotide linkage

<400> SEQUENCE: 15
tggataataa tgaacgcatt agatagattt gaatgccgga actttggatt tagatcaccc      60
attgacttgg tcaacggaaa catgttcgct attaatatag cgaacatgtt tc             112

<210> SEQ ID NO 16
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 16
tggataataa tgaacgcatt agatagattt gaatgccgga actttggatt tagatcaccc      60
```

```
attgacttgg tcaacggaaa catgaaagct attaatatag ctttcatgtt tc            112
```

```
<210> SEQ ID NO 17
<211> LENGTH: 112
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (2)..(4)
<223> OTHER INFORMATION: phosphorothioate internucleotide linkage
<220> FEATURE:
<221> NAME/KEY: misc_feature
<222> LOCATION: (110)..(112)
<223> OTHER INFORMATION: phosphorothioate internucleotide linkage

<400> SEQUENCE: 17
tggataataa tgaacgcatt agatagattt gaatgccgga actttggatt tagatcaccc    60
attgacttgg tcaacggaaa catgaaagct attaatatag ctttcatgtt tc            112
```

```
<210> SEQ ID NO 18
<211> LENGTH: 112
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: modified_base
<222> LOCATION: (92)..(93)
<223> OTHER INFORMATION: 2'-O-methylated Uridine moiety
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (94)..(95)
<223> OTHER INFORMATION: 2'-O-methylated moiety
<220> FEATURE:
<221> NAME/KEY: modified_base
<222> LOCATION: (96)..(96)
<223> OTHER INFORMATION: 2'-O-methylated Uridine moiety
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (97)..(97)
<223> OTHER INFORMATION: 2'-O-methylated moiety

<400> SEQUENCE: 18
tggataataa tgaacgcatt agatagattt gaatgccgga actttggatt tagatcaccc    60
attgacttgg tcaacggaaa catgaaagct annaanatag ctttcatgtt tc            112
```

```
<210> SEQ ID NO 19
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 19
tggataataa tgaacgcatt agatagattt gaatgccgga actttggatt tagatcaccc    60
attgacttgg tcaacggttt catgttcgct attaatatag cgaacatgaa ac            112
```

```
<210> SEQ ID NO 20
<211> LENGTH: 112
```

<212> TYPE: DNA
<213> ORGANISM: Artificial Sequence
<220> FEATURE:
<223> OTHER INFORMATION: Synthetic DNA Oligonucleotide

<400> SEQUENCE: 20
tggataataa tgaacgcatt agatagataa gaatgccgga actaaggata aagatcaccc    60
attgacttgg tcaacgggca catgttcgct attaatatag cgaacatgtg cc            112

<210> SEQ ID NO 21
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 21
tggataataa tgaacgcatt agatagattt gaatgccgga actttggatt tagatcaccc    60
attgacttgg tcaacggcat gaaattcgct attaatatag cgaatttcat gc            112

<210> SEQ ID NO 22
<211> LENGTH: 83
<212> TYPE: DNA
<213> ORGANISM: Artificial Sequence
<220> FEATURE:
<223> OTHER INFORMATION: Synthetic DNA Oligonucleotide

<400> SEQUENCE: 22
tggataataa tgaacgcatt agatagattt gaatgcgaaa gtacggaact ttggatttag    60
atcacccatt gacttggtca acg                                           83

<210> SEQ ID NO 23
<211> LENGTH: 90
<212> TYPE: DNA
<213> ORGANISM: Artificial Sequence
<220> FEATURE:
<223> OTHER INFORMATION: Synthetic DNA Oligonucleotide

<400> SEQUENCE: 23
tggataataa tgaacgcatt agatagattt gaatgcgaaa gtaatctttc cggaactttg    60
gatttagatc acccattgac ttggtcaacg                                    90

<210> SEQ ID NO 24
<211> LENGTH: 96
<212> TYPE: DNA
<213> ORGANISM: Artificial Sequence
<220> FEATURE:
<223> OTHER INFORMATION: Synthetic DNA Oligonucleotide

<400> SEQUENCE: 24
tggataataa tgaacgcatt agatagattt gaatgcgaaa catgtaatca tgtttccgga    60
actttggatt tagatcaccc attgacttgg tcaacg                             96

<210> SEQ ID NO 25
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 25
tggataataa tgaacgcatt agatagattt gaatgcgaaa catgttcgct attaatatag    60

```
cgaacatgtt tccggaactt tggatttaga tcacccattg acttggtcaa cg            112
```

<210> SEQ ID NO 26
<211> LENGTH: 112
<212> TYPE: DNA
<213> ORGANISM: Artificial Sequence
<220> FEATURE:
<223> OTHER INFORMATION: Synthetic DNA Oigonucleotide

<400> SEQUENCE: 26

```
ctttgtacaa gcgatataat tatcgcttgt acaaagtgga taataatgaa cgcattagat    60
agatttgaat gccggaactt tggatttaga tcacccattg acttggtcaa cg            112
```

<210> SEQ ID NO 27
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 27

```
ctttgtactt tcgatataat tatcgaaagt acaaagtgga taataatgaa cgcattagat    60
agatttgaat gccggaactt tggatttaga tcacccattg acttggtcaa cg            112
```

<210> SEQ ID NO 28
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 28

```
caaagtacaa gcgatataat tatcgcttgt actttgtgga taataatgaa cgcattagat    60
agatttgaat gccggaactt tggatttaga tcacccattg acttggtcaa cg            112
```

<210> SEQ ID NO 29
<211> LENGTH: 112
<212> TYPE: DNA
<213> ORGANISM: Artificial Sequence
<220> FEATURE:
<223> OTHER INFORMATION: Synthetic DNA Oligonucleotide

<400> SEQUENCE: 29

```
cgctgtacaa gcgatataat tatcgcttgt acagcgtgga taataatgaa cgcattagat    60
agataagaat gccggaacta aggataaaga tcacccattg acttggtcaa cg            112
```

<210> SEQ ID NO 30
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 30

```
gaaacatgtt cgctattaat atagcgaaca tgtttctgga taataatgaa cgcattagat    60
agatttgaat gccggaactt tggatttaga tcacccattg acttggtcaa cggaaacatg   120
ttcgctatta atatagcgaa catgtttc                                      148
```

<210> SEQ ID NO 31
<211> LENGTH: 148
<212> TYPE: DNA
<213> ORGANISM: Artificial Sequence

```
<220> FEATURE:
<223> OTHER INFORMATION: Synthetic DNA Oligonucleotide

<400> SEQUENCE: 31
gtttcatgtt cgctattaat atagcgaaca tgaaactgga taataatgaa cgcattagat      60
agatttgaat gccggaactt tggatttaga tcacccattg acttggtcaa cggtttcatg     120
ttcgctatta atatagcgaa catgaaac                                        148

<210> SEQ ID NO 32
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 32
gaaacatgaa agctattaat atagctttca tgtttctgga taataatgaa cgcattagat      60
agatttgaat gccggaactt tggatttaga tcacccattg acttggtcaa cggaaacatg     120
aaagctatta atatagcttt catgtttc                                        148

<210> SEQ ID NO 33
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 33
gaaacatgtt cgctattaat atagcgaaca tgtttctgga taataatgaa cgcattagat      60
agatttgaat gccggaactt tggatttaga tcacccattg acttggtcaa cgggcacatg     120
ttcgctatta atatagcgaa catgtgcc                                        148

<210> SEQ ID NO 34
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 34
ggcacatgtt cgctattaat atagcgaaca tgtgcctgga taataatgaa cgcattagat      60
agatttgaat gccggaactt tggatttaga tcacccattg acttggtcaa cggaaacatg     120
ttcgctatta atatagcgaa catgtttc                                        148

<210> SEQ ID NO 35
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 35
ggcacatgtt cgctattaat atagcgaaca tgtgcctgga taataatgaa cgcattagat      60
agatttgaat gccggaactt tggatttaga tcacccattg acttggtcaa cgggcacatg     120
ttcgctatta atatagcgaa catgtgcc                                        148

<210> SEQ ID NO 36
<211> LENGTH: 148
<212> TYPE: DNA
```

```
<213> ORGANISM: Artificial Sequence
<220> FEATURE:
<223> OTHER INFORMATION: Synthetic DNA Oligonucleotide

<400> SEQUENCE: 36
ctttgtacaa gcgatataat tatcgcttgt acaaagtgga taataatgaa cgcattagat      60
agatttgaat gccggaactt tggatttaga tcacccattg acttggtcaa cggaaacatg     120
ttcgctatta atatagcgaa catgtttc                                        148

<210> SEQ ID NO 37
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 37
ctttgtactt tcgatataat tatcgaaagt acaaagtgga taataatgaa cgcattagat      60
agatttgaat gccggaactt tggatttaga tcacccattg acttggtcaa cggaaacatg     120
aaagctatta atatagcttt catgtttc                                        148

<210> SEQ ID NO 38
<211> LENGTH: 148
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (16)..(16)
<223> OTHER INFORMATION: 2'-O-methylated moiety
<220> FEATURE:
<221> NAME/KEY: modified_base
<222> LOCATION: (17)..(17)
<223> OTHER INFORMATION: 2'-O-methylated Uridine moiety
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (18)..(19)
<223> OTHER INFORMATION: 2'-O-methylated moiety
<220> FEATURE:
<221> NAME/KEY: modified_base
<222> LOCATION: (20)..(21)
<223> OTHER INFORMATION: 2'-O-methylated Uridine moiety
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (127)..(127)
<223> OTHER INFORMATION: 2'-O-methylated moiety
<220> FEATURE:
<221> NAME/KEY: modified_base
<222> LOCATION: (128)..(129)
<223> OTHER INFORMATION: 2'-O-methylated Uridine moiety
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (130)..(131)
<223> OTHER INFORMATION: 2'-O-methylated moiety
<220> FEATURE:
<221> NAME/KEY: modified_base
<222> LOCATION: (132)..(132)
<223> OTHER INFORMATION: 2'-O-methylated Uridine moiety
```

<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (133)..(133)
<223> OTHER INFORMATION: 2'-O-methylated moiety

<400> SEQUENCE: 38
ctttgtactt tcgatanaan natcgaaagt acaaagtgga taataatgaa cgcattagat      60
agatttgaat gccggaactt tggatttaga tcacccattg acttggtcaa cggaaacatg    120
aaagctanna anatagcttt catgtttc                                        148

<210> SEQ ID NO 39
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 39
ctttgtacaa gcgatataat tatcgcttgt acaaagtgga taataatgaa cgcattagat      60
agatttgaat gccggaactt tggatttaga tcacccattg acttggtcaa cgggcacatg    120
ttcgctatta atatagcgaa catgtgcc                                        148

<210> SEQ ID NO 40
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 40
cgctgtacaa gcgatataat tatcgcttgt acagcgtgga taataatgaa cgcattagat      60
agatttgaat gccggaactt tggatttaga tcacccattg acttggtcaa cggaaacatg    120
ttcgctatta atatagcgaa catgtttc                                        148

<210> SEQ ID NO 41
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 41
cgctgtacaa gcgatataat tatcgcttgt acagcgtgga taataatgaa cgcattagat      60
agatttgaat gccggaactt tggatttaga tcacccattg acttggtcaa cgggcacatg    120
ttcgctatta atatagcgaa catgtgcc                                        148

<210> SEQ ID NO 42
<211> LENGTH: 148
<212> TYPE: DNA
<213> ORGANISM: Artificial Sequence
<220> FEATURE:
<223> OTHER INFORMATION: Synthetic DNA Oigonucleotide

<400> SEQUENCE: 42
atttactagg ttacgctaat gcgtaaccta gtaaattgga taataatgaa cgcattagat      60
agatttgaat gccggaactt tggatttaga tcacccattg acttggtcaa cggaaacatg    120

```
ttcgctatta atatagcgaa catgtttc                                       148
```

<210> SEQ ID NO 43
<211> LENGTH: 148
<212> TYPE: DNA
<213> ORGANISM: Artificial Sequence
<220> FEATURE:
<223> OTHER INFORMATION: Synthetic DNA Oligonucleotide

<400> SEQUENCE: 43

```
agctactagg ttacgctaat gcgtaaccta gtagcttgga taataatgaa cgcattagat    60
agataagaat gccggaacta aggataaaga tcacccattg acttggtcaa cgggcacatg   120
ttcgctatta atatagcgaa catgtgcc                                      148
```

<210> SEQ ID NO 44
<211> LENGTH: 148
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (2)..(4)
<223> OTHER INFORMATION: phosphorothioate internucleotide linkage
<220> FEATURE:
<221> NAME/KEY: misc_feature
<222> LOCATION: (146)..(148)
<223> OTHER INFORMATION: phosphorothioate internucleotide linkage

<400> SEQUENCE: 44

```
atttactagg ttacgctaat gcgtaaccta gtaaattgga taataatgaa cgcattagat    60
agatttgaat gccggaactt tggatttaga tcacccattg acttggtcaa cggaaacatg   120
ttcgctatta atatagcgaa catgtttc                                      148
```

<210> SEQ ID NO 45
<211> LENGTH: 146
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (16)..(16)
<223> OTHER INFORMATION: 2'-O-methylated moiety
<220> FEATURE:
<221> NAME/KEY: modified_base
<222> LOCATION: (17)..(17)
<223> OTHER INFORMATION: 2'-O-methylated Uridine moiety
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (18)..(19)
<223> OTHER INFORMATION: 2'-O-methylated moiety
<220> FEATURE:
<221> NAME/KEY: modified_base
<222> LOCATION: (20)..(20)
<223> OTHER INFORMATION: 2'-O-methylated Uridine moiety
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (21)..(21)
<223> OTHER INFORMATION: 2'-O-methylated moiety
<220> FEATURE:
<221> NAME/KEY: misc_feature
<222> LOCATION: (126)..(126)
<223> OTHER INFORMATION: 2'-O-methylated moiety
<220> FEATURE:
<221> NAME/KEY: modified_base
<222> LOCATION: (127)..(128)
<223> OTHER INFORMATION: 2'-O-methylated Uridine moiety
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (129)..(129)
<223> OTHER INFORMATION: 2'-O-methylated moiety
<220> FEATURE:
<221> NAME/KEY: modified_base
<222> LOCATION: (130)..(130)
<223> OTHER INFORMATION: 2'-O-methylated Uridine moiety
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (131)..(131)
<223> OTHER INFORMATION: 2'-O-methylated moiety

<400> SEQUENCE: 45
atttactagg ttacgcnaan cgtaacctag taaattggat aataatgaac gcattagata     60
gatttgaatg ccggaacttt ggatttagat cacccattga cttggtcaac ggaaacatgt    120
tcgctannan atagcgaaca tgtttc                                          146

<210> SEQ ID NO 46
<211> LENGTH: 136
<212> TYPE: DNA
<213> ORGANISM: Artificial Sequence
<220> FEATURE:
<223> OTHER INFORMATION: Synthetic DNA Oligonucleotide

<400> SEQUENCE: 46
ttagctctgt ttacgtccca gcgggcatga gagtaacaag agggtgtggt aatattacgg     60
taccgagcac tatcgataca atatgtgtca tacggacacg gaaacatgtt cgctattaat    120
atagcgaaca tgtttc                                                    136

<210> SEQ ID NO 47
<211> LENGTH: 134
<212> TYPE: DNA
<213> ORGANISM: Artificial Sequence
<220> FEATURE:
<223> OTHER INFORMATION: Synthetic DNA Oligonucleotide

<400> SEQUENCE: 47
ttagctctgt ttacgtccca gcgggcatga gagtaacaag agggtgtggt aatattacgg     60
taccgagcac tatcgataca atatgtgtca gtttaattga gttgtcatat gttaataacg    120
gtattacgga cacg                                                      134

<210> SEQ ID NO 48
<211> LENGTH: 134
<212> TYPE: DNA
<213> ORGANISM: Artificial Sequence
<220> FEATURE:
<223> OTHER INFORMATION: Synthetic DNA Oligonucleotide

<400> SEQUENCE: 48
cgtgtccgta ataccgttat taacatatga caactcaatt aaactgacac atattgtatc     60

```
gatagtgctc ggtaccgtaa tattaccaca ccctcttgtt actctcatgc ccgctgggac    120
gtaaacagag ctaa                                                      134
```

<210> SEQ ID NO 49
<211> LENGTH: 34
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-phosphate moiety
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (33)..(34)
<223> OTHER INFORMATION: phosphorothioate internucleotide linkage
<400> SEQUENCE: 49

```
gtttaattga gttgtcatat gttaataacg gtat                                34
```

<210> SEQ ID NO 50
<211> LENGTH: 34
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-phosphate moiety
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (33)..(34)
<223> OTHER INFORMATION: phosphorothioate internucleotide linkage
<400> SEQUENCE: 50

```
ataccgttat taacatatga caactcaatt aaac                                34
```

<210> SEQ ID NO 51
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: misc_feature
<222> LOCATION: (100)..(100)
<223> OTHER INFORMATION: 3'-C3 spacer (propanediol)

<400> SEQUENCE: 51

```
ttagctctgt ttacgtccca gcgggcatga gagtaacaag agggtgtggt aatattacgg    60
taccgagcac tatcgataca atatgtgtca tacggacacg                          100
```

<210> SEQ ID NO 52
<211> LENGTH: 100
<212> TYPE: DNA
<213> ORGANISM: Artificial Sequence

```
<220> FEATURE:
<223> OTHER INFORMATION: Synthetic DNA Oligonucleotide
<220> FEATURE:
<221> NAME/KEY: misc_feature
<222> LOCATION: (11)..(11)
<223> OTHER INFORMATION: C3 spacer (propanediol)
<220> FEATURE:
<221> NAME/KEY: misc_feature
<222> LOCATION: (51)..(51)
<223> OTHER INFORMATION: C3 spacer (propanediol)
<220> FEATURE:
<221> NAME/KEY: misc_feature
<222> LOCATION: (91)..(91)
<223> OTHER INFORMATION: C3 spacer (propanediol)

<400> SEQUENCE: 52
ttagctctgt ttacgtccca gcgggcatga gagtaacaag agggtgtggt aatattacgg    60
taccgagcac tatcgataca atatgtgtca tacggacacg                         100

<210> SEQ ID NO 53
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (11)..(11)
<223> OTHER INFORMATION: C3 spacer (propanediol)
<220> FEATURE:
<221> NAME/KEY: misc_feature
<222> LOCATION: (41)..(41)
<223> OTHER INFORMATION: C3 spacer (propanediol)
<220> FEATURE:
<221> NAME/KEY: misc_feature
<222> LOCATION: (61)..(61)
<223> OTHER INFORMATION: C3 spacer (propanediol)
<220> FEATURE:
<221> NAME/KEY: misc_feature
<222> LOCATION: (91)..(91)
<223> OTHER INFORMATION: C3 spacer (propanediol)

<400> SEQUENCE: 53
ttagctctgt ttacgtccca gcgggcatga gagtaacaag agggtgtggt aatattacgg    60
taccgagcac tatcgataca atatgtgtca tacggacacg                         100

<210> SEQ ID NO 54
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (11)..(11)
<223> OTHER INFORMATION: C3 spacer (propanediol)
<220> FEATURE:
<221> NAME/KEY: misc_feature
<222> LOCATION: (21)..(21)
<223> OTHER INFORMATION: C3 spacer (propanediol)
<220> FEATURE:
<221> NAME/KEY: misc_feature
<222> LOCATION: (31)..(31)
<223> OTHER INFORMATION: C3 spacer (propanediol)
<220> FEATURE:
<221> NAME/KEY: misc_feature
<222> LOCATION: (41)..(41)
<223> OTHER INFORMATION: C3 spacer (propanediol)
<220> FEATURE:
<221> NAME/KEY: misc_feature
<222> LOCATION: (51)..(51)
<223> OTHER INFORMATION: C3 spacer (propanediol)
<220> FEATURE:
```

<221> NAME/KEY: misc_feature
<222> LOCATION: (61)..(61)
<223> OTHER INFORMATION: C3 spacer (propanediol)
<220> FEATURE:
<221> NAME/KEY: misc_feature
<222> LOCATION: (71)..(71)
<223> OTHER INFORMATION: C3 spacer (propanediol)
<220> FEATURE:
<221> NAME/KEY: misc_feature
<222> LOCATION: (81)..(81)
<223> OTHER INFORMATION: C3 spacer (propanediol)
<220> FEATURE:
<221> NAME/KEY: misc_feature
<222> LOCATION: (91)..(91)
<223> OTHER INFORMATION: C3 spacer (propanediol)

<400> SEQUENCE: 54
ttagctctgt ttacgtccca gcgggcatga gagtaacaag agggtgtggt aatattacgg    60
taccgagcac tatcgataca atatgtgtca tacggacacg                         100

<210> SEQ ID NO 55
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: misc_feature
<222> LOCATION: (11)..(11)
<223> OTHER INFORMATION: C3 spacer (propanediol)
<220> FEATURE:
<221> NAME/KEY: misc_feature
<222> LOCATION: (21)..(21)
<223> OTHER INFORMATION: C3 spacer (propanediol)
<220> FEATURE:
<221> NAME/KEY: misc_feature
<222> LOCATION: (31)..(31)
<223> OTHER INFORMATION: C3 spacer (propanediol)
<220> FEATURE:
<221> NAME/KEY: misc_feature
<222> LOCATION: (41)..(41)
<223> OTHER INFORMATION: C3 spacer (propanediol)
<220> FEATURE:
<221> NAME/KEY: misc_feature
<222> LOCATION: (51)..(51)
<223> OTHER INFORMATION: C3 spacer (propanediol)
<220> FEATURE:
<221> NAME/KEY: misc_feature
<222> LOCATION: (61)..(61)
<223> OTHER INFORMATION: C3 spacer (propanediol)
<220> FEATURE:
<221> NAME/KEY: misc_feature
<222> LOCATION: (71)..(71)
<223> OTHER INFORMATION: C3 spacer (propanediol)
<220> FEATURE:
<221> NAME/KEY: misc_feature
<222> LOCATION: (81)..(81)
<223> OTHER INFORMATION: C3 spacer (propanediol)
<220> FEATURE:
<221> NAME/KEY: misc_feature
<222> LOCATION: (91)..(91)
<223> OTHER INFORMATION: C3 spacer (propanediol)
<220> FEATURE:
<221> NAME/KEY: misc_feature
<222> LOCATION: (100)..(100)
<223> OTHER INFORMATION: 3'-C3 spacer (propanediol)

<400> SEQUENCE: 55
ttagctctgt ttacgtccca gcgggcatga gagtaacaag agggtgtggt aatattacgg    60
taccgagcac tatcgataca atatgtgtca tacggacacg                         100

<210> SEQ ID NO 56
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (11)..(11)
<223> OTHER INFORMATION: Spacer 9 (triethylene glycol)
<220> FEATURE:
<221> NAME/KEY: misc_feature
<222> LOCATION: (21)..(21)
<223> OTHER INFORMATION: Spacer 9 (triethylene glycol)
<220> FEATURE:
<221> NAME/KEY: misc_feature
<222> LOCATION: (31)..(31)
<223> OTHER INFORMATION: Spacer 9 (triethylene glycol)
<220> FEATURE:
<221> NAME/KEY: misc_feature
<222> LOCATION: (41)..(41)
<223> OTHER INFORMATION: Spacer 9 (triethylene glycol)
<220> FEATURE:
<221> NAME/KEY: misc_feature
<222> LOCATION: (51)..(51)
<223> OTHER INFORMATION: Spacer 9 (triethylene glycol)
<220> FEATURE:
<221> NAME/KEY: misc_feature
<222> LOCATION: (61)..(61)
<223> OTHER INFORMATION: Spacer 9 (triethylene glycol)
<220> FEATURE:
<221> NAME/KEY: misc_feature
<222> LOCATION: (71)..(71)
<223> OTHER INFORMATION: Spacer 9 (triethylene glycol)
<220> FEATURE:
<221> NAME/KEY: misc_feature
<222> LOCATION: (81)..(81)
<223> OTHER INFORMATION: Spacer 9 (triethylene glycol)
<220> FEATURE:
<221> NAME/KEY: misc_feature
<222> LOCATION: (91)..(91)
<223> OTHER INFORMATION: Spacer 9 (triethylene glycol)

<400> SEQUENCE: 56
ttagctctgt ttacgtccca gcgggcatga gagtaacaag agggtgtggt aatattacgg      60
taccgagcac tatcgataca atatgtgtca tacggacacg                           100

<210> SEQ ID NO 57
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (6)..(6)
<223> OTHER INFORMATION: C3 spacer (propanediol)
<220> FEATURE:
<221> NAME/KEY: misc_feature
<222> LOCATION: (11)..(11)
<223> OTHER INFORMATION: C3 spacer (propanediol)
<220> FEATURE:
<221> NAME/KEY: misc_feature
<222> LOCATION: (16)..(16)
<223> OTHER INFORMATION: C3 spacer (propanediol)
<220> FEATURE:
<221> NAME/KEY: misc_feature
<222> LOCATION: (21)..(21)
<223> OTHER INFORMATION: C3 spacer (propanediol)
<220> FEATURE:
<221> NAME/KEY: misc_feature
<222> LOCATION: (26)..(26)
<223> OTHER INFORMATION: C3 spacer (propanediol)
<220> FEATURE:

```
<221> NAME/KEY: misc_feature
<222> LOCATION: (31)..(31)
<223> OTHER INFORMATION: C3 spacer (propanediol)
<220> FEATURE:
<221> NAME/KEY: misc_feature
<222> LOCATION: (36)..(36)
<223> OTHER INFORMATION: C3 spacer (propanediol)
<220> FEATURE:
<221> NAME/KEY: misc_feature
<222> LOCATION: (41)..(41)
<223> OTHER INFORMATION: C3 spacer (propanediol)
<220> FEATURE:
<221> NAME/KEY: misc_feature
<222> LOCATION: (46)..(46)
<223> OTHER INFORMATION: C3 spacer (propanediol)
<220> FEATURE:
<221> NAME/KEY: misc_feature
<222> LOCATION: (51)..(51)
<223> OTHER INFORMATION: C3 spacer (propanediol)
<220> FEATURE:
<221> NAME/KEY: misc_feature
<222> LOCATION: (56)..(56)
<223> OTHER INFORMATION: C3 spacer (propanediol)
<220> FEATURE:
<221> NAME/KEY: misc_feature
<222> LOCATION: (61)..(61)
<223> OTHER INFORMATION: C3 spacer (propanediol)
<220> FEATURE:
<221> NAME/KEY: misc_feature
<222> LOCATION: (66)..(66)
<223> OTHER INFORMATION: C3 spacer (propanediol)
<220> FEATURE:
<221> NAME/KEY: misc_feature
<222> LOCATION: (71)..(71)
<223> OTHER INFORMATION: C3 spacer (propanediol)
<220> FEATURE:
<221> NAME/KEY: misc_feature
<222> LOCATION: (76)..(76)
<223> OTHER INFORMATION: C3 spacer (propanediol)
<220> FEATURE:
<221> NAME/KEY: misc_feature
<222> LOCATION: (81)..(81)
<223> OTHER INFORMATION: C3 spacer (propanediol)
<220> FEATURE:
<221> NAME/KEY: misc_feature
<222> LOCATION: (86)..(86)
<223> OTHER INFORMATION: C3 spacer (propanediol)
<220> FEATURE:
<221> NAME/KEY: misc_feature
<222> LOCATION: (91)..(91)
<223> OTHER INFORMATION: C3 spacer (propanediol)
<220> FEATURE:
<221> NAME/KEY: misc_feature
<222> LOCATION: (96)..(96)
<223> OTHER INFORMATION: C3 spacer (propanediol)

<400> SEQUENCE: 57
ttagctctgt ttacgtccca gcgggcatga gagtaacaag agggtgtggt aatattacgg      60
taccgagcac tatcgataca atatgtgtca tacggacacg                          100

<210> SEQ ID NO 58
<211> LENGTH: 42
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 4 x C3 spacer (propanediol) linkers
<220> FEATURE:
<221> NAME/KEY: misc_feature
<222> LOCATION: (4)..(4)
<223> OTHER INFORMATION: 4 x C3 spacer (propanediol) linkers
<220> FEATURE:
<221> NAME/KEY: misc_feature
```

```
<222> LOCATION: (7)..(7)
<223> OTHER INFORMATION: 4 x C3 spacer (propanediol) linkers
<220> FEATURE:
<221> NAME/KEY: misc_feature
<222> LOCATION: (10)..(10)
<223> OTHER INFORMATION: 4 x C3 spacer (propanediol) linkers
<220> FEATURE:
<221> NAME/KEY: misc_feature
<222> LOCATION: (13)..(13)
<223> OTHER INFORMATION: 4 x C3 spacer (propanediol) linkers
<220> FEATURE:
<221> NAME/KEY: misc_feature
<222> LOCATION: (16)..(16)
<223> OTHER INFORMATION: 4 x C3 spacer (propanediol) linkers
<220> FEATURE:
<221> NAME/KEY: misc_feature
<222> LOCATION: (19)..(19)
<223> OTHER INFORMATION: 4 x C3 spacer (propanediol) linkers
<220> FEATURE:
<221> NAME/KEY: misc_feature
<222> LOCATION: (22)..(22)
<223> OTHER INFORMATION: 4 x C3 spacer (propanediol) linkers
<220> FEATURE:
<221> NAME/KEY: misc_feature
<222> LOCATION: (25)..(25)
<223> OTHER INFORMATION: 4 x C3 spacer (propanediol) linkers
<220> FEATURE:
<221> NAME/KEY: misc_feature
<222> LOCATION: (28)..(28)
<223> OTHER INFORMATION: 4 x C3 spacer (propanediol) linkers
<220> FEATURE:
<221> NAME/KEY: misc_feature
<222> LOCATION: (31)..(31)
<223> OTHER INFORMATION: 4 x C3 spacer (propanediol) linkers
<220> FEATURE:
<221> NAME/KEY: misc_feature
<222> LOCATION: (34)..(34)
<223> OTHER INFORMATION: 4 x C3 spacer (propanediol) linkers
<220> FEATURE:
<221> NAME/KEY: misc_feature
<222> LOCATION: (37)..(37)
<223> OTHER INFORMATION: 4 x C3 spacer (propanediol) linkers
<220> FEATURE:
<221> NAME/KEY: misc_feature
<222> LOCATION: (40)..(40)
<223> OTHER INFORMATION: 4 x C3 spacer (propanediol) linkers
<220> FEATURE:
<221> NAME/KEY: misc_feature
<222> LOCATION: (42)..(42)
<223> OTHER INFORMATION: 3'- 4 x C3 spacer (propanediol) linkers

<400> SEQUENCE: 58
cggcggcggc ggcggcggcg gcggcggcgg cggcggcggc gg                           42

<210> SEQ ID NO 59
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: modified_base
<222> LOCATION: (1)..(100)
<223> OTHER INFORMATION: C3 spacer (propanediol)
<220> FEATURE:
<221> NAME/KEY: misc_feature
<222> LOCATION: (1)..(100)
<223> OTHER INFORMATION: n is a, c, g, or t

<400> SEQUENCE: 59
nnnnnnnnnn nnnnnnnnnn nnnnnnnnnn nnnnnnnnnn nnnnnnnnnn nnnnnnnnnn        60
nnnnnnnnnn nnnnnnnnnn nnnnnnnnnn nnnnnnnnnn                             100

<210> SEQ ID NO 60
```

```
<211> LENGTH: 42
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: modified_base
<222> LOCATION: (1)..(42)
<223> OTHER INFORMATION: dSpacer (abasic ribose) moiety
<220> FEATURE:
<221> NAME/KEY: misc_feature
<222> LOCATION: (1)..(1)
<223> OTHER INFORMATION: 4 x C3 spacer (propanediol) linkers
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (4)..(4)
<223> OTHER INFORMATION: 4 x C3 spacer (propanediol) linkers
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (7)..(7)
<223> OTHER INFORMATION: 4 x C3 spacer (propanediol) linkers
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (10)..(10)
<223> OTHER INFORMATION: 4 x C3 spacer (propanediol) linkers
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (13)..(13)
<223> OTHER INFORMATION: 4 x C3 spacer (propanediol) linkers
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (16)..(16)
<223> OTHER INFORMATION: 4 x C3 spacer (propanediol) linkers
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: 4 x C3 spacer (propanediol) linkers
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: 4 x C3 spacer (propanediol) linkers
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: 4 x C3 spacer (propanediol) linkers
<220> FEATURE:
<221> NAME/KEY: misc_feature
```

```
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: 4 x C3 spacer (propanediol) linkers
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: 4 x C3 spacer (propanediol) linkers
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: 4 x C3 spacer (propanediol) linkers
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: 4 x C3 spacer (propanediol) linkers
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: 4 x C3 spacer (propanediol) linkers
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (42)..(42)
<223> OTHER INFORMATION: 3'- 4 x C3 spacer (propanediol) linkers

<400> SEQUENCE: 60
nnnnnnnnnn nnnnnnnnnn nnnnnnnnnn nnnnnnnnnn nn                              42

<210> SEQ ID NO 61
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: modified_base
<222> LOCATION: (11)..(11)
<223> OTHER INFORMATION: dSpacer (abasic ribose)
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (21)..(21)
<223> OTHER INFORMATION: dSpacer (abasic ribose)
<220> FEATURE:
<221> NAME/KEY: misc_feature
<222> LOCATION: (21)..(21)
<223> OTHER INFORMATION: n is a, c, g, or t
<220> FEATURE:
```

```
<221> NAME/KEY: modified_base
<222> LOCATION: (31)..(31)
<223> OTHER INFORMATION: dSpacer (abasic ribose)
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: modified_base
<222> LOCATION: (41)..(41)
<223> OTHER INFORMATION: dSpacer (abasic ribose)
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: modified_base
<222> LOCATION: (51)..(51)
<223> OTHER INFORMATION: dSpacer (abasic ribose)
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: modified_base
<222> LOCATION: (61)..(61)
<223> OTHER INFORMATION: dSpacer (abasic ribose)
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: modified_base
<222> LOCATION: (71)..(71)
<223> OTHER INFORMATION: dSpacer (abasic ribose)
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: modified_base
<222> LOCATION: (81)..(81)
<223> OTHER INFORMATION: dSpacer (abasic ribose)
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: modified_base
<222> LOCATION: (91)..(91)
<223> OTHER INFORMATION: dSpacer (abasic ribose)
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (100)..(100)

<400> SEQUENCE: 61
ttagctctgt ntacgtccca ncgggcatga nagtaacaag ngggtgtggt natattacgg    60
naccgagcac natcgataca ntatgtgtca nacggacacg                         100

<210> SEQ ID NO 62
<211> LENGTH: 119
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: modified_base
<222> LOCATION: (6)..(6)
```

```
<223> OTHER INFORMATION: dSpacer (abasic ribose)
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (12)..(12)
<223> OTHER INFORMATION: dSpacer (abasic ribose)
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (18)..(18)
<223> OTHER INFORMATION: dSpacer (abasic ribose)
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: modified_base
<222> LOCATION: (24)..(24)
<223> OTHER INFORMATION: dSpacer (abasic ribose)
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: modified_base
<222> LOCATION: (30)..(30)
<223> OTHER INFORMATION: dSpacer (abasic ribose)
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: modified_base
<222> LOCATION: (36)..(36)
<223> OTHER INFORMATION: dSpacer (abasic ribose)
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: modified_base
<222> LOCATION: (42)..(42)
<223> OTHER INFORMATION: dSpacer (abasic ribose)
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: modified_base
<222> LOCATION: (48)..(48)
<223> OTHER INFORMATION: dSpacer (abasic ribose)
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: modified_base
<222> LOCATION: (54)..(54)
<223> OTHER INFORMATION: dSpacer (abasic ribose)
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: modified_base
<222> LOCATION: (60)..(60)
<223> OTHER INFORMATION: dSpacer (abasic ribose)
<220> FEATURE:
<221> NAME/KEY: modified_base
<222> LOCATION: (60)..(60)
<223> OTHER INFORMATION: dSpacer (abasic ribose)
<220> FEATURE:
<221> NAME/KEY: misc_feature
```

```
<222> LOCATION: (60)..(60)
<223> OTHER INFORMATION: n is a, c, g, or t
<220> FEATURE:
<221> NAME/KEY: modified_base
<222> LOCATION: (66)..(66)
<223> OTHER INFORMATION: dSpacer (abasic ribose)
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: modified_base
<222> LOCATION: (72)..(72)
<223> OTHER INFORMATION: dSpacer (abasic ribose)
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: modified_base
<222> LOCATION: (78)..(78)
<223> OTHER INFORMATION: dSpacer (abasic ribose)
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: modified_base
<222> LOCATION: (84)..(84)
<223> OTHER INFORMATION: dSpacer (abasic ribose)
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: modified_base
<222> LOCATION: (90)..(90)
<223> OTHER INFORMATION: dSpacer (abasic ribose)
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: modified_base
<222> LOCATION: (96)..(96)
<223> OTHER INFORMATION: dSpacer (abasic ribose)
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: modified_base
<222> LOCATION: (102)..(102)
<223> OTHER INFORMATION: dSpacer (abasic ribose)
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: modified_base
<222> LOCATION: (108)..(108)
<223> OTHER INFORMATION: dSpacer (abasic ribose)
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: modified_base
<222> LOCATION: (114)..(114)
<223> OTHER INFORMATION: dSpacer (abasic ribose)
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (119)..(119)
<223> OTHER INFORMATION: 3.-C3 spacer (propanediol)
```

-continued

<400> SEQUENCE: 62
ttagcntctg tnttacgntc ccangcgggn catgangagt anacaagnag ggtngtggtn    60
aatatntacg gntaccgnag cacntatcgn atacanatat gntgtcanta cggnacacg    119

<210> SEQ ID NO 63
<211> LENGTH: 87
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: modified_base
<222> LOCATION: (1)..(2)
<223> OTHER INFORMATION: dSpacer (abasic ribose)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (6)..(7)
<223> OTHER INFORMATION: dSpacer (abasic ribose)
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: modified_base
<222> LOCATION: (11)..(12)
<223> OTHER INFORMATION: dSpacer (abasic ribose)
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: modified_base
<222> LOCATION: (16)..(17)
<223> OTHER INFORMATION: dSpacer (abasic ribose)
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: modified_base
<222> LOCATION: (21)..(22)
<223> OTHER INFORMATION: dSpacer (abasic ribose)
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: modified_base
<222> LOCATION: (26)..(27)
<223> OTHER INFORMATION: dSpacer (abasic ribose)
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (31)..(32)
<223> OTHER INFORMATION: dSpacer (abasic ribose)
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (36)..(37)
<223> OTHER INFORMATION: dSpacer (abasic ribose)
<220> FEATURE:
<221> NAME/KEY: misc_feature

```
<222> LOCATION: (36)..(37)
<223> OTHER INFORMATION: n is a, c, g, or t
<220> FEATURE:
<221> NAME/KEY: modified_base
<222> LOCATION: (41)..(42)
<223> OTHER INFORMATION: dSpacer (abasic ribose)
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (46)..(47)
<223> OTHER INFORMATION: dSpacer (abasic ribose)
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: modified_base
<222> LOCATION: (51)..(52)
<223> OTHER INFORMATION: dSpacer (abasic ribose)
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: modified_base
<222> LOCATION: (56)..(57)
<223> OTHER INFORMATION: dSpacer (abasic ribose)
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: modified_base
<222> LOCATION: (61)..(62)
<223> OTHER INFORMATION: dSpacer (abasic ribose)
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: modified_base
<222> LOCATION: (66)..(67)
<223> OTHER INFORMATION: dSpacer (abasic ribose)
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: modified_base
<222> LOCATION: (71)..(72)
<223> OTHER INFORMATION: dSpacer (abasic ribose)
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: modified_base
<222> LOCATION: (76)..(77)
<223> OTHER INFORMATION: dSpacer (abasic ribose)
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: modified_base
<222> LOCATION: (81)..(82)
<223> OTHER INFORMATION: dSpacer (abasic ribose)
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: modified_base
<222> LOCATION: (86)..(87)
<223> OTHER INFORMATION: dSpacer (abasic ribose)
<220> FEATURE:
```

```
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (87)..(87)
<223> OTHER INFORMATION: 3'-C3 spacer (propanediol)

<400> SEQUENCE: 63
nncggnncgg nncggnncgg nncggnncgg nncggnncgg nncggnncgg nncggnncgg      60
nncggnncgg nncggnncgg nncggnn                                         87

<210> SEQ ID NO 64
<211> LENGTH: 100
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: modified_base
<222> LOCATION: (1)..(100)
<223> OTHER INFORMATION: dSpacer (abasic ribose)
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: misc_feature
<222> LOCATION: (2)..(99)
<223> OTHER INFORMATION: n is a, c, g, or t
<220> FEATURE:
<221> NAME/KEY: misc_feature
<222> LOCATION: (100)..(100)
<223> OTHER INFORMATION: 3'-C3 spacer (propanediol)

<400> SEQUENCE: 64
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                          100

<210> SEQ ID NO 65
<211> LENGTH: 112
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: misc_feature
<222> LOCATION: (112)..(112)
<223> OTHER INFORMATION: 3'-C3 spacer (propanediol)

<400> SEQUENCE: 65
tggataataa tgaacgcatt agatagattt gaatgcgaaa catgttcgct attaatatag      60
cgaacatgtt tccggaactt tggatttaga tcacccattg acttggtcaa cg            112

<210> SEQ ID NO 66
<211> LENGTH: 112
<212> TYPE: DNA
<213> ORGANISM: Artificial Sequence
<220> FEATURE:
<223> OTHER INFORMATION: Synthetic DNA Oligonucleotide
<220> FEATURE:
<221> NAME/KEY: misc_feature
<222> LOCATION: (1)..(1)
<223> OTHER INFORMATION: 5'-C3 spacer (propanediol)
<220> FEATURE:
<221> NAME/KEY: misc_feature
```

```
<222> LOCATION: (11)..(11)
<223> OTHER INFORMATION: C3 spacer (propanediol)
<220> FEATURE:
<221> NAME/KEY: misc_feature
<222> LOCATION: (21)..(21)
<223> OTHER INFORMATION: C3 spacer (propanediol)
<220> FEATURE:
<221> NAME/KEY: misc_feature
<222> LOCATION: (31)..(31)
<223> OTHER INFORMATION: C3 spacer (propanediol)
<220> FEATURE:
<221> NAME/KEY: misc_feature
<222> LOCATION: (83)..(83)
<223> OTHER INFORMATION: C3 spacer (propanediol)
<220> FEATURE:
<221> NAME/KEY: misc_feature
<222> LOCATION: (93)..(93)
<223> OTHER INFORMATION: C3 spacer (propanediol)
<220> FEATURE:
<221> NAME/KEY: misc_feature
<222> LOCATION: (103)..(103)
<223> OTHER INFORMATION: C3 spacer (propanediol)
<220> FEATURE:
<221> NAME/KEY: misc_feature
<222> LOCATION: (112)..(112)
<223> OTHER INFORMATION: 3'-C3 spacer (propanediol)

<400> SEQUENCE: 66
tggataataa tgaacgcatt agatagattt gaatgcgaaa catgttcgct attaatatag        60
cgaacatgtt tccggaactt tggatttaga tcacccattg acttggtcaa cg              112

<210> SEQ ID NO 67
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 67
cttatatcca acacttcgtg                                                    20

<210> SEQ ID NO 68
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 68
cttgggtgtg ttaaaagtga c                                                  21

<210> SEQ ID NO 69
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 69
atagtctttc cttgggtgtg t                                                  21

<210> SEQ ID NO 70
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 70
```

```
acacacccaa ggaaagacta t                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 71
atccgtgctg agtgtaccat g                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 72
taaacactgt tcatttcat c                                               21

<210> SEQ ID NO 73
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 73
gaaacgtcag tcttctcttt t                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 74
taatgccctg tagtctctct g                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 75
taattaacag cttgctggtg a                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 76
ggttaaagat ggttaaatga t                                              21

<210> SEQ ID NO 77
<211> LENGTH: 21
<212> TYPE: DNA
<213> ORGANISM: Artificial Sequence
```

```
<220> FEATURE:
<223> OTHER INFORMATION: Synthetic DNA Oligonucleotide

<400> SEQUENCE: 77
tgtgaaatgg cttataattg c                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 78
gttgttggat ttgaaattcc a                                              21

<210> SEQ ID NO 79
<211> LENGTH: 21
<212> TYPE: DNA
<213> ORGANISM: Artificial Sequence
<220> FEATURE:
<223> OTHER INFORMATION: Synthetic DNA Oligonucleotide

<400> SEQUENCE: 79
ttgtaggata tgcccttgac t                                              21

<210> SEQ ID NO 80
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 80
gagtccgagc agaagaagaa                                                20

<210> SEQ ID NO 81
<211> LENGTH: 27
<212> TYPE: DNA
<213> ORGANISM: Artificial Sequence
<220> FEATURE:
<223> OTHER INFORMATION: Synthetic DNA Oligonucleotide

<400> SEQUENCE: 81
aagaatgttg tgataaaagg tgatgct                                        27

<210> SEQ ID NO 82
<211> LENGTH: 24
<212> TYPE: DNA
<213> ORGANISM: Artificial Sequence
<220> FEATURE:
<223> OTHER INFORMATION: Synthetic DNA Oligonucleotide

<400> SEQUENCE: 82
acacatccat gggacttctg cctc                                           24

<210> SEQ ID NO 83
<211> LENGTH: 26
<212> TYPE: DNA
<213> ORGANISM: Artificial Sequence
<220> FEATURE:
<223> OTHER INFORMATION: Synthetic DNA Oligonucleotide

<400> SEQUENCE: 83
ccctgtagtc tctctgtatg ttatat                                         26
```

```
<210> SEQ ID NO 84
<211> LENGTH: 25
<212> TYPE: DNA
<213> ORGANISM: Artificial Sequence
<220> FEATURE:
<223> OTHER INFORMATION: Synthetic DNA Oligonucleotide

<400> SEQUENCE: 84
tgtgcctctc tacaaatatt ctcta                                          25

<210> SEQ ID NO 85
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 85
cagaactgtc cttcaggttc                                                20

<210> SEQ ID NO 86
<211> LENGTH: 21
<212> TYPE: DNA
<213> ORGANISM: Artificial Sequence
<220> FEATURE:
<223> OTHER INFORMATION: Synthetic DNA Oligonucleotdide

<400> SEQUENCE: 86
cactgtttca tttcatccgt g                                              21

<210> SEQ ID NO 87
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 87
gagttagagc agaagaagaa                                                20

<210> SEQ ID NO 88
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 88
gagtctaagc agaagaagaa                                                20

<210> SEQ ID NO 89
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 89
gaggccgagc agaagaaaga                                                20

<210> SEQ ID NO 90
<211> LENGTH: 20
<212> TYPE: DNA
<213> ORGANISM: Artificial Sequence
<220> FEATURE:
<223> OTHER INFORMATION: Synthetic DNA Oligonucleotide
```

```
<400> SEQUENCE: 90
cacagctagc agaaaaagta                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic DNA Oligonucleotide

<400> SEQUENCE: 91
aagtctgagc acaagaagaa                                              20
```